US012410445B2

(12) United States Patent
Lahusen et al.

(10) Patent No.: US 12,410,445 B2
(45) Date of Patent: *Sep. 9, 2025

(54) VECTOR SYSTEM FOR EXPRESSING REGULATORY RNA

(71) Applicant: American Gene Technologies International Inc., Rockville, MD (US)

(72) Inventors: Tyler Lahusen, Rockville, MD (US); Lingzhi Xiao, Rockville, MD (US); Charles David Pauza, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 476 days.

This patent is subject to a terminal disclaimer.

(21) Appl. No.: 17/701,488

(22) Filed: Mar. 22, 2022

(65) Prior Publication Data

US 2022/0372513 A1 Nov. 24, 2022

Related U.S. Application Data

(63) Continuation of application No. 17/289,653, filed as application No. PCT/US2019/059828 on Nov. 5, 2019, now Pat. No. 11,352,646.

(60) Provisional application No. 62/755,985, filed on Nov. 5, 2018.

(51) Int. Cl.
*C12N 15/86* (2006.01)
*C12N 15/113* (2010.01)

(52) U.S. Cl.
CPC ............ *C12N 15/86* (2013.01); *C12N 15/113* (2013.01); *C12N 2310/14* (2013.01); *C12N 2740/15023* (2013.01); *C12N 2740/15043* (2013.01)

(58) Field of Classification Search
None
See application file for complete search history.

(56) References Cited

U.S. PATENT DOCUMENTS

| | | | |
|---|---|---|---|
| 8,124,752 | B2 | 2/2012 | Bumcrot et al. |
| 8,287,857 | B2 | 10/2012 | Dudley et al. |
| 9,834,790 | B1 | 12/2017 | Pauza et al. |
| 9,914,938 | B2 | 3/2018 | Pauza et al. |
| 10,023,880 | B2 | 7/2018 | Pauza et al. |
| 10,036,040 | B2 | 7/2018 | Pauza et al. |
| 10,137,144 | B2 | 11/2018 | Pauza et al. |
| 10,420,789 | B2 | 9/2019 | Pauza et al. |
| 10,428,350 | B2 | 10/2019 | Pauza et al. |
| 10,472,649 | B2 | 11/2019 | Pauza et al. |
| 10,767,183 | B2 | 9/2020 | Lahusen et al. |
| 10,772,905 | B2 | 9/2020 | Pauza et al. |
| 2004/0180847 | A1 | 9/2004 | Dobie et al. |
| 2004/0192629 | A1 | 9/2004 | Xu et al. |
| 2004/0248296 | A1 | 12/2004 | Beresford et al. |
| 2004/0265306 | A1 | 12/2004 | Arthos et al. |
| 2005/0019927 | A1 | 1/2005 | Markus et al. |
| 2006/0057553 | A1 | 3/2006 | Aguilar-Cordova |
| 2006/0073576 | A1 | 4/2006 | Barnett et al. |
| 2006/0246520 | A1 | 11/2006 | Champagne et al. |
| 2007/0141679 | A1 | 6/2007 | Sodroski |
| 2008/0003225 | A1 | 1/2008 | Vie et al. |
| 2008/0003682 | A1 | 1/2008 | Lois-Caballe et al. |
| 2008/0153737 | A1 | 6/2008 | Lieberman et al. |
| 2008/0199961 | A1 | 8/2008 | Rasko et al. |
| 2008/0227736 | A1 | 9/2008 | Chen et al. |
| 2008/0293142 | A1 | 11/2008 | Liu et al. |
| 2009/0148936 | A1 | 6/2009 | Stout et al. |
| 2009/0304688 | A1 | 12/2009 | Fournie et al. |
| 2010/0316676 | A1 | 12/2010 | Sanders |
| 2011/0008803 | A1 | 1/2011 | Stockwell et al. |
| 2012/0027725 | A1 | 2/2012 | Galvin et al. |
| 2013/0090371 | A1 | 4/2013 | Lu et al. |
| 2013/0122380 | A1 | 5/2013 | Visco et al. |
| 2014/0155468 | A1 | 6/2014 | Gregory et al. |
| 2014/0178340 | A1 | 6/2014 | Robbins et al. |
| 2014/0348794 | A1 | 11/2014 | Chiorini et al. |
| 2015/0010578 | A1 | 1/2015 | Balazs et al. |
| 2015/0018539 | A1 | 1/2015 | Fellmann |
| 2015/0126580 | A1 | 5/2015 | DePinho et al. |
| 2016/0060707 | A1 | 3/2016 | Goldenberg et al. |
| 2016/0243169 | A1 | 8/2016 | Chen et al. |
| 2016/0287635 | A1 | 10/2016 | Hariri et al. |
| 2017/0015976 | A1 | 1/2017 | Nelson |
| 2017/0335344 | A1 | 11/2017 | Pauza et al. |
| 2018/0142257 | A1 | 5/2018 | Pauza |
| 2018/0142258 | A1 | 5/2018 | Pauza |
| 2018/0195050 | A1 | 7/2018 | Szalay |
| 2018/0256624 | A1 | 9/2018 | Pauza |

(Continued)

FOREIGN PATENT DOCUMENTS

| | | |
|---|---|---|
| CN | 101516365 | 8/2009 |
| CN | 101679466 | 3/2010 |

(Continued)

OTHER PUBLICATIONS

JP Office Action in Japanese Application No. 2021-523916, dated Apr. 18, 2023.

(Continued)

*Primary Examiner* — Michael D Burkhart
(74) *Attorney, Agent, or Firm* — COOLEY LLP

(57) ABSTRACT

Viral vectors, lentiviral particles, and modified cells are disclosed. They encode or express a small RNA capable of targeting the KIF11 gene. In embodiments, the viral vectors and lentiviral particles further comprise and a KIF11 gene whose non-coding region has been modified such that it is resistant to activity by the small RNA.

17 Claims, 13 Drawing Sheets

Specification includes a Sequence Listing.

(56) References Cited

U.S. PATENT DOCUMENTS

| | | | |
|---|---|---|---|
| 2018/0305716 | A1 | 10/2018 | Pauza et al. |
| 2018/0355032 | A1 | 12/2018 | Roberts |
| 2019/0062786 | A1 | 2/2019 | Pauza et al. |
| 2019/0078096 | A1 | 3/2019 | Lahusen et al. |
| 2019/0083523 | A1 | 3/2019 | Pauza |
| 2019/0218573 | A1 | 7/2019 | Pauza et al. |
| 2019/0388456 | A1 | 12/2019 | Pauza et al. |
| 2020/0017570 | A1 | 1/2020 | Walcheck et al. |
| 2020/0063161 | A1 | 2/2020 | Pauza |
| 2020/0181645 | A1 | 6/2020 | Pauza |
| 2020/0354679 | A1 | 11/2020 | Niazi |
| 2021/0047644 | A1 | 2/2021 | Lahusen |

FOREIGN PATENT DOCUMENTS

| | | |
|---|---|---|
| CN | 101805750 | 8/2010 |
| CN | 105112370 | 12/2015 |
| CN | 108883100 | 11/2018 |
| EP | 3402483 | 11/2018 |
| EP | 3426777 | 1/2019 |
| JP | 2007-527240 | 9/2007 |
| JP | 2008-538174 | 10/2008 |
| JP | 2013-530152 | 7/2013 |
| JP | 2015-518838 | 7/2015 |
| JP | 2016-502404 | 1/2016 |
| WO | WO 2002020554 | 3/2002 |
| WO | WO 2005033282 | 4/2005 |
| WO | WO2006039721 | 4/2006 |
| WO | WO-2006089001 A2 | 8/2006 |
| WO | WO2007000668 | 1/2007 |
| WO | WO2007015122 | 2/2007 |
| WO | WO2007132292 | 11/2007 |
| WO | WO2008025025 | 2/2008 |
| WO | WO 2009001224 A2 | 12/2008 |
| WO | WO 2009100928 | 8/2009 |
| WO | WO 2009147445 | 12/2009 |
| WO | WO-2010051521 A1 | 5/2010 |
| WO | WO2010111522 | 9/2010 |
| WO | WO2010117974 | 10/2010 |
| WO | WO2010119039 | 10/2010 |
| WO | WO2010127166 | 11/2010 |
| WO | WO2011008348 | 1/2011 |
| WO | WO2012071559 | 5/2011 |
| WO | WO-2011148194 A1 | 12/2011 |
| WO | WO2012048303 | 4/2012 |
| WO | WO 2012061075 | 5/2012 |
| WO | WO2012145624 | 10/2012 |
| WO | WO2013056148 | 4/2013 |
| WO | WO2013096455 | 6/2013 |
| WO | WO2014117050 | 7/2014 |
| WO | WO 2014187881 | 11/2014 |
| WO | WO2014195159 | 12/2014 |
| WO | WO2015017755 | 2/2015 |
| WO | WO2015078999 | 6/2015 |
| WO | WO2015164759 | 10/2015 |
| WO | WO20170068077 | 4/2017 |
| WO | WO2017123918 | 7/2017 |
| WO | WO2017156311 | 9/2017 |
| WO | WO2017165641 | 9/2017 |
| WO | WO20170173453 | 10/2017 |
| WO | WO2018009246 | 1/2018 |
| WO | WO2018148443 | 8/2018 |
| WO | WO2018232359 | 12/2018 |
| WO | WO2020011247 | 1/2020 |
| WO | WO2020097049 | 5/2020 |
| WO | WO2021178571 | 10/2021 |

OTHER PUBLICATIONS

JP Office Action in Japanese Application No. 2021-045605, dated Apr. 19, 2023.
IL Office Action issued in Application No. 271274 on Aug. 6, 2023, 11 pages.
Fujiwara et al., "A Nucleolar Stress-Specific p53-miR-101 Molecular Circuit Functions as an Intrinsic Tumor-Suppressor Network," EBioMedicine 33, pp. 33-48, 2018.
Tian et al., "MicroRNA-30a Promotes Chondrogenic Differentiation of Mesenchymal Stem Cells Through Inhibiting Delta-Like 4 Expression," Life Sciences, 148, pp. 220-228, 2016.
Wang et al., "Kinesin Family Member 11 is a Potential Therapeutic Target and is Suppressed by MicroRNA-30a in Breast Cancer," Molecular Carcinogenesis, 59, pp. 908-922, 2020.
Ueda et al., "CD47-dependent molecular mechanisms of blood outgrowth endothelial call attachment on cholesterol-modified polyurethane," Biomaterials, vol. 31, No. 25, pp. 6394-6399, Sep. 1, 2010.
Sandstrom et al., The Intracellular B30.2 Domain of Butrophilin 3A1 Binds Phosphoantigens to Mediate Activation of Human Vγ9Vδ2 T Cells, Immunity, vol. 40, No. 4, pp. 490-500, 2014.
Wilkin et al. "Isolation and Sequence of the Human Farnesyl Pyrophosphate Synthetase eDNA," The Journal of Biological Chemestry, vol. 265, No. 8, pp. 4607-4614, Mar. 15, 1990.
USPTO; Final Office Action dated Aug. 2, 2022 is U.S. Appl. No. 16/614,682.
JP Office Action issued Jul. 11, 2022 in App. No. 2018-536892.
JP Office Action issued Jul. 12, 2022 in App. No. 2021-523916.
EPO; Extended Search Report dated Jul. 4, 2022 in EP Application No. 22154806.8.
EPO; Extended Search Report dated Jul. 21, 2022 in EP Application No. 19883230.5.
JP; Office Action issued in Application No. 2022-006999 on Sep. 20, 2023.
USPTO; Examiner's Answer in U.S. Appl. No. 16/614,682, dated Sep. 27, 2023.
Brake et al., "Lentiviral Vector Design for Multiple shRNA Expression and Durable HIV-1 Inhibition," Molecular Therapy, 16(3), 557-564, 2008.
KR; Office Action issued Oct. 20, 2023 in Application No. 10-2020-7000631.
UAE; Office Action issued Oct. 20, 2023 in Application No. P6001801/2019.
JP; Office Action issued Oct. 19, 2023 in Application No. 2021-523916.
JP Office Action in Japanese Application No. 2022-006999, dated Jan. 5, 2023, 20 pages (with English translation).
{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&RID=H3FCKA00014; pp. 1.
Benyamine et al., "BTN3A molecules considerably improve Vγ9Vδ2T cells-based immunotherapy in acute myeloid leukemia," Oncolmmunology, vol. 5, No. 10, 10 pages, (Oct. 2, 2016), E1146843 *the whole document*.
Capietto et al., "Stimulated γδ T Cells Increase the in Vivo Efficacy of Trastuzumab in HER-2+ Breast Cancer," J Immunology, vol. 187(2), pp. 1031-1038, (2011).
Chen et al., "An unconventional TRAIL to cancer therapy", Eur J Immunol, 2013, 43:3159-3162.
Chen et al., "CD16+ γδ T Cells Mediate Antibody Dependent Cellular Cytotoxicity: Potential Mechanism in the Pathogenesis of Multiple Sclerosis," Clin Immunology, vol. 128(2), pp. 219-227, (2008).
CN Office Action in Chinese Application No. 201780017712.6, dated Feb. 3, 2021, 10 pages (with English translation).
CN Office Action in Chinese Application No. 201780017712.6, dated May 14, 2021, 8 pages (with English translation).
CN Office Action in Chinese Application No. 201780017712.6, dated Feb. 3, 2021, 18 pages (with English translation).
CN; 1st Office Action in the CN Application No. 20170017712.6 dated May 8, 2020.
CN; 1st Office Action in the CN Application No. 202010396594.8 dated Jan. 15, 2021.
Condiotti et al., "Prolonged Liver-Specific Transgene Expression by a Non-Primate Lentiviral Vector," Biochemical and Biophysical Research Communications, vol. 320(3), pp. 998-1006, (Jul. 30, 2004).

(56) References Cited

OTHER PUBLICATIONS

Couzi et al., "Antibody-Dependent Anti-Cytomegalovirus Activity of Human γδ T Cells Expressing CD16 (FcγRIIIa)," Blood, vol. 119(6), pp. 1418-1427, (2012).
Davis-Gardner et al., "eCD4-Ig promotes ADCC activity of sera from HIV-1-infected patients", Department of Immunology and Microbiology, The Scripps Research Institute, PLOS Pathogen, Dec. 18, 2017, https://doi.org/10.1371/journal.ppat.1006786.
Dieli et al., "Targeting Human γδ T Cells with Zoledronate and Interleukin-2 for Immunotherapy of Hormone-Refractory Prostate Cancer," Europe PMC Funders Group, Cancer Research, vol. 67(15), pp. 7450-1451, (Aug. 1, 2007).
Ding et al., "Administration-Route and Gender-Independent Longterm Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 1, 2005).
EP Office Action in European Application No. 17739028.3, dated Mar. 18, 2022.
EP; Supplementary Search Report in the EP Application No. 18817253 dated Feb. 10, 2021.
EPO; European Search Report dated Aug. 12, 2019 in the EP Application No. 17764128.9.
EPO; Extended Search Report dated Jun. 6, 2019 in EP Application No. 17739028.3.
Fisher et al., "Effective Combination Treatment of GD2-Expressing Neuroblastoma and Ewing's Sarcoma Using Anti-GD2 ch14.18/CHO Antibody with Vγ9Vδ 2+ γδT Cells," OncoImmunology, vol. 5(1), pp. e1025194, (2016).
GenBank Accession No. JG619773, MNESC1NG-T3-001_L15_6FEB2009_054 MNESC1NG cell culture from Mahonia nervosa Berberis nervosa cDNA, mRNA sequence, Feb. 13, 2014 (online). [Retrieved on Dec. 5, 2017]. Retrieved from the internet:<URL:https://www.ncbi.nlm.nih.gov/nucest/JG619773 > entire document.
Gertner-Dardenne et al., "Bromohydrin pyrophosphate enhances antibody-dependent cell-mediated cytotoxicity induced by therapeutic antibodies," Blood 113(20): 4875-4884, (2009).
Gober et al., "Human T Cell Receptor γδ Cells Recognize Endogenous Mevalonate Metabolites in Tumor Cells," J. of Experimental Med., Jan. 20, 2003, vol. 197, pp. 163-168.
Harly et al., "Key implication of CD277/butyrophilin-3 (BTN3A) in cellular stress sensing by a major human γδ T-cell subset," American Society of Hematology, vol. 120, No. 11, (Sep. 13, 2012), pp. 2269-2279, XP055081172, ISSN: 0006-4971, DOI: 10.1182/blood-2012-05-430470 *the whole document*.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 25, 2012).
Jiang, "A novel EST-derived RNAi screen reveals a critical role for farnesyl diphophate in B2-adrenerigic receptor internalization and down-regulation,", The FASEB Journal, vol. 26, pp. 1-13(1995).
JP Notice of Allowance in Japanese Application No. 2018-547354, dated Dec. 17, 2021, 6 pages (with English translation).
JP; Final Office Action in the JP Application No. 2018-536892 dated Nov. 16, 2020.
JP; Japanese Office Action in the Application No. 2018-536892 dated Jun. 26, 2020.
JP; Office Action in the JP Application No. 2018-547354 dated Feb. 16, 2021.
Kim, "Farnesyl diphosphate synthase is important for the maintenance of glioblastoma stemness," Experimental & Molecular Medicine, (2018).
Li et al., "Reduced Expression of the Mevalonate Pathway Enzyme Farnesyl Pyrophosphate Synthase Unveils Recognition of Tumor Cells by Vγ2Vδ2 T Cells," J. of Immunology, 2009, vol. 182, pp. 8118-8124.
Li, "Inhibition of farnesyl pyrophosphate synthase prevents angiotensin II-induced cardiac fibrosis in vitro," Clinical & Experimental Immunology, (2014).
Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).
Lu et al., "Anti-sense-Mediated Inhibition of Human Immunodeficiency Virus (HIV) Replication by Use of an HIV Type 1-Based Vector Results in Severely Attenuated Mutants Incapable of Developing Resistance,", Journal of Virology, vol. 79, No. 13, pp. 7079-7088 (Jul. 2004).
Miettinen et al., "Mevalonate Pathway Regulates Cell Size Homeostasis and Proteostasis Through Autophagy," Cell Reports, vol. 13(11), pp. 2610-2620, (Dec. 2015).
Moser et al., "γδ T cells: novel initiators of adaptive immunity," Immunological Reviews, vol. 215, pp. 89-102 (Feb. 2, 2007).
Nada et al., "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6 *the whole document*.
Nowacki et al., "The PAH Mutation Analysis Consortium Database: Update 1996," Nucleic Acid Research, vol. 25(1), pp. 139-142, (Jan. 1, 1997).
Oh et al. "Lentiviral Vector Design Using Alternative RNA Export Elements," Retrovirology, vol. 4:38, pp. 1-10, (2007).
Ostertag et al., "Brain Tumor Eradication and Prolonged Survival from Intratumoral Conversion of 5-Fluorocytosine to 5-fluorouracil Using a Nonlytic Retroviral Replicating Vector," Neoro-Oncology 14(2), pp. 145-159, Feb. 2012.
PCT: International Search report dated Aug. 25, 2017 in Application No. PCT/US2017/021639.
PCT: International Search Report dated May 26, 2017 in Application No. PCT/US2017/013399.
PCT: Written Opinion dated Aug. 25, 2017 Application No. PCT/US2017/021639.
PCT: Written Opinion dated May 26, 2017 in Application No. PCT/US2017/013399.
PCT; International Search Report and Written Opinion in the PCT Application No. PCT/US2019/059828 dated Feb. 14, 2020.
PCT; International Search Report and Written Opinion in the PCT Application No. PCT/US2021/020721 dated Jul. 21, 2021.
PCT; International Search Report dated Nov. 9, 2018 in Application No. PCT/US2018/037924.
PCT; Notice of Publication in the PCT Application No. PCT/US2021/020721 dated Sep. 10, 2021.
PCT; Written Opinion dated Nov. 9, 2018 in Application No. PCT/US2018/037924.
Poonia et al., "Gamma delta T cells from HIV+ donors can be expanded in vitro by zoledronate/interleukin-2 to become cytotoxic effectors for antibody-dependent cellular cytotoxicity," Cytotherapy 14(2): 173-181, (2012).
Riaño et al., "Vγ9Vδ2 TCR-activation by phosphorylated antigens required butyrophilin 3 Al (BTN3A1) and additional genes on human chromosome 6", Eur J Immunol, 2014, 44: 2571-2576.
Schille et al., "CD19-Specific Triplebody SPM-1 Engages NK and γδ T Cells for Rapid and Efficient Lysis of Malignant B-Lymphoid Cells," Oncotarget, vol. 7(50), pp. 83392-83408, (2016).
Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).

(56) References Cited

OTHER PUBLICATIONS

Stunkel et al., "The Chromatin Structure of the Long Control Region of Human Papillomavirus Type 16 Repress Viral Oncoprotein Expression," Journal Of Virology, vol. 73, No. 3, pp. 1918-1930 (Mar. 1999).
Thompson et al., "Alkylamines cause Vγ9Vδ2 T-cell activation and proliferation by inhibiting the mevalonate pathway," Blood, Jan. 15, 2006, vol. 107, pp. 651-654.
Tokuyama et al., "Vy9Vδ2 T Cell Cytotoxicity Against Tumor Cells is Enhanced by Monoclonal Antibody Drugs—Rituximab and Trastuzumab," Int J Cancer, vol. 122(11), pp. 2526-2534, (2008).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 24, 2013).
Twitty et al., "Retroviral Replicating Vectors Deliver Cytosine Deaminase Leading to Targeted 5-Fluorouracil-Mediated Cytotoxicity in Multiple Human Cancer Types, Human Gene Therapy Methods", 27(1), pp. 17-31, Feb. 1, 2016.
US Non-Final Office Action in U.S. Appl. No. 16/614,682, dated Feb. 28, 2022, 75 pages.
US Notice of Allowance in U.S. Appl. No. 17/198,017, dated Nov. 3, 2021, 6 pages.
US Notice of Allowance in U.S. Appl. No. 17/289,653, dated Jan. 5, 2022, 9 pages.
USPTO; Final Office Action dated Jul. 1, 2019 in the U.S. Appl. No. 16/132,247.
USPTO; Final Office Action dated May 2, 2019 in U.S. Appl. No. 16/182,443.
USPTO; Invitation to Pay Additional Fees And, Where Applicable, Protest Fee dated Sep. 11, 2018 in Application No. PCT/US2018/37924.
USPTO; Non-Final Office Action dated Dec. 31, 2018 in U.S. Appl. No. 16/182,443.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Jul. 20, 2021 in the U.S. Appl. No. 17/198,017.
USPTO; Non-Final Office Action dated Jun. 1, 2020 in the U.S. Appl. No. 16/530,908.
USPTO; Non-Final Office Action dated Jun. 15, 2018 in U.S. Appl. No. 15/904,131.
USPTO; Non-Final Office Action dated Mar. 12, 2021 in the U.S. Appl. No. 16/563,738.
USPTO; Non-Final Office Action dated Mar. 16, 2020 in the U.S. Appl. No. 16/083,384.
USPTO; Non-Final Office Action dated May 7, 2019 in U.S. Appl. No. 16/008,991.
USPTO; Non-Final Office Action dated May 16, 2019 in U.S. Appl. No. 16/132,247.
USPTO; Non-Final Office Action dated Nov. 25, 2020 in the U.S. Appl. No. 16/943,800.
USPTO; Notice Allowance dated Apr. 26, 2018 in U.S. Appl. No. 15/849,062.
USPTO; Notice of Allowance dated Apr. 23, 2018 in U.S. Appl. No. 15/850,937.
USPTO; Notice of Allowance dated Aug. 14, 2019 in the U.S. Appl. No. 16/008,991.
USPTO; Notice of Allowance dated Feb. 10, 2021 in the U.S. Appl. No. 16/943,800.
USPTO; Notice of Allowance dated Jul. 10, 2020 in the U.S. Appl. No. 16/530,908.
USPTO; Notice of Allowance dated Jul. 19, 2019 in the U.S. Appl. No. 16/132,247.
USPTO; Notice of Allowance dated Jul. 3, 2019 in U.S. Appl. No. 16/182,443.
USPTO; Notice of Allowance dated Jun. 18, 2019 in the U.S. Appl. No. 16/182,443.
USPTO; Notice of Allowance dated May 18, 2020 in the U.S. Appl. No. 16/083,384.
USPTO; Notice of Allowance dated Nov. 2, 2017 in U.S. Appl. No. 15/652,080.
USPTO; Notice of Allowance dated Oct. 13, 2017 in U.S. Appl. No. 14/706,481.
USPTO; Restriction Requirement dated Nov. 7, 2019 in the U.S. Appl. No. 16/083,384.
USPTO; Restriction Requirement dated Dec. 8, 2020 in the U.S. Appl. No. 16/563,738.
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 5, 2013).
Wang et al., "Indirect Stimulation of Human Vy2Vδ2 T Cells through Alterations in Isoprenoid Metabolism," J. of Immunology, vol. 187 pp. 5099-5113, (Nov. 15, 2011).
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
Wang, "Indirect Stimulation of Human V2V2 Cells Through Aleterations in Isoprenoid Metabolism," The Journal of Immunology, (2011).
Yang, "Lentiviral-Mediated Silencing of Farnelsyl Pyrophosphate Synthase through RNA Interference in Mice," Biomed Research International, vol. 2015, Article ID 914026, 6 pages, (2015).
AU; Examination Report issued in Application No. 2021203836 on Jan. 30, 2024.
EP; Search Report issued in Application No. 23199847.7 on Mar. 5, 2024.
Cheng et al., "Establishment, Characterization, and Successful Adaptive Therapy Against Human Tumors of NKG Cell, a New Human NK Cell Line", Cell Transplantation, Jun. 2011, 20:1731-1746.
Herrera et al., "Adult peripheral blood and umbilical cord blood NK cells are good sources for effective CAR therapy against CD19 positive leukemic cells", Scientific Reports, Dec. 2019, 9(18729), 2 pages.
Mensali et al., "NK cells specifically TCR-dressed to kill cancer cells", EBioMedicine, Jan. 2019, 40:106-117.
PCT International Search Report and Written Opinion in International Application No. PCT/US2022/013422, dated May 13, 2022, 20 pages.
Shalova et al., "CD16 Regulates TRIF-Dependent TLR4 Response in Human Monocytes and Their Subsets", The Journal of Immunology, 2012, 188:3584-3593.
CA Office Action in Canadian Application No. 3,011,529, dated Feb. 21, 2023, 7 pages.
JP Office Action in Japanese Application No. 2018-536892, dated Jan. 30, 2023, 4 pages (with English translation).
JP Office Action in Japanese Application No. 2021-045605, dated Nov. 2, 2022, 8 pages (with English translation).
CN Notice of Allowance in Chinese Application No. 201780017712.6, dated Aug. 25, 2022, 4 pages (with English translation).
US Notice of Allowance in U.S. Appl. No. 16/563,738, dated Aug. 31, 2022, 5 pages.
US Notice of Allowance in U.S. Appl. No. 16/988,427, dated Aug. 26, 2022, 9 pages.
CN Office Action in Chinese Application No. 201880039828.4, dated Mar. 1, 2023, 19 pages (with English translation).
JP Notice of Allowance in Japanese Application No. 2018-536892, dated Mar. 29, 2023, 4 pages (with English translation).
JP Office Action in Japanese Application No. 2019-569226, dated Mar. 20, 2023, 5 pages (with English translation).
Altschul S.F., et al., "Basic Local Alignment Search Tool," Journal Molecular Biology, 1990, vol. 215, pp. 403-410.
Altschul S.F., et al., "Gapped BLAST and PSI-BLAST: A New Generation of Protein Database Search Programs," Nucleic Acids Research, Jul. 1997, vol. 25, No. 17, pp. 3389-3402.

(56) References Cited

OTHER PUBLICATIONS

Ausubel F.M., et al., "Short Protocols in Molecular Biology: A Compendium of Methods from Current Protocols in Molecular Biology," Wiley, John & Sons, Inc., 1995, 1 Page.
Berge et al., "Pharmaceutical Salts" Jan. 1977, Journal of Pharmaceutical Sciences, 66(1):1-19.
Coligan J.E., et al., "Current Protocols in Protein Science," Short Protocols in Protein Science, 1996, vol. 24, No. 409, 1 Page.
Deveraux J., et al., "A Comprehensive Set of Sequence Analysis Programs for the VAX," Nucleic Acids Research, 1984, vol. 12, No. 1, pp. 387-395.
Gagniuc P., et al., "Eukaryotic Genomes May Exhibit up to 10 Generic Classes of Gene Promoters," BMC Genomics, 2012, vol. 13, 17 Pages, DOI:10.1186/1471-2164-13-512, XP021134695.
Gennaro A.R., "Remington's Pharmaceutical Sciences," 17th edition, Mack Publishing Company, Easton, Pa., Oct. 1985, vol. 74, No. 10, pp. 1143-1144.
Harlow E., et al., "Antibodies: A Laboratory Manual," Cold Spring Harbor Laboratory Press, 1988, 1 Page.
Myers E.W., et al., "Optimal Alignments in Linear Space," CABIOS, 1988, vol. 4, No. 1, pp. 11-17.
Needleman et al. "A General Method Applicable to the Search for Similarities in the Amino Acid Sequence of Two Proteins" Mar. 28, 1970, J. Molecular Biology 48(3):443-453.
Notice of Reasons for Refusal for Japanese Patent Application No. 2021-045605, dated Apr. 1, 2022, 5 Pages. (with English translation).
Office Action for Chinese Patent Application No. 201780017712.6, dated Nov. 3, 2021, 16 Pages. (with English translation).
Office Action for European Patent Application No. 17739028.3, mailed May 22, 2023, 125 pages.
Pauza C.D., et al., "γδ T cells in HIV Disease: Past, Present, and Future," Frontiers in Immunology, Jan. 30, 2015, vol. 5, No. 687, 12 Pages.
Pauza C.D., et al., "Evolution and Function of the TCR Vgamma9 Chain Repertoire: It's Good to be Public," Cell Immunology, Jul. 2015, vol. 296, No. 1, pp. 22-30.
Pearson et al. "Improved Tools for Biological Sequence Comparison" Apr. 1988, Proceedings of the National Academy of Sciences of the United States of America 85(8):2444-2448.
Roden C., et al., "Novel Determinants of Mammalian Primary microRNA Processing Revealed by Systematic Evaluation of Hairpin-Containing Transcripts and Human Genetic Variation," Cold Spring Harbor Laboratory Press, 2017, vol. 27, pp. 374-384, ISSN 1088-9051/17, Retrieved from URL: www.genome.org.
Sambrook J., et al., "Molecular Cloning: A Laboratory Manual," 3rd edition, Cold Spring Harbor Laboratory Press, 2000, 2272 Pages.
Selbach M., et al., "Widespread Changes in Protein Synthesis Induced by MicroRNAs," Nature, Sep. 4, 2008, vol. 455, pp. 58-63, DOI:10.1038/nature07228.
Smith T.F., et al., "Comparison of Biosequences," Advances in Applied Mathematics, 1981, vol. 2, pp. 482-489.
Ye Y., et al., "Knockdown of Farnesylpyrophosphate Synthase Prevents Angiotensin II-Medicated Cardiac Hypertrophy," The International Journal of Biochemistry & Cell Biology, 2010, vol. 42, pp. 2056-2064.

VECTOR SYSTEM FOR EXPRESSING REGULATORY RNA

CROSS-REFERENCE TO RELATED APPLICATIONS

This application is a continuation of U.S. application Ser. No. 17/289,653, filed on Apr. 28, 2021 entitled "VECTOR SYSTEM FOR EXPRESSING REGULATORY RNA," which is a U.S. national phase filing under 35 U.S.C. § 371 of PCT/US2019/059828 filed on Nov. 5, 2019, entitled "VECTOR SYSTEM FOR EXPRESSING REGULATORY RNA," which claims priority to U.S. Provisional Patent Application No. 62/755,985 filed on Nov. 5, 2018 entitled "VECTOR SYSTEM FOR EXPRESSING REGULATORY RNA," the disclosures of which are incorporated herein by reference.

SEQUENCE LISTING

The Sequence Listing that was submitted in this application is incorporated herein by reference. The text file of the Sequence Listing is named 436313003417_SL.txt and the file size is 60,439 bytes. The text file is submitted electronically herewith.

FIELD

The present disclosure relates generally to the field of gene therapy, specifically in relation to the use of vectors and modified cells that encode or express regulatory RNA.

BACKGROUND

Malignant or neoplastic cells may be controlled by regulatory RNA and especially inhibitory RNA (RNAi) capable of blocking critical mechanisms of cell growth. In part, because they produce RNAi, Mesenchymal Stem Cells (MSC) are used increasingly for cellular therapies and are envisioned as cellular delivery vehicles for cancer treatment. MSC also produce immune-inhibiting cytokines including TGF-β and have a short half-life in vivo, making them good candidates for allogeneic cell therapy. Further, MSC express genes of the Connexin family that create a plasma membrane pore capable of interacting with connexin pores on tumor cell membranes. These pores allow exchange of cytoplasmic materials including RNAi, and may be exploited to deliver growth-inhibiting RNAi into tumor cells. MSC therapy is used currently for regenerative medicine and to combat autoimmune or inflammatory diseases.

SUMMARY

In an aspect, a viral vector is provided comprising a first nucleotide sequence encoding a small RNA capable of binding a non-coding region of a host copy of KIF11.

In embodiments, the non-coding region of the host copy of KIF11 is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the viral vector further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof.

In another aspect, a lentiviral particle produced by a packaging cell and capable of infecting a target cell is provided, wherein the lentiviral particle comprises an envelope protein capable of infecting the target cell; and a first nucleotide sequence encoding a small RNA capable of binding a non-coding region of a host copy of KIF11.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the lentiviral particle further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof. In embodiments, the target cell is a mesenchymal stem cell.

In another aspect, a modified mesenchymal stem cell is provided comprising a mesenchymal stem cell infected with a lentiviral particle, wherein the lentiviral particle comprises: an envelope protein capable of infecting the mesenchymal stem cell; and a first nucleotide sequence encoding a small RNA capable of binding a non-coding region of a host copy of KIF11.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the lentiviral particle further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof.

In another aspect, a method of producing a modified mesenchymal stem cell is provided, the method comprising: infecting a mesenchymal stem cell with an effective amount of a lentiviral particle, wherein the lentiviral particle comprises: an envelope protein capable of infecting the mesenchymal stem cell; and a first nucleotide sequence encoding a small RNA capable of binding a non-coding region of a host copy of KIF11.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the lentiviral particle further comprises a second nucleotide sequence encoding a KIF11 gene or a variant thereof, wherein the KIF11 gene or the variant thereof lacks at least one sequence portion. In embodiments, the sequence portion comprises a coding region or a non-coding region of the KIF11 gene or variant thereof. Where the sequence portion comprises a non-coding region, the sequence portion may comprise at least one of a 5' untranslated region or a 3' untranslated region of the KIF11 gene or variant thereof.

In another aspect, a method of treating cancer in a subject is provided. The method comprises administering a therapeutically-effective amount of any modified mesenchymal stem cell described herein to the subject. In embodiments, the modified mesenchymal stem cell is allogeneic to the subject. In embodiments, the modified mesenchymal stem cell is autologous to the subject. In embodiments, the cancer is selected from any one or more of a carcinoma, a sarcoma, a myeloma, a lymphoma, a mixed type, or a mixture of the foregoing.

In another aspect a use of the modified mesenchymal stem cell to treat cancer is provided comprising any of the modified mesenchymal stem cells described herein.

In another aspect, a method of treating cancer in a subject is provided, the method comprising administering a therapeutically effective amount of any lentiviral particle described herein to the subject.

In embodiments, the cancer is selected from any one or more of a carcinoma, a sarcoma, a myeloma, a lymphoma, a mixed type, or a mixture of the foregoing. In embodiments, the lentiviral particle is administered to the subject via an infected target cell. In embodiments, the target cell comprises a somatic cell. In embodiments, the somatic cell comprises a hepatocyte or a lymphocyte. In embodiments, the somatic cell comprises a lymphocyte, wherein the lymphocyte comprises a tumor specific T cell. In embodiments, the target cell comprises a stem cell. In embodiments, the stem cell comprises an induced pluripotent stem cell or a mesenchymal stem cell.

DETAILED DESCRIPTION

Overview of the Disclosure

Figure 1:
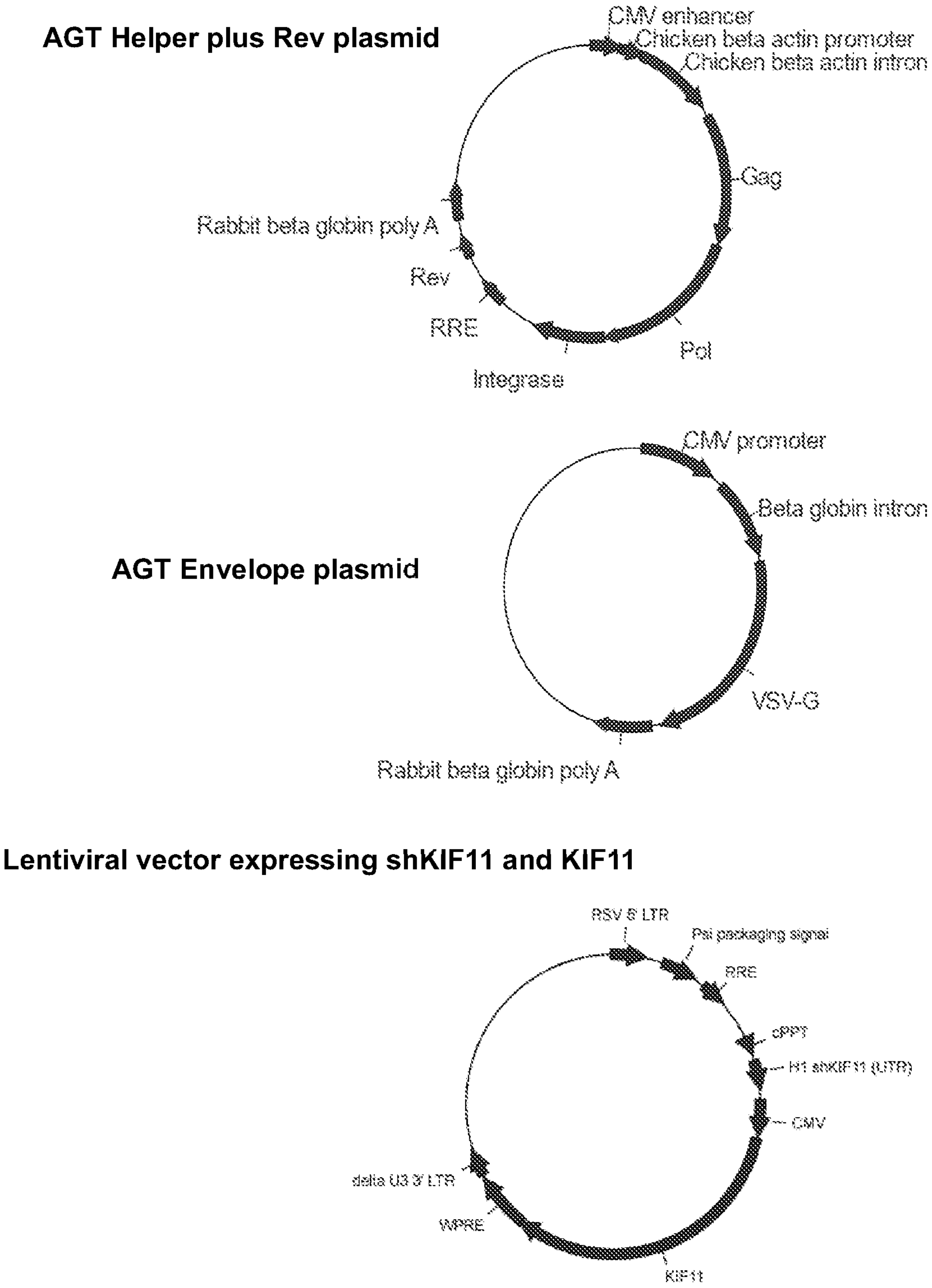
FIG. 1 depicts an exemplary 3-vector lentiviral vector system, in a circularized form.

In an aspect, this disclosure relates to vectors and modified cells that encode or express a small RNA capable of binding to a host cell copy of KIF11. In embodiments, the vectors are viral vectors. In embodiments, the modified cells are modified mesenchymal stem cells.

In another aspect, this disclosure relates to vectors and modified cells that encode or express: (i) a small RNA capable of binding a host copy of KIF11; and (ii) a modified KIF11 that is resistant to the small RNA. In embodiments, the vectors are viral vectors. In embodiments, the modified cells are mesenchymal stem cells.

In another aspect, this disclosure relates to vectors and modified cells that encode or express: (i) a small RNA capable of binding a host copy of KIF11; and (ii) an exogenous KIF11 gene that is resistant to the small RNA. In embodiments, the vectors are viral vectors. In embodiments, the modified cells are mesenchymal cells. In embodiments, the small RNA is capable of binding a non-coding region of a host copy of KIF11, for example, in the 5' UTR or in the 3' UTR. In embodiments, the exogenous KIF11 gene lacks at least a portion of a target sequence (e.g., a sequence portion thereof). In such embodiments, the exogenous KIF11 is resistant to activity by the small RNA, for example, to the ability of the small RNA to bind the exogenous KIF11. In such embodiments, the ability of the small RNA to modulate expression of the exogenous KIF11 is decreased and/or prevented.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used in the description and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The terms "administration of" or "administering" an active agent should be understood to mean providing an active agent to the subject in need of treatment in a form that can be introduced into that individual's body in a therapeutically useful form and therapeutically effective amount.

As used herein, the term "allogeneic" refers to a treatment in which the donor cells or tissues used in the treatment are not derived from the subject that is being treated with the donor cells or tissues. Accordingly, a treatment that is "allogeneic to the subject" refers to a treatment in which the donor cells or tissues do not derive from the subject.

As used herein, the term "autologous" refers to a treatment in which the donor cells or tissues used in the treatment are derived from the subject that is being treated with the donor cells or tissues. Accordingly, a treatment that is "autologous to the subject," refers to a treatment in which the donor cells or tissues derive from the subject.

As used herein, the term "complementary" refers to the capacity of two (2) nucleotide sequences to hybridize to each other through hydrogen bonding of one or more purines with one or more pyrimidines between the two (2) nucleotide sequences. Adenine (a purine) has the capacity of hydrogen bonding to both thymine (a pyrimidine) and uracil (a pyrimidine). Guanine (a purine) has the capacity of hydrogen bonding to cytosine (a pyrimidine). The term "complementary" includes two nucleotide sequences that are perfectly "complementary" in which each nucleobase on one nucleotide sequence is hydrogen bonded to its counterpart nucleobase on the other nucleotide sequence. The term "complementary" includes two nucleotide sequences that are imperfectly "complementary" in which at least one nucleobase on one nucleotide sequence is not hydrogen bonded to its counterpart nucleobase on the other nucleotide sequence. Imperfect "complementary" occurs when a nucleobase on one of the nucleotide sequences does not have the capacity to hydrogen bond to its counterpart nucleobase on the other nucleotide sequence. For example, when the counterpart to adenine on one of the nucleotide sequences is guanine or, for example, when the counterpart to uracil on one of the nucleotide sequences is cytosine. Two nucleotide sequences that are "complementary" may include a nucleotide sequence of a small RNA that is "complementary" to a nucleotide sequence of a mRNA. The nucleotide sequence of the small RNA may be perfectly "complementary" or imperfectly "complementary" to the nucleotide sequence of the mRNA.

As used herein, the term "comprising" is intended to mean that the compositions and methods include the recited elements, but does not exclude other elements. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this disclosure. Accordingly, it is intended that the methods and compositions can include additional steps and components (comprising) or alternatively including steps and compositions of no significance (consisting essentially of) or alternatively, intending only the stated method steps or compositions (consisting of).

As used herein, "expression," "expressed," or "encodes" refers to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The terms "individual," "subject," and "patient" are used interchangeably herein, and refer to any individual mammal subject, e.g., murine, porcine, bovine, canine, feline, equine, non-human primate or human primate.

The term "KIF11" refers to the gene Kinesin family member 11, also known as Kinesin-5. KIF11 functions in mitosis through interacting with the mitotic spindle. The term KIF11 includes all wild-type and variant KIF11 sequences, including both nucleotide and peptide sequences. Without limitation, the term KIF11 includes reference to SEQ ID NO: 4, and further includes variants having at least about 80% identity therewith.

The term "miRNA" refers to a microRNA, and also may be referred to herein as "miR".

The term "non-coding sequence" or "non-coding region" refers to the portion of a gene that does not code for a protein. The term without limitation refers to 5' untranslated sequences or regions of the gene, 3' untranslated sequences or regions of the gene, and introns of the gene.

The term "packaging cell line" refers to any cell line that can be used to express a lentiviral particle.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules provided in the disclosure. BLAST protein searches can be performed with the XBLAST program, score=50, wordlength=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, generally through pathways that result in the destruction of the target gene mRNA.

As used herein, a "target cell" is any cell that contains a surface molecule, such as a cell surface receptor, to which a biochemical agent, such as a vector or plasmid, is capable of binding. Upon interaction between the surface molecule and the biochemical agent, the "target cell" is capable of uptake of the biochemical agent by means of, for example, transduction. Uptake of the biochemical agent may result in modification to the genotype, the phenotype, or both the genotype and the phenotype of the "target cell."

As used herein, the term "target sequence" refers to a sequence portion on a gene or variant thereof that is complementary to a nucleic acid such as a small RNA. A "target sequence" may include a sequence portion on a coding region of a gene. Alternatively, a "target sequence" may include a sequence portion on a non-coding region of a gene such as a 3' UTR or a 5' UTR. For example, a "target sequence" may include a sequence portion on the 3' UTR or the 5' UTR of the KIF11 gene.

The term "therapeutically effective amount" refers to a sufficient quantity of the active agents of the present disclosure, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" includes, without limitation, any suitable viral vector, including an integrating vector or a non-integrating vector. In certain embodiments, a lentiviral vector or an AAV vector is used. In certain embodiments, a retrovirus, a measles virus, a mumps virus, an arenavirus, a picornavirus, a herpesvirus, or a poxvirus is used. Additionally, as used herein with reference to the lentiviral vector system, the term "vector" is synonymous with "plasmid". For example, the 3-vector and 4-vector systems, which include the 2-vector and 3-vector packaging systems, can also be referred to as 3-plasmid and 4-plasmid systems.

"A treatment" is intended to target the disease state and combat it, i.e., ameliorate or prevent the disease state. The particular treatment thus will depend on the disease state to be targeted and the current or future state of medicinal therapies and therapeutic approaches. A treatment may have associated toxicities.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

As used herein, the term "UTR" or "untranslated region" is in reference to a region of a gene that is 5' or 3' of the coding region of a gene.

As used herein, the term "3' UTR" or "3' untranslated region" is the "UTR" or "untranslated region" that is 3' of the coding region of a gene.

As used herein, the term "5' UTR" or "5' untranslated region" is the "UTR" or "untranslated region" that is 5' of the coding region of a gene.

As used herein, the term "variant" may also be referred to herein as analog or variation. A variant refers to any substitution, deletion, or addition to a nucleotide sequence.

Description of Aspects and Embodiments of the Disclosure

In an aspect, a viral vector is provided comprising a first nucleotide sequence encoding a small RNA capable of binding a non-coding region of a host copy of KIF11.

In an aspect, viral vector particles described herein are derived from viruses. In embodiments, the virus is any of a measles virus, a picornavirus, a mumps virus, an arenavirus or any other virus described herein. In embodiments, the virus encodes small RNA comprising any one or more of a miRNA, a siRNA, a dsRNA, a shRNA, a ribozyme, and a piRNA.

In an aspect, viral vector particles described herein are derived from retroviruses. In embodiments, the retrovirus is a HIV virus. In embodiments, the retrovirus is any retrovirus described herein. In embodiments, the retrovirus encodes small RNA comprising any one or more of a miRNA, a siRNA, a shRNA, a ribozyme, and a piRNA.

In embodiments, the non-coding region is a 3' untranslated region or a 5' untranslated region of the host copy of KIF11. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the viral vector further comprises a second nucleotide sequence encoding a KIF11 gene or a variant thereof, wherein the KIF11 gene or the variant thereof lacks at least one sequence portion. In embodiments, the sequence portion is in a non-coding region of the KIF11 gene. In embodiments, the non-coding region of the KIF11 gene is in at least one of a 5' untranslated region or a 3' untranslated region.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In embodiments, the KIF11 gene or variant thereof lacks more than one defined target sequence, for example, the KIF11 gene or variant thereof lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene or variant thereof lacks more than 10 defined target sequences.

In another aspect, a lentiviral particle produced by a packaging cell and capable of infecting a target cell is provided, the lentiviral particle comprising: an envelope protein capable of infecting the target cell; and a first nucleotide sequence encoding a small RNA capable of binding a non-coding region of a host copy of KIF11.

In embodiments, the lentiviral particle further comprises a Gag protein. In embodiments, the lentiviral particle further comprises a Pol protein.

In embodiments, the non-coding region is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the lentiviral particle further comprises a second nucleotide sequence encoding a KIF11 gene or a variant thereof, wherein the KIF11 gene or the variant thereof lacks at least one sequence portion. In embodiments, the sequence portion is in a non-coding region of the KIF11 gene. In embodiments, the non-coding region of the KIF11 gene is in at least one of the 5' untranslated region or the 3' untranslated region. In embodiments, the target cell is a mesenchymal stem cell.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In embodiments, the KIF11 gene or variant thereof lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene or variant thereof lacks more than 10 defined target sequences.

In another aspect, a modified mesenchymal stem cell is provided comprising a mesenchymal stem cell infected with a lentiviral particle, wherein the lentiviral particle comprises: an envelope protein capable of infecting the mesenchymal stem cell; and a first nucleotide sequence encoding a small RNA capable of binding a non-coding region of a host copy of KIF11.

In embodiments, the lentiviral particle further comprises a Gag protein. In embodiments, the lentiviral particle further comprises a Pol protein.

In embodiments, the non-coding region is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the nucleotide sequence encoding the small RNA is present at 1 copy per cell, 2 copies per cell, 3 copies per cell, 4 copies per cell, 5 copies per cell, 6 copies per cell, 7 copies per cell, 8 copies per cell, 9 copies per cell, or 10 copies per cell. In embodiments, the nucleotide sequence encoding the small RNA is present between about 10 and about 20 copies per cell.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In another aspect, a method of producing a modified mesenchymal stem cell is provided, the method comprising: infecting a mesenchymal stem cell with an effective amount of a lentiviral particle, wherein the lentiviral particle comprises: an envelope protein capable of infecting the mesenchymal stem cell; and a first nucleotide sequence encoding a small RNA capable of binding at least one complementary region in a non-coding region of a host copy of KIF11.

In embodiments, the lentiviral particle further comprises a Gag protein. In embodiments, the lentiviral particle further comprises a Pol protein.

In embodiments, the non-coding region is a 3' untranslated region or a 5' untranslated region. In embodiments, the small RNA comprises a sequence having at least 80% sequence identity with at least one of SEQ ID NO: 1, SEQ ID NO: 2, or SEQ ID NO: 3. In embodiments, the small RNA comprises at least one of SEQ ID NO: 1, SEQ ID NO: 2, or SEQ ID NO: 3. In embodiments, the first nucleotide sequence is present in the modified mesenchymal stem cell at between about 1 and about 10 copies per cell.

In embodiments, the nucleotide sequence encoding the small RNA is present at 1 copy per cell, 2 copies per cell, 3 copies per cell, 4 copies per cell, 5 copies per cell, 6 copies per cell, 7 copies per cell, 8 copies per cell, 9 copies per cell, or 10 copies per cell. In embodiments, the nucleotide sequence encoding the small RNA is present between about 10 and about 20 copies per cell.

In embodiments, the small RNA is a shRNA. In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the small RNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2 or SEQ ID NO: 3.

In embodiments, the KIF11 gene or variant thereof lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene or variant thereof lacks more than 10 defined target sequence.

In another aspect, a method of treating cancer in a subject is provided, the method comprising administering a therapeutically-effective amount of any modified mesenchymal stem cell described herein to the subject.

In embodiments, the modified mesenchymal stem cell is allogeneic to the subject. In embodiments, the modified mesenchymal stem cell is autologous to the subject.

In embodiments, the cancer is selected from any one or more of a carcinoma, a sarcoma, a myeloma, a lymphoma, a mixed type, or a mixture of the foregoing. In embodiments, the cancer is any cancer described herein.

In another aspect, a use of the modified mesenchymal stem cell to treat cancer is provided comprising any of the modified mesenchymal stem cells described herein.

In another aspect, a method of treating cancer in a subject is provided, the method comprising administering a therapeutically effective amount of any lentiviral particle described herein to the subject.

In embodiments, the cancer is selected from any one or more of a carcinoma, a sarcoma, a myeloma, a lymphoma, a mixed type, or a mixture of the foregoing.

In embodiments, the lentiviral particle is administered to the subject via an infected target cell. In embodiments, the target cell comprises a somatic cell. In embodiments the somatic cell comprises a bone cell, a cartilage cell, a nerve cell, an epithelial cell, a muscle cell, a blood cell, a conductive cell, a connective cell, a glandular cell, or a supportive cell.

In embodiments, the somatic cell comprises a hepatocyte.

In embodiments, the somatic cell comprises a lymphocyte. In embodiments, the lymphocyte comprises a B cell. In embodiments, the lymphocyte comprises a T cell. In embodiments, the T cell comprises a tumor specific T cell.

In embodiments, the target cell comprises a stem cell. In embodiments, the stem cell comprises an embryonic stem cell. In embodiments, the stem cell comprises a somatic stem cell. In embodiments, the stem cell comprises an induced pluripotent stem cell. In embodiments, the stem cell comprises a mesenchymal stem cell.

In another aspect, a viral vector is provided, the viral vector comprises: (i) an encoded KIF11 gene comprising a coding region, and at least one of a 5' untranslated region and a 3' untranslated region, wherein the KIF11 gene lacks at least one defined target sequence in at least one of the 5' untranslated region or the 3' untranslated region, and (ii) a small RNA capable of binding at least one complementary region in a non-coding region of a host copy of KIF11, wherein expression of the encoded KIF11 gene is resistant to activity by the small RNA.

In embodiments, the KIF11 gene lacks at least one defined target sequence in the 5' untranslated region. In embodiments, the KIF11 gene lacks at least one defined target sequence in the 3' untranslated region. In embodiments, the KIF11 gene lacks at least one defined target sequence in both the 5' and 3' untranslated regions.

In embodiments, the KIF11 gene lacks more than one defined target sequences, for example, the KIF11 gene lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene lacks more than 10 defined target sequences.

In embodiments, the KIF11 gene comprises a variant in a portion of its non-coding region relative to a host copy of KIF11. In embodiments, the variant comprises a substitution in the nucleotide sequence of KIF11. In embodiments, the variant comprises a deletion in the nucleotide sequence of KIF11. In embodiments, the variant comprises an addition to the nucleotide sequence of KIF11. In embodiments, the variant is in the 3' untranslated region of the KIF11 gene. In embodiments, the variant is in the 5' untranslated region of the KIF11 gene. In embodiments, the variant causes the KIF11 gene to lack at least one target sequence (e.g., a sequence portion thereof).

In embodiments, the KIF11 gene or variant thereof comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with SEQ ID NO: 4.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the small RNA targets a sequence not present in the gene expression construct of the same lentivirus vector to avoid the possibility of intragenic recombination of the vector or plasmids encoding vector components. In embodiments, the small RNA targets a sequence not present in the gene expression construct of the same lentivirus vector, when the protein coding region differs by a small number of mutations.

In embodiments, a small number of mutations is less than 20 mutations. In embodiments, a small number of mutations is less than 15 mutations. In embodiments, a small number of mutations is less than 10 mutations. In embodiments, a small number of mutations is less than 5 mutations. In embodiments, a small number of mutations is 4 mutations. In embodiments, a small number of mutations is 3 mutations. In embodiments, a small number of mutations is 2 mutations. In embodiments, a small number of mutations is 1 mutation.

In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In embodiments, the viral vector is a lentiviral vector. In embodiments, the viral vector is an AAV vector.

In another aspect, a lentiviral particle produced by a packaging cell is provided. In embodiments the lentiviral particle is produced in the 293T/17 HEK packaging cell line. In embodiments, the lentiviral particle is produced in any cell known in the art that is capable of producing a lentiviral particle.

In embodiments, the lentiviral particle comprises an envelope protein capable of infecting target cells. In embodiments, the lentiviral particle comprises (i) a KIF11 gene comprising a coding region, and at least one of a 5' untranslated region and a 3' untranslated region, wherein the KIF11 gene sequence lacks at least one defined target sequence in at least one of the 5' untranslated region or the 3' untranslated region; and (ii) a small RNA capable of binding to at least one complementary region in a non-coding region of a host copy of KIF11, wherein the KIF11 gene in the lentiviral particle is resistant to activity by the small RNA.

In embodiments, the KIF11 gene in the lentiviral particle lacks at least one defined target sequence in the 5' untranslated region. In embodiments, the KIF11 gene in the lentiviral particle lacks at least one defined target sequence in the 3' untranslated region. In embodiments, the KIF11 gene in the lentiviral particle lacks at least one defined target sequence in both the 5' and 3' untranslated regions.

In embodiments, the KIF11 gene in the lentiviral particle lacks more than one defined target sequence, for example, the KIF11 gene in the lentiviral particle lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene in the lentiviral particle lacks more than 10 defined target sequences.

In embodiments, the KIF11 gene in the lentiviral particle comprises a variant in a portion of its non-coding sequence relative to a host copy of the KIF11 gene. In embodiments, the variant comprises a substitution in the non-coding sequence of KIF11. In embodiments, the variant comprises a deletion in the non-coding sequence of KIF11. In embodiments, the variant comprises an addition to the non-coding sequence of KIF11. In embodiments, the variant is in the 3' untranslated region of the KIF11 gene in the lentiviral particle. In embodiments, the variant is in the 5' untranslated region of the KIF11 gene in the lentiviral particle. In embodiments, the variant causes the KIF11 gene to lack at least one target sequence (e.g., a sequence portion thereof).

In embodiments, the KIF11 gene in the lentiviral particle or variant thereof comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with SEQ ID NO: 4.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, or SEQ ID NO: 3.

In embodiments, the small RNA is a siRNA. In embodiments, the small RNA is a microRNA. In embodiments, the small RNA is a dsRNA. In embodiments, the small RNA is a piRNA. In embodiments, the small RNA is a ribozyme.

In another aspect, a method of treating a cancer in a subject using an immunotherapy-based composition is provided. In embodiments, the method comprises administering or having administered a therapeutically-effective amount of the immunotherapy-based composition to the subject.

In embodiments, the immunotherapy-based composition comprises a modified cell. In embodiments, the modified cell is a modified mesenchymal stem cell.

In embodiments, the immunotherapy-based composition further comprises a lentiviral particle, that comprises: (i) an envelope protein capable of infecting a cancer cell; (ii) a KIF11 gene comprising a coding region, and at least one of a 5' untranslated region and a 3' untranslated region, wherein the KIF11 gene lacks at least one defined target sequence in at least one of the 5' untranslated region and the 3' untranslated region; and (iii) a small RNA capable of binding at least one complementary region in a non-coding region of a host copy of a KIF11 gene, wherein the KIF11 gene in the lentiviral particle is resistant to activity by the small RNA.

In embodiments, the KIF11 gene in the lentiviral particle lacks at least one defined target sequence in the 5' untranslated region. In embodiments, the KIF11 gene in the lentiviral particle lacks at least one defined target sequence in the 3' untranslated region. In embodiments, the KIF11 gene in the lentiviral particle lacks at least one defined target sequence in both the 5' and 3' untranslated regions.

In embodiments, the KIF11 gene in the lentiviral particle lacks more than one defined target sequence, for example, the KIF11 gene in the lentiviral particle lacks 2 defined target sequences, lacks 3 defined target sequences, lacks 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene in the lentiviral particle lacks more than 10 defined target sequences.

In embodiments, the KIF11 gene in the lentiviral particle comprises a variant in a portion of its non-coding sequence relative to a host copy of KIF11. In embodiments, the variant comprises a substitution in the nucleotide sequence of KIF11. In embodiments, the variant comprises a deletion in the nucleotide sequence of KIF11. In embodiments, the variant comprises an addition to the nucleotide sequence of KIF11. In embodiments, the variant is in the 3' untranslated region of the first nucleotide sequence. In embodiments, the variant is in the 5' untranslated region of the first nucleotide sequence. In embodiments, the variant causes the KIF11 gene to lack at least one target sequence (e.g., a sequence portion thereof).

In embodiments, the KIF11 gene in the lentiviral particle comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with SEQ ID NO: 4.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the small RNA is a microRNA. In embodiments, the small RNA is a siRNA. In embodiments, the small RNA is a dsRNA. In embodiments, the small RNA is a piRNA. In embodiments, the small RNA is a ribozyme.

In another aspect, a modified cell is provided comprising a coding region of a KIF11 gene, wherein the KIF11 gene lacks at least one defined target sequence in at least one of a 5' untranslated region or a 3' untranslated region. In embodiments, the modified cell expresses a small RNA capable of binding to at least one complementary region in a non-coding region of a host copy of the KIF11 gene.

In embodiments, the modified cell is a modified cell of any cell known in the art. In embodiments, the modified cell is a modified bone cell. In embodiments, the modified cell is a modified cartilage cell. In embodiments, the modified cell is a modified nerve cell. In embodiments, the modified cell is a modified epithelial cell. In embodiments, the modified cell is a modified muscle cell. In embodiments, the modified cell is a modified blood cell. In embodiments, the modified cell is a modified conductive cell. In embodiments, the modified cell is a modified connective cell. In embodiments, the modified cell is a modified glandular cell. In embodiments, the modified cell is a modified supportive cell.

In embodiments, the modified cell is a modified mesenchymal stem cell.

In embodiments, the modified cell is cultured such that it expands and/or proliferates to create a seed stock of cells that can be used in therapy.

In embodiments, the modified cell or seed stock is used to treat a cancer. In embodiments, the modified cell or seed stock is used to treat any of the cancers described herein.

In embodiments, the modified cell or seed stock is used to treat a tumor. In embodiments, the tumor is a solid tumor. In embodiments, the tumor is a benign tumor. In embodiments, the tumor is a metastatic tumor. In embodiments, the tumor is a fluid-filled tumor.

In embodiments, the modified cell or seed stock is used to treat a cell or group of cells that is different from the modified cell or seed stock.

In embodiments, the modified cell or seed stock is used in a cell therapy. In embodiments, the cell therapy is an allogeneic cell therapy. In embodiments, the cell therapy is an autologous cell therapy.

In embodiments, the KIF11 gene exogenously expressed in the modified cell lacks at least one defined target sequence in a 5' untranslated region. In embodiments, the KIF11 gene exogenously expressed in the modified cell lacks at least one defined target sequence in a 3' untranslated region. In embodiments, the KIF11 gene exogenously expressed in the modified cell lacks at least one defined target sequence in both the 5' and 3' untranslated regions.

In embodiments, the KIF11 gene exogenously expressed in the modified cell lacks more than one defined target sequence in its untranslated region(s), for example, lacks 2 defined target sequences, lacks 3 defined target sequences, lack 4 defined target sequences, lacks 5 defined target sequences, lacks 6 defined target sequences, lacks 7 defined target sequences, lacks 8 defined target sequences, lacks 9 defined target sequences, or lacks 10 defined target sequences. In embodiments, the KIF11 gene exogenously expressed in the modified cell lacks more than 10 defined target sequences.

In embodiments, the KIF11 gene exogenously expressed in the modified cell comprises a variant in a portion of its non-coding sequence relative to a host copy of the KIF11 gene. In embodiments, the variant comprises a substitution in the nucleotide sequence of KIF11. In embodiments, the variant comprises a deletion in the nucleotide sequence of KIF11. In embodiments, the variant comprises an addition to the nucleotide sequence of KIF11. In embodiments, the variant is in a 3' untranslated region of the KIF11 gene exogenously expressed in the modified cell. In embodiments, the variant is in a 5' untranslated region of the KIF11 gene exogenously expressed in the modified cell. In embodiments, the variant causes the KIF11 gene to lack at least one target sequence (e.g., a sequence portion thereof).

In embodiments, KIF11 gene exogenously expressed in the modified cell comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% identity with SEQ ID NO: 4.

In embodiments, the regulatory RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the small RNA is a siRNA. In embodiments, the small RNA is a microRNA. In embodiments, the small RNA is a dsRNA. In embodiments, the small RNA is a piRNA. In embodiments, the small RNA is a ribozyme.

In embodiments, the small RNA inhibits expression of a host copy of the KIF11 gene through binding the 3' untranslated region of the gene.

In embodiments, the small RNA is delivered to cancer cells as part of a cell therapy. In embodiments, the cell therapy is an autologous cell therapy. In embodiments, the cell therapy is an allogeneic cell therapy.

In embodiments, the cancer cells are any type of cancer cells known in the art. In embodiments, the cancer cells are derived from any cancer described herein.

In embodiments, the small RNA results in reduction in KIF11 mRNA expression relative to control treatments. In embodiments, the reduction in KIF11 mRNA expression is 1% or greater relative to control treatments, for example, greater than 5%, greater than 10%, greater than 15%, greater than 20%, greater than 20%, greater than 25%, greater than 30%, greater than 35%, greater than 40%, greater than 45%, greater than 50%, greater than 55%, greater than 60%, greater than 70%, greater than 75%, greater than 80%, greater than 85%, greater than 90%, or greater than 95%.

In embodiments, reduction in KIF11 mRNA expression results in reduction of cell number relative to control treatments. In embodiments, the cell number is reduced by more than 1%, more than 5%, more than 10%, more than 15%, more than 20%, more than 25%, more than 30%, more than 35%, more than 40%, more than 45%, more than 50%, more than 55%, more than 60%, more than 65%, more than 70%, more than 75%, more than 80%, more than 85%, more than 90%, or more than 95%.

In another aspect, a lentiviral vector is provided that co-expresses (i) a small RNA and (ii) a KIF11 gene. In embodiments, the small RNA targets a host copy of the KIF11 gene and the KIF11 gene expressed by the lentiviral vector is resistant to the small RNA. In embodiments, the KIF11 gene expressed by the lentiviral vector is truncated. In embodiments, the truncation is at the 3' untranslated region. In embodiments, the truncation is at the 5' untranslated region. In embodiments the KIF11 gene expressed by the lentiviral vector is mutated. In embodiments, the mutation is in the 3' untranslated region. In embodiments, the mutation is in the 5' untranslated region.

In embodiments, the small RNA is a shRNA. In embodiments, the shRNA comprises a sequence having at least 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with at least one of SEQ ID NO: 1, SEQ ID NO: 2, and SEQ ID NO: 3.

In embodiments, the lentiviral vector is delivered to cancer cells as part of cell therapy. In embodiments, the cancer cells are any cancer cells known in the art. In embodiments, the cell therapy is an allogeneic cell therapy. In embodiments, the cell therapy is an autologous cell therapy.

In embodiments, the KIF11 gene has at least one variant in its 3' untranslated region relative to a host copy of the KIF11 gene. In embodiments, the variant comprises a substitution in the nucleotide sequence of the KIF11 gene. In embodiments, the variant comprises a deletion in the nucleotide sequence of the KIF11 gene. In embodiments, the variant comprises an addition to the nucleotide sequence of the KIF11 gene.

In embodiments, the vector system that carries the genetic material is a 2-component vector system. In embodiments, the vector system that carries the genetic material is a 3-component vector system.

In another aspect, modified mesenchymal stem cells are provided. In embodiments, the modified mesenchymal stem cells produce inhibitory RNA against KIF11. In embodiments, the modified mesenchymal stem cells retain their growth capacity through exogenous expression of KIF11. In embodiments, the KIF11 that is exogenously expressed lacks a non-coding sequence that can be targeted by the small RNA.

In embodiments, the mesenchymal stems are genetically modified using a 2-component lentivirus vector system. In embodiments, the 2-component lentivirus vector system delivers inhibitory RNA that targets KIF11. In embodiments, the 2-component lentivirus vector system delivers an exogenous KIF11 gene.

In embodiments, the modified mesenchymal cells have special properties that allow engaging in cell-to-cell contact with tumor cells. In embodiments, the cell-to-cell contact allows for delivery of small RNA that target KIF11 to cancer cells via a portal formed by connexin proteins.

Cancer

The compositions and methods provided herein are used to treat cancer. A cell, tissue, or target may be a cancer cell, a cancerous tissue, harbor cancerous tissue, or be a subject or patient diagnosed or at risk of developing a disease or condition. In certain aspects, a cell may be an epithelial, an endothelial, a mesothelial, a glial, a stromal, or a mucosal cell. The cancer cell population can include, but is not limited to a brain, a neuronal, a blood, an endometrial, a meninges, an esophageal, a lung, a cardiovascular, a liver, a lymphoid, a breast, a bone, a connective tissue, a fat, a retinal, a thyroid, a glandular, an adrenal, a pancreatic, a stomach, an intestinal, a kidney, a bladder, a colon, a prostate, a uterine, an ovarian, a cervical, a testicular, a splenic, a skin, a smooth muscle, a cardiac muscle, or a striated muscle cell, can also include a cancer cell population from any of the foregoing, and can be associated with one or more of carcinomas, sarcomas, myelomas, lymphomas, mixed types or mixtures of the foregoing. In still a further aspect cancer includes, but is not limited to astrocytoma, acute myeloid anaplastic large cell lymphoma, angiosarcoma, B-cell lymphoma, Burkitt's lymphoma, breast carcinoma, bladder carcinoma, carcinoma of the head and neck, cervical carcinoma, colorectal carcinoma, endometrial carcinoma, esophageal squamous cell carcinoma, Ewing's sarcoma, fibrosarcoma, glioma, glioblastoma, gastrinoma, gastric carcinoma, hepatoblastoma, hepatocellular carcinoma, Kaposi's sarcoma, Hodgkin lymphoma, laryngeal squamous cell carcinoma, larynx carcinoma, leiomyosarcoma, lipoma, liposarcoma, melanoma, mantle cell lymphoma, medulloblastoma, mesothelioma, myxofibrosarcoma, mucosa-associated lymphoid tissue B cell lymphoma, multiple myeloma, high-risk myelodysplastic syndrome, nasopharyngeal carcinoma, neuroblastoma, neurofibroma, high-grade non-Hodgkin lymphoma, non-Hodgkin lymphoma, lung carcinoma, non-small cell lung carcinoma, ovarian carcinoma, oesophageal carcinoma, osteosarcoma, pancreatic carcinoma, pheochromocytoma, prostate carcinoma, renal cell carcinoma, retinoblastoma, rhabdomyosarcoma, salivary gland tumor, Schwannoma, small cell lung cancer, squamous cell carcinoma of the head and neck, testicular tumor, thyroid carcinoma, urothelial carcinoma, and Wilm's tumor.

The compositions and methods provided herein are also used to treat NSCLC (non-small cell lung cancer), pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases.

Genetic Medicines

Genetic medicine includes reference to viral vectors that are used to deliver genetic constructs to host cells for the purposes of disease therapy or prevention. Genetic medicines include cell therapies in which cells have been modified through delivery of the genetic constructs to the cells.

Genetic constructs can include, but are not limited to, functional genes or portions of genes to correct or complement existing defects, DNA sequences encoding regulatory proteins, DNA sequences encoding regulatory RNA molecules including antisense, short homology RNA, long noncoding RNA, small interfering RNA or others, and decoy sequences encoding either RNA or proteins designed to compete for critical cellular factors to alter a disease state. Genetic constructs include constructs that encode or express regulatory sequences that are capable of knocking down gene expression. Genetic medicine involves delivering these therapeutic genetic constructs either directly or through cell therapies to target cells to provide treatment or alleviation of a particular disease.

Therapeutic Vectors

A lentiviral virion (particle) in accordance with various aspects and embodiments herein is expressed by a vector system encoding the necessary viral proteins to produce a virion (viral particle). In various embodiments, one vector containing a nucleic acid sequence encoding the lentiviral Pol proteins is provided for reverse transcription and integration, operably linked to a promoter. In another embodiment, the pol proteins are expressed by multiple vectors. In other embodiments, vectors containing a nucleic acid sequence encoding the lentiviral Gag proteins for forming a viral capsid, operably linked to a promoter, are provided. In embodiments, this gag nucleic acid sequence is on a separate vector than at least some of the pol nucleic acid sequence. In other embodiments, the gag nucleic acid is on a separate vector from all the pol nucleic acid sequences that encode pol proteins.

Numerous modifications can be made to the vectors herein, which are used to create the particles to further minimize the chance of obtaining wild type revertants. These include, but are not limited to, deletions of the U3 region of the LTR, tat deletions and matrix (MA) deletions. In embodiments, the gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment, the envelope protein is not from a lentivirus, but from a different virus. In such instances, the resultant particle is referred to as a pseudotyped particle. By appropriate selection of envelopes one can "infect" virtually any cell. For example, one can use an env gene that encodes an envelope protein that targets an endocytic compartment. Examples of viruses from which such env genes and envelope proteins can be derived from include the influenza virus (e.g., the Influenza A virus, Influenza B virus, Influenza C virus, Influenza D virus, Isavirus, Quaranjavirus, and Thogotovirus), the Vesiculovirus (e.g., Indiana vesiculovirus), alpha viruses (e.g., the Semliki forest virus, Sindbis virus, Aura virus, Barmah Forest virus, Bebaru virus, Cabassou virus, Getah virus, Highlands J virus, Trocara virus, Una Virus, Ndumu virus, and Middleburg virus, among others), arenaviruses (e.g., the lymphocytic choriomeningitis virus, Machupo virus, Junin virus and Lassa Fever virus), flaviviruses (e.g., the tick-borne encephalitis virus, Dengue virus, hepatitis C virus, GB virus, Apoi virus, Bagaza virus, Edge Hill virus, Jugra virus, Kadam virus, Dakar bat virus, Modoc virus, Powassan virus, Usutu virus, and Sal Vieja virus, among others), rhabdoviruses (e.g., vesicular stomatitis virus, rabies virus), paramyxoviruses (e.g., mumps or measles) and orthomyxoviruses (e.g., influenza virus).

Other envelope proteins that can preferably be used include those derived from endogenous retroviruses (e.g., feline endogenous retroviruses and baboon endogenous retroviruses) and closely related gammaretroviruses (e.g., the Moloney Leukemia Virus, MLV-E, MLV-A, Gibbon Ape Leukemia Virus, GALV, Feline leukemia virus, Koala retrovirus, Trager duck spleen necrosis virus, Viper retrovirus, Chick syncytial virus, Gardner-Arnstein feline sarcoma virus, and Porcine type-C oncovirus, among others). These gammaretroviruses can be used as sources of env genes and envelope proteins for targeting primary cells. The gammaretroviruses are particularly preferred where the host cell is a primary cell.

Envelope proteins can be selected to target a specific desired host cell. For example, targeting specific receptors such as a dopamine receptor can be used for brain delivery. Another target can be vascular endothelium. These cells can be targeted using an envelope protein derived from any virus in the Filoviridae family (e.g., Cuevaviruses, Dianloviruses, Ebolaviruses, and Marburgviruses). Species of Ebolaviruses include Tai Forest ebolavirus, Zaire ebolavirus, Sudan ebolavirus, Bundibugyo ebolavirus, and Reston ebolavirus.

In addition, in embodiments, glycoproteins can undergo post-transcriptional modifications. For example, in an embodiment, the GP of Ebola, can be modified after translation to become the GP1 and GP2 glycoproteins. In another embodiment, one can use different lentiviral capsids with a pseudotyped envelope (e.g., FIV or SHIV [U.S. Pat. No. 5,654,195]). A SHIV pseudotyped vector can readily be used in animal models such as monkeys.

Lentiviral vector systems as provided herein typically include at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 1). In another embodiment, the gag and pol genes are provided on a first plasmid and the rev gene is provided on a second plasmid (e.g., FIG. 2). Accordingly, both 3-vector and 4-vector systems can be used to produce a lentivirus as described herein. In embodiments, the therapeutic vector, at least one envelope plasmid and at least one helper plasmid are transfected into a packaging cell, for example a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of KIF11 and/or inhibiting the expression of endogenous KIF11.

Figure 2:
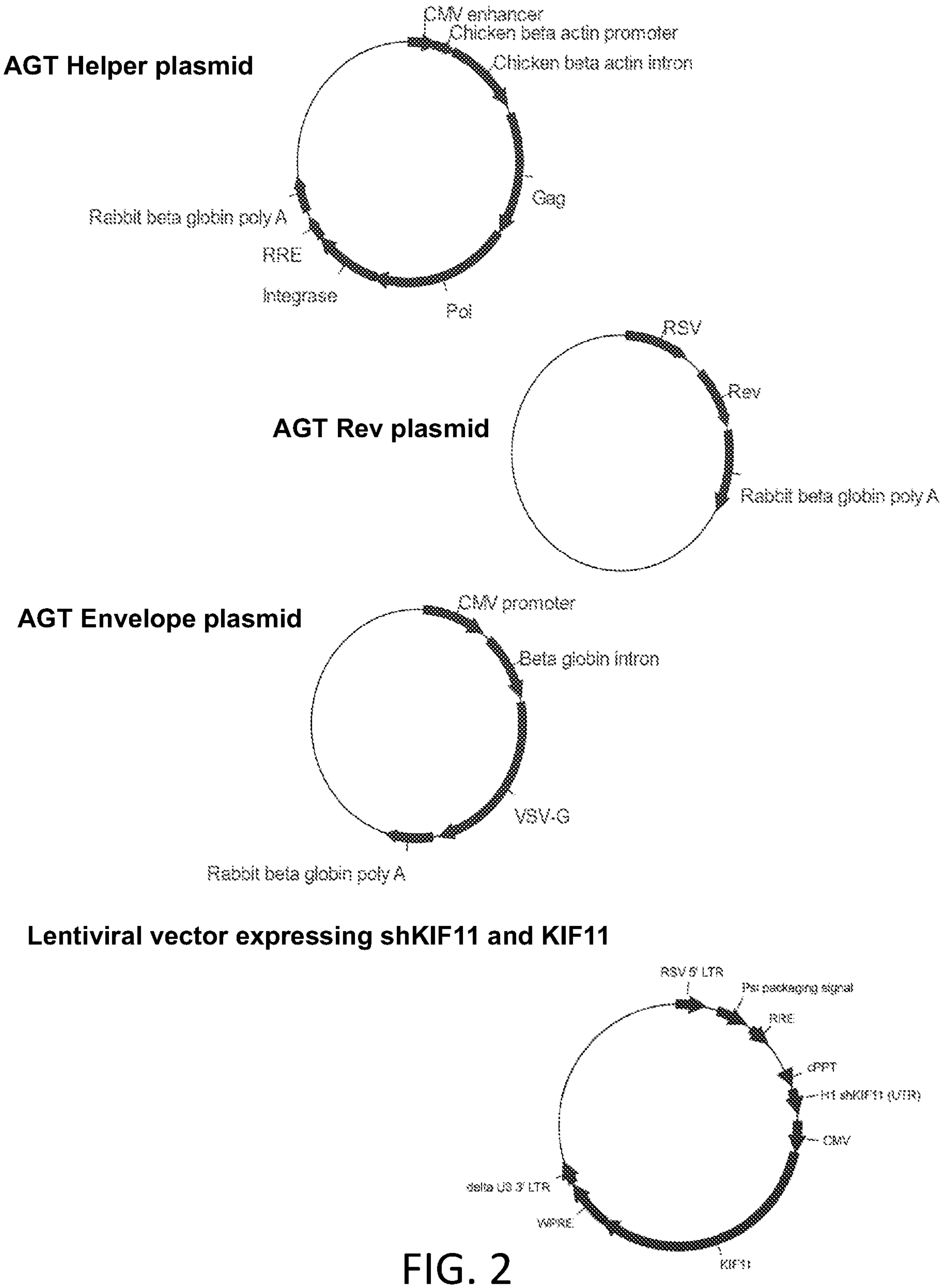
FIG. 2 depicts an exemplary 4-vector lentiviral vector system, in a circularized form.

In another aspect, and as detailed in FIG. 1 and FIG. 2, the lentiviral vector, which is also referred to herein as a therapeutic vector, can include the following elements: hybrid 5' long terminal repeat (RSV/5' LTR) (SEQ ID NO: 5 and SEQ ID NO: 6), Psi sequence (RNA packaging site) (SEQ ID NO: 7), RRE (Rev-response element) (SEQ ID NO: 8), cPPT (polypurine tract) (SEQ ID NO: 9), H1 promoter (SEQ ID NO: 10), KIF11 shRNA (SEQ ID NO: 1, SEQ ID NO: 2, or SEQ ID NO: 3), Woodchuck Post-Transcriptional Regulatory Element (WPRE) (SEQ ID NO: 11), and 3' Delta LTR (SEQ ID NO: 12). In another aspect, sequence variation, by way of substitution, deletion, addition, or mutation can be used to modify the sequences references herein.

In another aspect, the lentiviral vector, which is also referred to herein as a therapeutic vector, can include the following elements: 5' long terminal repeat, RRE (Rev-response element), cPPT (polypurine tract), H1 promoter, KIF11 shRNA, CMV promoter, transferrin receptor transmembrane region fused with IgG1 Fc, Woodchuck Post-Transcriptional Regulatory Element (WPRE), and 3' Delta LTR.

In another aspect, a helper plasmid has been designed to include the following elements: CAG promoter (SEQ ID NO: 13); HIV component gag (SEQ ID NO: 14); HIV component pol (SEQ ID NO: 15); HIV Int (SEQ ID NO: 16); HIV RRE (SEQ ID NO: 17); and HIV Rev (SEQ ID NO: 18).

In another aspect, a helper plasmid has been designed to include the following elements: CMV enhancer, chicken beta actin promoter, rabbit beta globin intron, HIV component gag; HIV component pol; HIV Int; HIV RRE; HIV Rev, and rabbit beta globin poly A.

In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, the plasmids used for lentiviral packaging can be modified with similar elements and the intron sequences could potentially be removed without loss of vector function. For example, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from human endogenous retroviruses including HERV-W, baboon endogenous retrovirus BaEV, feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Of note, lentiviral packaging systems can be acquired commercially (e.g., Lenti-vpak packaging kit from OriGene Technologies, Inc., Rockville, Md.), and can also be designed as described herein. Moreover, it is within the skill of a person skilled in the art to substitute or modify aspects of a lentiviral packaging system to improve any number of relevant factors, including the production efficiency of a lentiviral particle.

In another aspect, adeno-associated viral (AAV) vectors can also be used.

AAV Vector Construction. KIF11 sequence (SEQ ID NO: 4) or KIF11 shRNA sequence (e.g., SEQ ID NO: 1, SEQ ID NO: 2, or SEQ ID NO: 3) can be inserted into the pAAV plasmid (Cell Biolabs). KIF11 oligonucleotide sequences containing BamHI and EcoRI restriction sites are synthesized by Eurofins MWG Operon. Overlapping sense and antisense oligonucleotide sequences are mixed and annealed during cooling from 70 degrees Celsius to room temperature. The pAAV are digested with the restriction enzymes BamHI and EcoRI for one hour at 37 degrees Celsius. The digested pAAV plasmid are purified by agarose gel electrophoresis and extracted from the gel using a DNA gel extraction kit from Thermo Scientific. The DNA concentrations are determined and vector to oligo (3:1 ratio) are mixed, allowed to anneal, and ligated. The ligation reaction is performed with T4 DNA ligase for 30 minutes at room temperature. 2.5 microliters of the ligation mix are added to 25 microliters of STBL3 competent bacterial cells. Transformation is achieved after heat-shock at 42 degrees Celsius. Bacterial cells are spread on agar plates containing ampicillin and drug-resistant colonies (indicating the presence of ampicillin-resistance plasmids) are recovered and expanded in LB broth. To check for insertion of the oligo sequences, plasmid DNA is extracted from harvested bacteria cultures with the Thermo Scientific DNA mini prep kit. Insertion of shRNA sequences in the pAAV plasmid is verified by DNA sequencing using a specific primer for the promoter used to regulate shRNA expression.

Production of AAV particles. The AAV-KIF11 shRNA plasmid is combined with the plasmids pAAV-RC2 (Cell Biolabs) and pHelper (Cell Biolabs). The pAAV-RC2 plasmid contains the Rep and AAV2 capsid genes and pHelper contains the adenovirus E2A, E4, and VA genes. To produce AAV particles, these plasmids are transfected in the ratio 1:1:1 (pAAV-shKIF11: pAAV-RC2: pHelper) into 293T cells. For transfection of cells in 150 mm dishes (BD Falcon), 10 micrograms of each plasmid are added together in 1 ml of DMEM. In another tube, 60 microliters of the transfection reagent PEI (1 microgram/ml) (Polysciences) is added to 1 ml of DMEM. The two tubes are mixed together and allowed to incubate for 15 minutes. Then the transfection mixture is added to cells and the cells are collected after 3 days. The cells are lysed by freeze/thaw lysis in dry ice/isopropanol. Benzonase nuclease (Sigma) is added to the cell lysate for 30 minutes at 37 degrees Celsius. Cell debris is then pelleted by centrifugation at 4 degrees Celsius for 15 minutes at 12,000 rpm. The supernatant is collected and then added to target cells.

Dosage and Dosage Forms

Mesenchymal Stem Cells

In embodiments, the vector compositions can be administered to mesenchymal stem cells (MSCs). MSCs can be isolated from multiple sources including the bone marrow, the placenta, and the umbilical cord. Subsequent to isolation, MSCs are genetically modified and expanded to create a seed stock. The seed stock can then be used in an autologous or allogeneic cell therapy. Methods of isolation of MSCs, expansion of MSCs, and administration of MSCs are described below.

Isolation and expansion of MSCs: Numerous methods are known in the art for isolating and expanding MSCs. In embodiments, MSCs are isolated from placentas, which are recovered after elective cesarean section delivery for full-term newborns. The placenta is washed in phosphate buffered saline (PBS) and the maternal decidua is removed. Tissue portions of approximately 1 $cm^3$ or 4 grams wet weight are dissected from the fetal interfacing chorionic villous. Tissue portions are washed again in PBS and treated at 37° C. with 1 mg/ml Collagenase A solution for 60 minutes. Digested material is collected by centrifugation and resuspended in a trypsin/EDTA solution for 10 minutes at 37° C. Trypsin-treated material is collected again by centrifugation, washed once, resuspended in Bio-AMF-1 medium (Biological Industries, Israel) with 1% penicillin-streptomycin solution plus 5 mM L-Glutamine. Cells were transferred to T-25 culture flasks and incubated in a humidified atmosphere at 37° C. with 5% $CO_2$. When MSC reach confluence in the T-25 flask, they are treated with trypsin/EDTA to release cells bound to plastic, diluted with medium and re-plated in new T-25 flasks.

Other methods of isolating and expanding MSCs that are known in the art can be used. Detailed protocols for isolating and expanding MSCs are described in the following references, which are incorporated herein by reference in their entirety: (i) Huang Q, Yang Y, Luo C, Wen Y, Liu R, Li S, Chen T, Sun H, and Tang L. 2019. *An efficient protocol to generate placental chorionic plate-derived mesenchymal stem cells with superior proliferative and immunomodulatory properties*. Stem Cell Research & Therapy 10:301. (ii) Hassan G, Kasem I, Antaki, R, Mohammad M B, AlKadry R, and Aljamali M. 2019. *Isolation of umbilical cord mesenchymal stem cells using blood derivatives accompanied with explant method*. Stem Cell Investigation 6:29.

Identifying phenotypes of MSCs: The MSC phenotype varies according to tissue of origin. For chorionic villous MSCs the major phenotypic markers of cell identity include: CD44, CD73, CD105, CD90, alpha-SMA, and Stro-1. Antibody staining and flow cytometry to detect these cell surface markers will confirm the presence of MSC and further indicate the fraction of cells most similar to chorionic villous MSC. Specific patterns of gene expression have also been identified for MSCs. Chorionic villous MSCs express SOX-2 but not NANOG or POU5F1. Expression of all three of these genes is a common marker for embryonic stem cell pluripotency; expression limited to SOX-2 is consistent with the partially pluripotent phenotype of MSC.

Production of lentivirus vectors: Lentivirus vectors are produced from packaging cells that were transfected with 3 (for laboratory purposes) or 4 (for clinical use) plasmids encoding virion enzyme and structural proteins, the envelope glycoprotein, and the therapeutic transgene. Typically, the envelope glycoprotein is glycoprotein G from Vesicular Stomatitis Virus. Typical lentivirus vectors complemented with VSV-G are suitable for MSC transduction and stable genetic modification.

Lentivirus vector genetic modification of MSCs: Several approaches to genetic modification of MSCs are known in the art. Lentivirus vectors are the preferred method for stable genetic modification of MSC and have been evaluated in short-term and long-term cultures of bone marrow-derived and other types of MSC. Creating lentivirus vectors expressing both marker proteins (green or red fluorescence proteins) and puromycin acetyltransferase (confers resistance to puromycin) allow for drug selection of genetically modified MSC, which appear identical to unmodified MSC after a battery of tests for phenotypic changes, altered cell mobility, or capacity for cell amplification in long-term culture.

Lentivirus vector particle transduction can be performed in three steps:

Step 1: confluent MSCs are trypsinized, diluted 1:3 and replated for 2 days.

Step 2: Lentivirus vector stock in PBS plus 8 ug/mL Polybrene is overlayed on the MSC cell monolayer for 4 hours then removed by rinsing cells with medium.

Step 3: MSCs are cultured for a defined period of time. The period of time may be less than one day, one day, or more than one day, as appropriate.

Step 4: MSCs are detached from the plate with trypsin solution and used for DNA, RNA, or protein extraction that will measure the efficiency of transduction.

For most lentivirus vectors, transduction with multiplicity of infection equal to 5 results in >80% of MSCs becoming genetically modified. The modifications are stable and transgene expression persists for many generations.

For large scale manufacturing of gene modified MSCs for clinical use, a seed stock containing 10-50 million transduced MSCs are enlarged through serial passage and adapted to suspension culture. The final cell culture volume may reach 100 to 200 L, with cell yields approaching $5\times10^9$ per liter. Cells are recovered by centrifugation and/or filtration, washed and resuspended in medium for in vivo administration. Large scale expansion of MSCs can be performed in suspension cultures of up to 200 L under GMP conditions.

Administration of Cell Compositions (Cell Therapy)

Genetic modification and expansion of MSCs results in the creation of seed stock that can then be used as part of a cell therapy. Subjects may be administered an allogeneic or autologous cell therapy.

The cell therapy may be administered periodically, such as once or twice a day, or any other suitable time period. For example, cell compositions may be administered to a subject in need once a week, once every other week, once every three weeks, once a month, every other month, every three months, every six months, every nine months, once a year, every eighteen months, every two years, every thirty months, or every three years.

In embodiments, the cell compositions are administered as a pharmaceutical composition. In embodiments, the pharmaceutical composition can be formulated in a wide variety of dosage forms, including but not limited to nasal, pulmonary, oral, topical, or parenteral dosage forms for clinical application. Each of the dosage forms can comprise various solubilizing agents, disintegrating agents, surfactants, fillers, thickeners, binders, diluents such as wetting agents or other pharmaceutically acceptable excipients. The pharmaceutical composition can also be formulated for injection, insufflation, infusion, or intradermal exposure. For instance, an injectable formulation may comprise the cell compositions in an aqueous or non-aqueous solution at a suitable pH and tonicity.

The cell compositions may be administered to a subject via direct injection into a tumor site or at a site of infection.

In embodiments, the cell compositions can be administered systemically. In embodiments, the cell compositions can be administered via guided cannulation to tissues immediately surrounding the sites of tumor or infection.

The cell compositions can be administered using any pharmaceutically acceptable method, such as intranasal, buccal, sublingual, oral, rectal, ocular, parenteral (intravenously, intradermally, intramuscularly, subcutaneously, intraperitoneally), pulmonary, intravaginal, locally administered, topically administered, topically administered after scarification, mucosally administered, via an aerosol, in semi-solid media such as agarose or gelatin, or via a buccal or nasal spray formulation.

Further, the cell compositions can be formulated into any pharmaceutically acceptable dosage form, such as capsule, liquid dispersion, gel, aerosol, pulmonary aerosol, nasal aerosol, ointment, cream, semi-solid dosage form, a solution, an emulsion, and a suspension. Further, the pharmaceutical composition may be a transdermal delivery system.

In embodiments, the pharmaceutical composition can be formulated as a sublingual or buccal dosage form. Such dosage forms comprise sublingual tablets or aolution compositions that are administered under the tongue.

In embodiments, the pharmaceutical composition can be formulated as a nasal dosage form. Such dosage forms comprise solution, suspension, and gel compositions for nasal delivery.

In embodiments, the pharmaceutical composition can be formulated in a liquid dosage form for oral administration, such as suspensions, emulsions or syrups. In embodiments, the liquid dosage form can include, in addition to commonly used simple diluents such as water and liquid paraffin, various excipients such as humectants, sweeteners, aromatics or preservatives. In embodiments, the pharmaceutical composition can be formulated to be suitable for administration to a pediatric patient.

In embodiments, the pharmaceutical composition can be formulated in a dosage form for parenteral administration, such as sterile aqueous solutions, suspensions, emulsions, non-aqueous solutions or suppositories.

The dosage of the pharmaceutical composition can vary depending on the patient's weight, age, gender, administration time and mode, excretion rate, and the severity of disease.

In embodiments, the treatment of cancer is accomplished by guided direct injection of the cell compositions into tumors, using needle, or intravascular cannulation. In embodiments, the cell compositions are administered into the cerebrospinal fluid, blood or lymphatic circulation by venous or arterial cannulation or injection, intradermal delivery, intramuscular delivery or injection into a draining organ near the site of disease.

EXAMPLES

The following examples are given to illustrate aspects of the present embodiments. It should be understood, however, that the embodiments are not to be limited to the specific conditions or details described in these examples. All printed publications referenced herein are specifically incorporated by reference.

Example 1: Development of a Lentiviral Vector System

A lentiviral vector system was developed as summarized in FIG. 1 and FIG. 2 (circularized form). Lentiviral particles can be produced in 293T/17 HEK cells (purchased from American Type Culture Collection, Manassas, Va.) following transfection with the therapeutic vector, the envelope plasmid, and the helper plasmid. The transfection of 293T/17 HEK cells, will produce functional viral particles, will use the reagent Poly(ethylenimine) (PEI) to increase the efficiency of plasmid DNA uptake. The plasmids and DNA are initially added separately in culture medium without serum in a ratio of 3:1 (mass ratio of PEI to DNA). After 2-3 days, cell medium is collected, and lentiviral particles are purified by high-speed centrifugation and/or filtration followed by anion-exchange chromatography. The concentration of lentiviral particles can be expressed in terms of transducing units/ml (TU/ml). The determination of TU is accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-plasmid system (i.e., a 2-plasmid lentiviral packaging system) was designed to produce lentiviral particles. A schematic of the 3-plasmid system is shown in FIG. 1 Briefly, and with reference to FIG. 1, the top-most vector is a helper plasmid, which, in this case, includes Rev; the vector appearing in the middle is the envelope plasmid; the bottom-most vector is the therapeutic vector, as described herein.

Referring more specifically to FIG. 1, the Helper plus Rev plasmid includes a CAG enhancer (SEQ ID NO: 19); a CAG promoter (SEQ ID NO: 13); a chicken beta actin intron (SEQ ID NO: 20); a HIV gag (SEQ ID NO: 14); a HIV Pol (SEQ ID NO: 15); a HIV Int (SEQ ID NO: 16); a HIV RRE (SEQ ID NO: 17); a HIV Rev (SEQ ID NO: 18); and a rabbit beta globin poly A (SEQ ID NO: 21). The Helper plus Rev plasmid includes a CMV enhancer; a chicken beta actin promoter; a rabbit beta globin intron; a HIV gag; a HIV Pol; a HIV Int; a HIV RRE; a HIV Rev; and a rabbit beta globin poly A.

The Envelope plasmid includes a CMV promoter (SEQ ID NO: 22); a beta globin intron (SEQ ID NO: 23); a VSV-G (SEQ ID NO: 24); and a rabbit beta globin poly A (SEQ ID NO: 25).

Synthesis of a 2-Vector Lentiviral Packaging System Including Helper (Plus Rev) and Envelope Plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAGGAAGAT-3') (SEQ ID NO: 44) and reverse primer was (5'-CCATACAATGAATGGACACTAGGCGGCCGCACGAAT-3') (SEQ ID NO: 45)

The sequence for the Gag, Pol, Integrase fragment was as follows:

```
                                         (SEQ ID NO: 26)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC
```

-continued

```
ATAATTGGAAGAAATCTGTTGACTCAGATTGGCTGCACTTTAAATTTTCC
CATTAGTCCTATTGAGACTGTACCAGTAAAATTAAAGCCAGGAATGGATG
GCCCAAAAGTTAAACAATGGCCATTGACAGAAGAAAAAATAAAAGCATTA
GTAGAAATTTGTACAGAAATGGAAAAGGAAGGAAAAATTTCAAAAATTGG
GCCTGAAAATCCATACAATACTCCAGTATTTGCCATAAAGAAAAAAGACA
GTACTAAATGGAGAAAATTAGTAGATTTCAGAGAACTTAATAAGAGAACT
CAAGATTTCTGGGAAGTTCAATTAGGAATACCACATCCTGCAGGGTTAAA
ACAGAAAAAATCAGTAACAGTACTGGATGTGGGCGATGCATATTTTTCAG
TTCCCTTAGATAAAGACTTCAGGAAGTATACTGCATTTACCATACCTAGT
ATAAACAATGAGACACCAGGGATTAGATATCAGTACAATGTGCTTCCACA
GGGATGGAAAGGATCACCAGCAATATTCCAGTGTAGCATGACAAAAATCT
TAGAGCCTTTTAGAAAACAAAATCCAGACATAGTCATCTATCAATACATG
GATGATTTGTATGTAGGATCTGACTTAGAAATAGGGCAGCATAGAACAAA
AATAGAGGAACTGAGACAACATCTGTTGAGGTGGGGATTTACCACACCAG
ACAAAAAACATCAGAAAGAACCTCCATTCCTTTGGATGGGTTATGAACTC
CATCCTGATAAATGGACAGTACAGCCTATAGTGCTGCCAGAAAAGGACAG
CTGGACTGTCAATGACATACAGAAATTAGTGGGAAAATTGAATTGGGCAA
GTCAGATTTATGCAGGGATTAAAGTAAGGCAATTATGTAAACTTCTTAGG
GGAACCAAAGCACTAACAGAAGTAGTACCACTAACAGAAGAAGCAGAGCT
AGAACTGGCAGAAAACAGGGAGATTCTAAAAGAACCGGTACATGGAGTGT
ATTATGACCCATCAAAAGACTTAATAGCAGAAATACAGAAGCAGGGGCAA
GGCCAATGGACATATCAAATTTATCAAGAGCCATTTAAAAATCTGAAAAC
AGGAAAGTATGCAAGAATGAAGGGTGCCCACACTAATGATGTGAAACAAT
TAACAGAGGCAGTACAAAAAATAGCCACAGAAAGCATAGTAATATGGGGA
AAGACTCCTAAATTTAAATTACCCATACAAAAGGAAACATGGGAAGCATG
GTGGACAGAGTATTGGCAAGCCACCTGGATTCCTGAGTGGGAGTTTGTCA
ATACCCCTCCCTTAGTGAAGTTATGGTACCAGTTAGAGAAAGAACCCATA
ATAGGAGCAGAAACTTTCTATGTAGATGGGGCAGCCAATAGGGAAACTAA
ATTAGGAAAAGCAGGATATGTAACTGACAGAGGAAGACAAAAAGTTGTCC
CCCTAACGGACACAACAAATCAGAAGACTGAGTTACAAGCAATTCATCTA
GCTTTGCAGGATTCGGGATTAGAAGTAAACATAGTGACAGACTCACAATA
TGCATTGGGAATCATTCAAGCACAACCAGATAAGAGTGAATCAGAGTTAG
TCAGTCAAATAATAGAGCAGTTAATAAAAAAGGAAAAAGTCTACCTGGCA
TGGGTACCAGCACACAAAGGAATTGGAGGAAATGAACAAGTAGATAAATT
GGTCAGTGCTGGAATCAGGAAAGTACTATTTTTAGATGGAATAGATAAGG
CCCAAGAAGAACATGAGAAATATCACAGTAATTGGAGAGCAATGGCTAGT
GATTTTAACCTACCACCTGTAGTAGCAAAAGAAATAGTAGCCAGCTGTGA
TAAATGTCAGCTAAAAGGGGAAGCCATGCATGGACAAGTAGACTGTAGCC
CAGGAATATGGCAGCTAGATTGTACACATTTAGAAGGAAAAGTTATCTTG
GTAGCAGTTCATGTAGCCAGTGGATATATAGAAGCAGAAGTAATTCCAGC
AGAGACAGGGCAAGAAACAGCATACTTCCTCTTAAAATTAGCAGGAAGAT
GGCCAGTAAAAACAGTACATACAGACAATGGCAGCAATTTCACCAGTACT
ACAGTTAAGGCCGCCTGTTGGTGGGCGGGGATCAAGCAGGAATTTGGCAT
TCCCTACAATCCCCAAAGTCAAGGAGTAATAGAATCTATGAATAAAGAAT
TAAAGAAAATTATAGGACAGGTAAGAGATCAGGCTGAACATCTTAAGACA
GCAGTACAAATGGCAGTATTCATCCACAATTTTAAAAGAAAAGGGGGGAT
TGGGGGGTACAGTGCAGGGGAAAGAATAGTAGACATAATAGCAACAGACA
TACAAACTAAAGAATTACAAAAACAAATTACAAAAATTCAAAATTTTCGG
GTTTATTACAGGGACAGCAGAGATCCAGTTTGGAAAGGACCAGCAAAGCT
CCTCTGGAAAGGTGAAGGGGCAGTAGTAATACAAGATAATAGTGACATAA
AAGTAGTGCCAAGAAGAAAAGCAAAGATCATCAGGGATTATGGAAAACAG
ATGGCAGGTGATGATTGTGTGGCAAGTAGACAGGATGAGGATTAA
```

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

```
                                                  (SEQ ID NO: 27)
TCTAGAATGGCAGGAAGAAGCGGAGACAGCGACGAAGAGCTCATCAGAAC
AGTCAGACTCATCAAGCTTCTCTATCAAAGCAACCCACCTCCCAATCCCG
AGGGGACCCGACAGGCCCGAAGGAATAGAAGAAGAAGGTGGAGAGAGAGA
CAGAGACAGATCCATTCGATTAGTGAACGGATCCTTGGCACTTATCTGGG
ACGATCTGCGGAGCCTGTGCCTCTTCAGCTACCACCGCTTGAGAGACTTA
CTCTTGATTGTAACGAGGATTGTGGAACTTCTGGGACGCAGGGGGTGGGA
AGCCCTCAAATATTGGTGGAATCTCCTACAATATTGGAGTCAGGAGCTAA
AGAATAGAGGAGCTTTGTTCCTTGGGTTCTTGGGAGCAGCAGGAAGCACT
ATGGGCGCAGCGTCAATGACGCTGACGGTACAGGCCAGACAATTATTGTC
TGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGA
ATCCTGGCTGTGGAAAGATACCTAAAGGATCAACAGCTCCTAGATCTTTT
TCCCTCTGCCAAAAATTATGGGGACATCATGAAGCCCCTTGAGCATCTGA
CTTCTGGCTAATAAAGGAAATTTATTTTCATTGCAATAGTGTGTTGGAAT
TTTTTGTGTCTCTCACTCGGAAGGACATATGGGAGGGCAAATCATTTAAA
ACATCAGAATGAGTATTTGGTTTAGAGTTTGGCAACATATGCCATATGCT
GGCTGCCATGAACAAAGGTGGCTATAAAGAGGTCATCAGTATATGAAACA
GCCCCCTGCTGTCCATTCCTTATTCCATAGAAAAGCCTTGACTTGAGGTT
AGATTTTTTTTATATTTTGTTTTGTGTTATTTTTTTCTTTAACATCCCTA
AAATTTTCCTTACATGTTTTACTAGCCAGATTTTTCCTCCTCTCCTGACT
ACTCCCAGTCATAGCTGTCCCTCTTCTCTTATGAAGATCCCTCGACCTGC
AGCCCAAGCTTGGCGTAATCATGGTCATAGCTGTTTCCTGTGTGAAATTG
TTATCCGCTCACAATTCCACACAACATACGAGCCGGAAGCATAAAGTGTA
```

-continued

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 28)

ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGGCGGGGGGGGGGGGGGCGCGCGCC

AGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGGAGCGGCTCGGGGGGTGCGTGCGTGTGTGTGTGCGT

GGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGC

CGGGGGCGGTGCCCCGCGGTGCGGGGGGGCTGCGAGGGGAACAAAGGCTG

CGTGCGGGGTGTGTGCGTGGGGGGGTGAGCAGGGGGTGTGGGCGCGGCGG

TCGGGCTGTAACCCCCCCCTGCACCCCCCTCCCCGAGTTGCTGAGCACGG

CCCGGCTTCGGGTGCGGGGCTCCGTGCGGGGCGTGGCGCGGGGCTCGCCG

TGCCGGGCGGGGGGTGGCGGCAGGTGGGGGTGCCGGGCGGGGCGGGGCCG

-continued

CCTCGGGCCGGGGAGGGCTCGGGGGAGGGGCGCGGCGGCCCCGGAGCGCC

GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTG

CGGCGCCGGCAGGAAGGAAATGGGCGGGGAGGGCCTTCGTGCGTCGCCGC

GCCGCCGTCCCCTTCTCCATCTCCAGCCTCGGGGCTGCCGCAGGGGGACG

GCTGCCTTCGGGGGGGACGGGGCAGGGCGGGGTTCGGCTTCTGGCGTGTG

ACCGGCGGGAATTC

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3.1 plasmid (Invitrogen) at the EcoRI restriction site and the correct orientation was determined by sequencing using a CMV specific primer. The DNA sequence was as follows:

(SEQ ID NO: 24)

GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT

CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

```
                                         -continued
AACTTCCTGATGATGAGAGTTTATTTTTTGGTGATACTGGGCTATCCAAA

AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC

TCCGAGTTGGTATCCATCTTTGCATTAAATTAAAGCACACCAAGAAAAGA

CAGATTTATACAGACATAGAGATGAGAATTC
```

A 4-vector system (i.e., a 3-vector lentiviral packaging system) has also been designed and produced using the methods and materials described herein. A schematic of the 4-vector system is shown in FIG. 2. Briefly, and with reference to FIG. 2, the top vector is a helper plasmid, which, in this case, does not include Rev; the vector that is second from the top is a separate Rev plasmid; the vector that is second from the bottom is the envelope plasmid; the bottom vector is the previously described therapeutic vector.

As shown in FIG. 1, the Helper plasmid includes a CAG enhancer (SEQ ID NO: 19); a CAG promoter (SEQ ID NO: 13); a chicken beta actin intron (SEQ ID NO: 20); a HIV gag (SEQ ID NO: 14); a HIV Pol (SEQ ID NO: 15); a HIV Int (SEQ ID NO: 16); a HIV RRE (SEQ ID NO: 17); and a rabbit beta globin poly A (SEQ ID NO: 21). The Helper plasmid includes a CMV enhancer; a chicken beta actin promoter; a rabbit beta globin intron; a HIV gag; a HIV Pol; a HIV Int; a HIV RRE; and a rabbit beta globin poly A.

As shown in FIG. 2, the Rev plasmid includes an RSV promoter (SEQ ID NO: 29); a HIV Rev (SEQ ID NO: 18); and a rabbit beta globin poly A (SEQ ID NO: 21).

As shown in FIG. 1 and FIG. 2, the Envelope plasmid includes a CMV promoter (SEQ ID NO: 22); a beta globin intron (SEQ ID NO: 23); a VSV-G (SEQ ID NO: 24); and a rabbit beta globin poly A (SEQ ID NO: 25).

Synthesis of a 3-Vector Lentiviral Packaging System Including Helper, Rev, and Envelope Plasmids.
Materials and Methods:
Construction of the Helper Plasmid without Rev:
The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

```
                                         (SEQ ID NO: 30)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA
```

```
                                         -continued
GATTTTTTTTATATTTTGTTTTGTGTTATTTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA

AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG
```

Construction of the Rev Plasmid:
The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

```
                                         (SEQ ID NO: 29)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGAGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA
```

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 31), phosphoglycerate kinase (PGK) (SEQ ID NO: 32), and ubiquitin C (UbC) (SEQ ID NO: 33) can replace the CMV (SEQ ID NO: 22) or CAG promoter (SEQ ID NO: 13). These sequences can also be further varied by addition, substitution, deletion or mutation.

Poly A sequences: SV40 poly A (SEQ ID NO: 34) and bGH poly A (SEQ ID NO: 35) can replace the rabbit beta globin poly A (SEQ ID NO: 21). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 14); HIV Pol (SEQ ID NO: 15); and HIV Int (SEQ ID NO: 16) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 36), gibbon ape leukemia virus (GALV) (SEQ ID NO: 37), Rabies (FUG) (SEQ ID NO: 38), lymphocytic choriomeningitis virus (LCMV) (SEQ ID NO: 39), influenza A fowl plague virus (FPV) (SEQ ID NO: 40), Ross River alphavirus (RRV) (SEQ ID NO: 41), murine leukemia virus 10A1 (MLV) (SEQ ID NO: 42), or Ebola virus (EboV) (SEQ ID NO: 43). Sequences for these envelopes are identified in the sequence table herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'δ LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2: Lentiviral Particle-Delivered shRNA-Based RNA Interference Targeting the Human KIF11 (Eg5) Untranslated Region Results in Significantly Reduced Levels of KIF11 mRNA PC3 human prostate carcinoma cells were infected with lentiviral vector particles containing the H1 promoter and either a non-targeting shRNA (used as a control) (SEQ ID NO: 56) or any one of three different KIF11 shRNA sequences: KIF11 shRNA sequence #1 (SEQ ID NO: 1); KIF11 shRNA sequence #2 (SEQ ID NO: 2); and KIF11 shRNA sequence #3 (SEQ ID NO: 3).

PC3 human prostate carcinoma cells were seeded in 24-well plates at $5\times10^4$ cells per well. After 24 hours, the cells were transduced at 5 MOI with lentiviral vector particles containing the H1 promoter and one of three different KIF11 UTR shRNA sequences (SEQ ID NO: 1, SEQ ID NO: 2, or SEQ ID NO: 3) or a lentiviral vector particle expressing only GFP. After 72 hours, RNA was extracted from the cells with the RNeasy kit (Qiagen) and converted to cDNA with SuperScript VILO (Thermo). Expression of KIF11 cDNA was determined by quantitative PCR using a FAM-labeled KIF11 TaqMan probe (SEQ ID NO: 48) and primers for KIF11 (forward primer (SEQ ID NO: 46); reverse primer (SEQ ID NO: 47)). KIF11 RNA expression was normalized to actin levels for each sample (Actin forward primer (SEQ ID NO: 49); Actin reverse primer #1 (SEQ ID NO: 50); Actin probe (SEQ ID NO: 52)).

Figure 5:
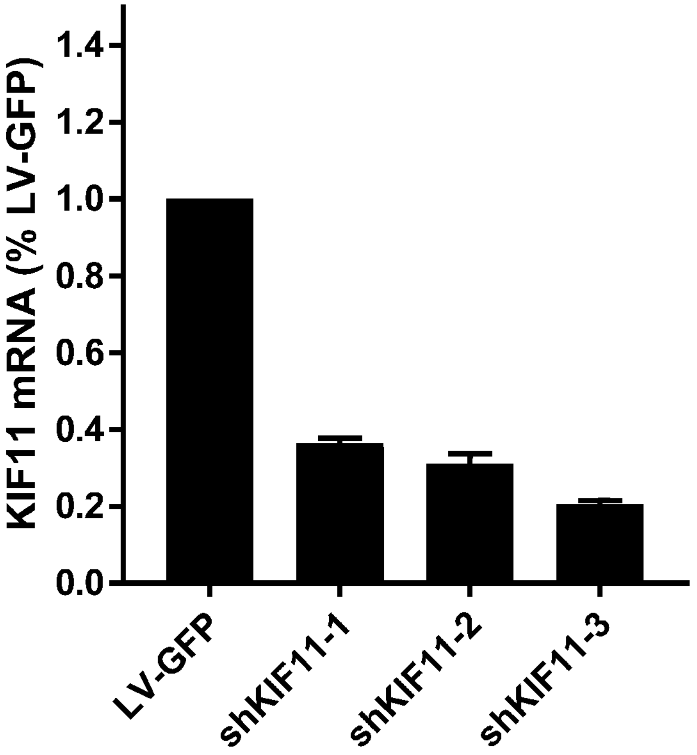
FIG. 5 depicts data demonstrating effect of lentiviral-delivered shRNA-based RNA interference that targets the human KIF11 untranslated region.

Levels of KIF11 mRNA relative to the % LV-GFP is shown in FIG. 5. As compared to LV-GFP transduced cells, KIF11 RNA: (i) decreased 63% using KIF11 shRNA sequence #1 (SEQ ID NO: 1) (see, bar showing KIF11 mRNA expression after transduction with shKIF11-1), (ii) decreased 69% using KIF11 shRNA sequence #2 (SEQ ID NO: 2) (see, bar showing KIF11 mRNA expression after transduction with shKIF11-2), and (iii) decreased 79% using KIF11 shRNA sequence #3 (SEQ ID NO: 3) (see, bar showing KIF11 mRNA expression after transduction with shKIF11-3).

Example 3: Lentiviral Particle-Delivered Co-Expression of Both (i) a shRNA-Based RNA Interference Targeting the Human KIF11 Untranslated Region and (ii) a KIF11 Coding Sequence, Results in High Expression Levels of KIF11

Figure 3:
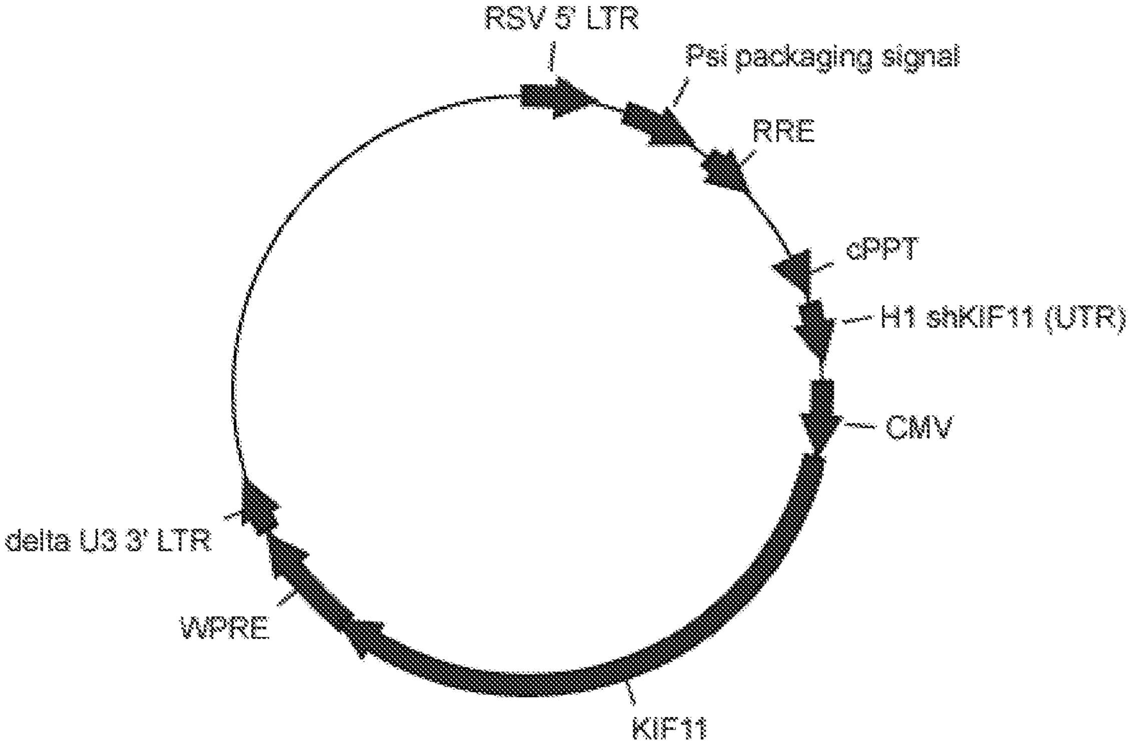
FIG. 3 depicts a lentiviral vector expressing KIF11 shRNA targeting sequence and the KIF11 coding sequence, in a circularized form.
Figure 4:
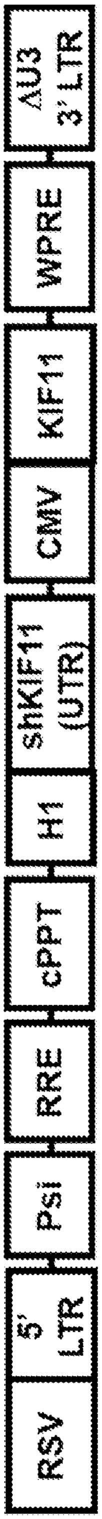
FIG. 4 depicts a linear map of a lentiviral vector expressing a KIF11 shRNA targeting sequence and a KIF11 coding sequence.

PC3 human prostate carcinoma cells were infected with a lentiviral vector particle containing the H1 promoter regulating the expression of KIF11 shRNA (KIF11 shRNA sequence #3 (SEQ ID NO: 3)) and a lentiviral vector particle containing both: (i) the H1 promoter regulating the expression of KIF11 shRNA (KIF11 shRNA sequence #3) (SEQ ID NO: 3)); and (ii) a CMV promoter regulating the expression of the KIF11 sequence comprising its coding sequence and a truncated 3'UTR (SEQ ID NO: 4). An embodiment of the vector used in this experiment is provided in FIG. 3 (circularized form) and FIG. 4 (linear form).

PC3 human prostate carcinoma cells were seeded in 24-well plates at $5\times10^4$ cells per well. After 24 hours, the cells were transduced at 5 MOI with a lentiviral vector particle expressing KIF11 UTR shRNA #3 (SEQ ID NO: 3) and a CMV promoter regulating the expression of the KIF11 coding sequence (SEQ ID NO: 4). After 72 hours, RNA was extracted from the cells with the RNeasy kit (Qiagen) and converted to cDNA with SuperScript VILO (Thermo). Expression of KIF11 cDNA was determined by quantitative PCR using a FAM-labeled KIF11 TaqMan probe (SEQ ID NO: 48) and primers for KIF11 (forward primer (SEQ ID NO: 46); reverse primer (SEQ ID NO: 47)). KIF11 expression was normalized to actin levels for each sample (Actin forward primer (SEQ ID NO: 49); Actin reverse primer #1 (SEQ ID NO: 50); and Actin probe (SEQ ID NO: 52)).

Figure 6:
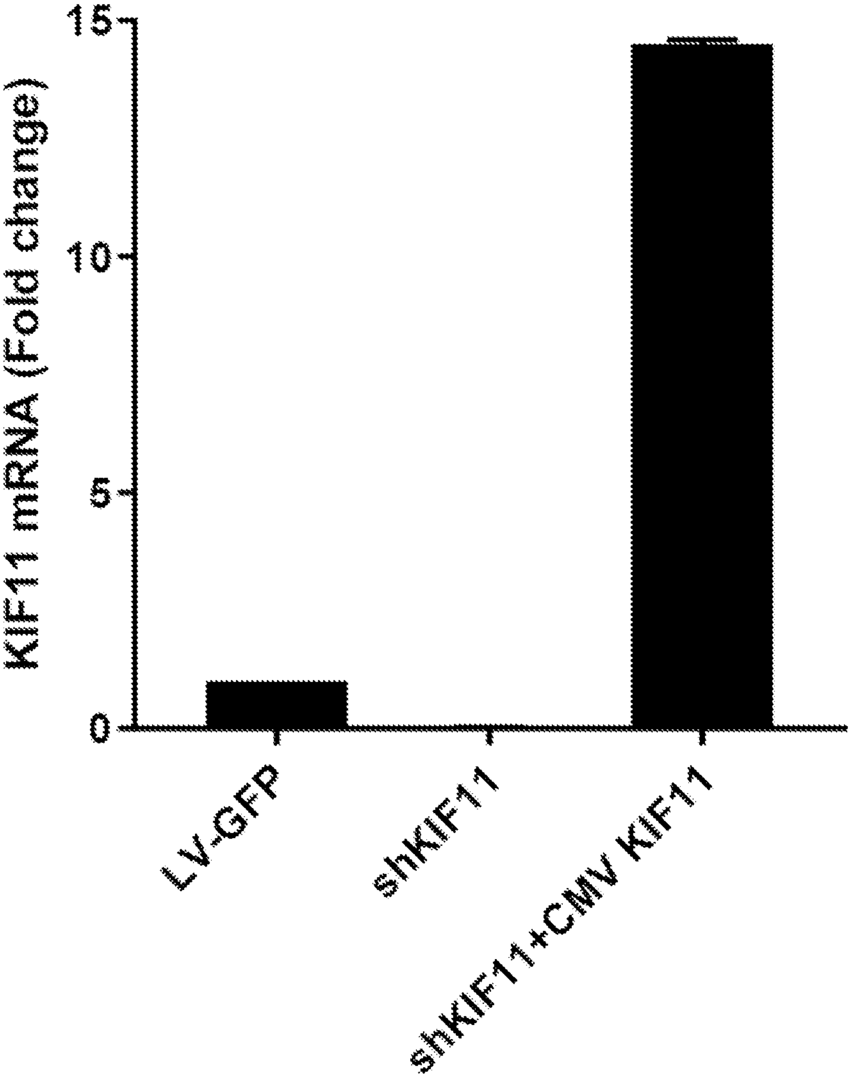
FIG. 6 depicts data demonstrating effect on KIF11 mRNA levels after lentiviral-delivered co-expression of both a shRNA-based RNA targeting the human KIF11 untranslated region and a KIF11 gene.

As shown in FIG. 6, relative to the control treated LV-GFP treated cells, KIF11 mRNA: (i) decreased 77% when cells were transduced with the vector expressing the KIF11 shRNA sequence #3 (SEQ ID NO: 3) (see, bar showing KIF11 mRNA expression after transduction with shKIF11); and (ii) increased 14.5-fold when cells were transduced with the vector expressing the KIF11 shRNA sequence #3 (SEQ ID NO: 3) and the KIF11 sequence (SEQ ID NO: 4) (see, bar showing KIF11 mRNA expression after transduction with shKIF11+CMV KIF11). This shows that shRNA is suppressing endogenous KIF11 mRNA and not affecting expression of KIF11 from the transgene.

Example 4: Lentiviral Particle-Delivered shRNA-Based RNA Interference Targeting the Human KIF11 (Eg5) Untranslated Region, Results in Reduced Numbers of Viable Cells PC3 human prostate carcinoma cells were transduced with a lentiviral vector particle containing the H1 promoter and either KIF11 shRNA sequence #2 (SEQ ID NO: 2) or sequence #3 (SEQ ID NO: 3).

PC3 human prostate carcinoma cells were seeded in 24-well plates at $5\times10^4$ cells per well. After 24 hours, the cells were transduced at 5 MOI with a lentiviral vector particle expressing either KIF11 UTR shRNA #2 or #3 (SEQ ID NO: 2 or SEQ ID NO: 3, respectively). After 4 days, cell number was determined with the MTT reagent (Sigma) at 570 nm. The MTT reagent is a tetrazolium dye (3-(4,5-dimethylthiazol-2-yl)-2,5-diphenyltetrazolium bromide. In metabolically active, viable cells the NAD(P)H-dependent oxidoreductase enzymes cause reduction of the MTT reagent to its insoluble form known as formazan, which is purple in color. An MTT assay for cell viability was performed by adding the MTT reagent to a cell suspension then examining cells under the microscope to enumerate the proportion appearing purple. Automated versions of the MTT assay distributes cells to individual wells of a plastic plate followed by colorimetry to measure the intensity of purple color.

Figure 7:
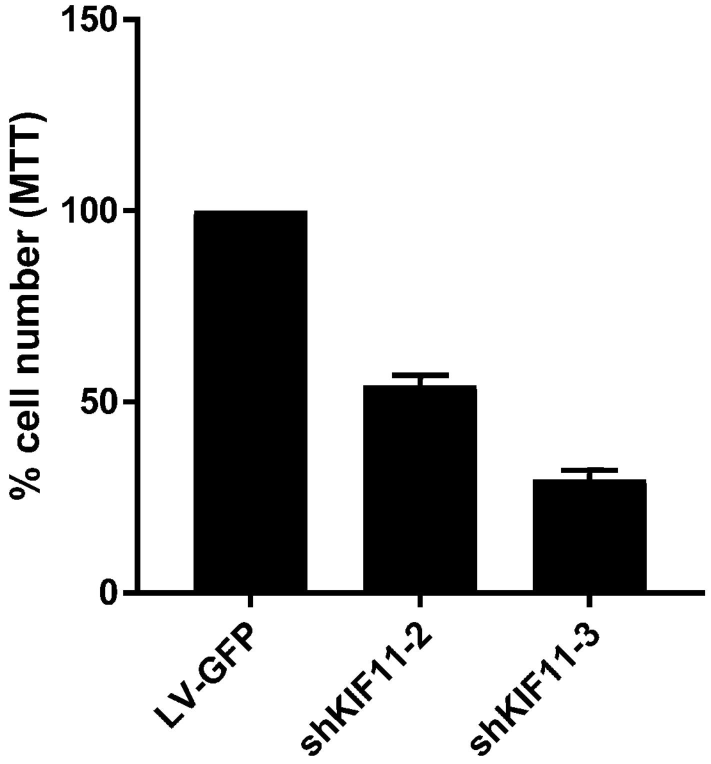
FIG. 7 depicts data demonstrating the effect of KIF11 knockdown on the proliferation of PC3 cells.

As shown in FIG. 7, as compared to LV-GFP transduced cells, the number of cells: (i) decreased 46% in cells transduced with the KIF11 shRNA #2 sequence (SEQ ID NO: 2) (see, bar showing % cell number after transduction with shKIF11-2); and (ii) decreased 70% in cells transduced with the KIF11 shRNA #3 sequence (SEQ ID NO: 3) (see, bar showing % cell number after transduction with shKIF11-3). This suggests that KIF11 is a valid target for reducing cancer cell proliferation.

Example 5: Lentiviral Particle-Delivered Co-Expression of Both (i) a shRNA-Based RNA Interference Targeting the Human KIF11 Untranslated Region and (ii) a KIF11 Coding Sequence, Results in Maintaining High Levels of Cell Number PC3 human prostate carcinoma cells were transduced with lentiviral vector particles expressing (i) GFP (control), (ii) shKIF11 (UTR), and (iii) a shKIF11 (UTR) and a sequence that encodes KIF11 (SEQ TD NO: 4) driven by a CMV promoter. The shKIF11 (UTR) sequence used in each of the lentiviral vector particles was the KIF shRNA sequence #3 (SEQ ID NO: 3). The sequence that encodes KIF11 (SEQ ID NO: 4) comprised a truncation in the 3'UTR of the KIF11 gene.

PC3 human prostate carcinoma cells were seeded in 24-well plates at $5\times10^4$ cells per well. After 24 hours, the cells were transduced at 5 MOI with lentiviral vector particles expressing KIF11 UTR shRNA #3 (SEQ ID NO: 3) alone or co-expressed with the KIF11 coding sequence as well as the lentiviral vector particle expressing only GFP (control). After 4 days, cell number was determined by culturing with the MTT reagent ((3-(4,5-dimethylthiazol-2-yl)-2,5-diphenyl tetrazolium bromide) (SigmaMillipore) which produces a dark blue formazan product in live cells. The MTT assay was carried out as described in Example 4.

Figure 8:
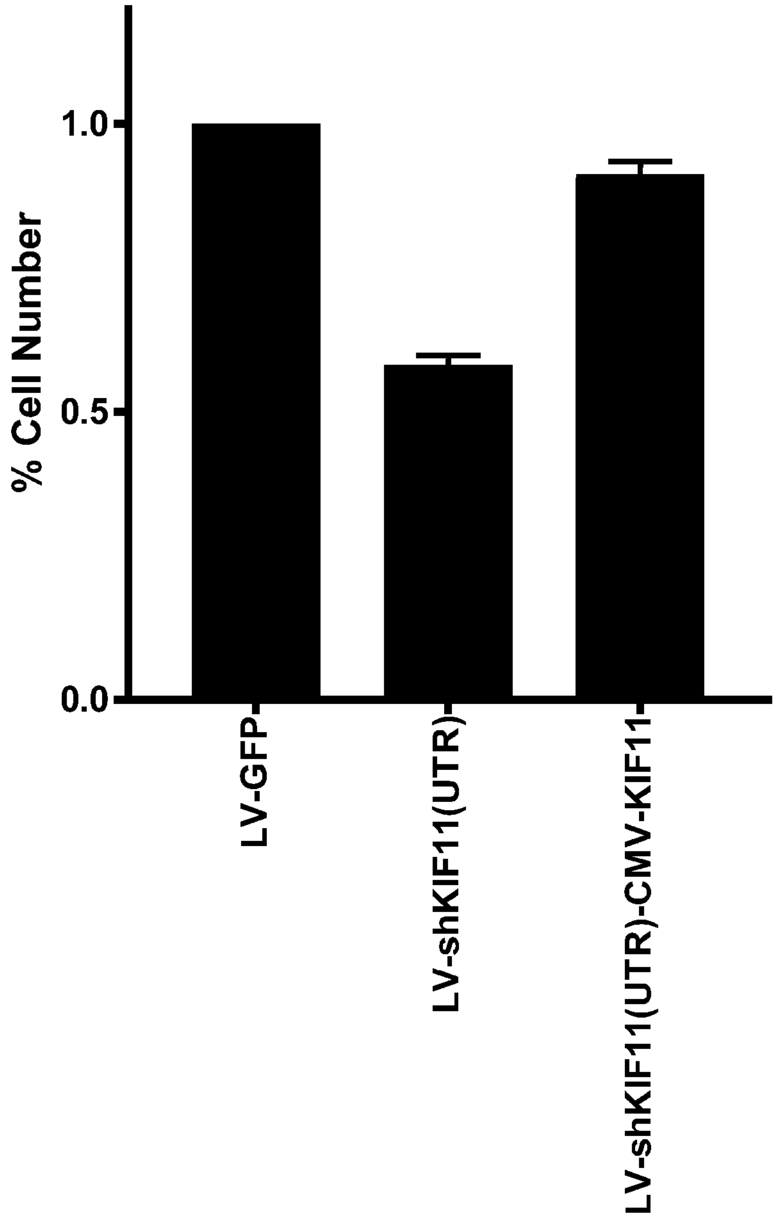
FIG. 8 depicts data demonstrating effect on proliferation of PC3 cells after lentiviral-delivered co-expression of both a shRNA-based RNA targeting the human KIF11 untranslated region and a KIF gene.

As shown in FIG. 8, as compared to LV-GFP transduced cells (see, bar showing % cell number after transduction with LV-GFP) (control vector set at 100%), the number of cells decreased 42% in cells that were transduced with the KIF11 shRNA sequence #3 (SEQ ID NO: 3) (see, bar showing % cell number after transduction with LV-shKIF11 (UTR). This reduction in number of cells was rescued to only a 9% decrease in cells that were transduced with the vector expressing the KIF11 shRNA sequence #3 (SEQ ID NO: 3) and the KIF11 coding sequence (see, bar showing % cell number after transduction with LV-shKIF11 (UTR)-CMV-KIF11). Therefore, proliferation of PC3 was minimally affected by KIF11 shRNA when an exogenous KIF11 was expressed that contained a truncated 3'UTR.

Example 6: Mesenchymal Stem Cells can be Modified to Produce Inhibitory RNA Against a Required Cell Cycle Protein and Retain Growth Potential by Using a 2-Component Lentivirus Vector This Example illustrates use of a 2-component lentivirus vector to enable the bulk manufacturing from seed stock, of a mesenchymal stem cell product that proliferates in culture while also expressing high levels of inhibitory RNA blocking a critical function for cell growth.

The kinesin family member protein KIF11 is required for spindle formation and mitosis. It has been observed that inhibitory RNA capable of reducing the levels of KIF11 will reduce malignant tumor growth. Consequently, delivery of such an inhibitory RNA to the tumor microenvironment will be of therapeutic value. One method for delivering inhibitory RNA involves the use of mesenchymal stem cells. The cells have special properties for engaging cell-to-cell contact with tumor cells and delivering various molecules via a portal formed by connexin proteins.

Normal manufacturing for therapeutic doses of mesenchymal stem cells starts with a seed stock of highly characterized cells, which are expanded through several days of cell growth to achieve the numbers of cells required for in vivo therapy. Clearly, alternative strategies are needed to manufacture therapeutic doses of genetically modify mesenchymal stem cells that are programmed to produce high levels of an inhibitory RNA destined to suppress tumor cell growth.

The 2-component lentivirus vector system overcomes the problem of manufacturing modified mesenchymal stem cells. In this embodiment, the lentivirus vector expresses a modified version of the KIF11 gene containing the normal protein coding sequence but lacking the 3' untranslated region found normally in messenger RNA. From a separate cassette, the same lentivirus vector also expresses one or more inhibitory RNA in the form of a siRNA, shRNA, or microRNA that is targeted against the 3' untranslated region of normal KIF11 mRNA. In this way the modified mesenchymal stem cell expresses sufficient levels of KIF11 protein to maintain cell growth and also produces high levels of the inhibitory RNA that can be exported via connexin channels into tumor cells where it will suppress malignant growth. This is accomplished without sacrificing the ability to manufacture large cell doses of modified mesenchymal stem cells from a seed stock. Thus, the seed stock has been modified by a 2-component lentivirus vector, characterized in advance, qualified for clinical use and available as a cell and gene therapy for multiple tumor types.

Figure 9:
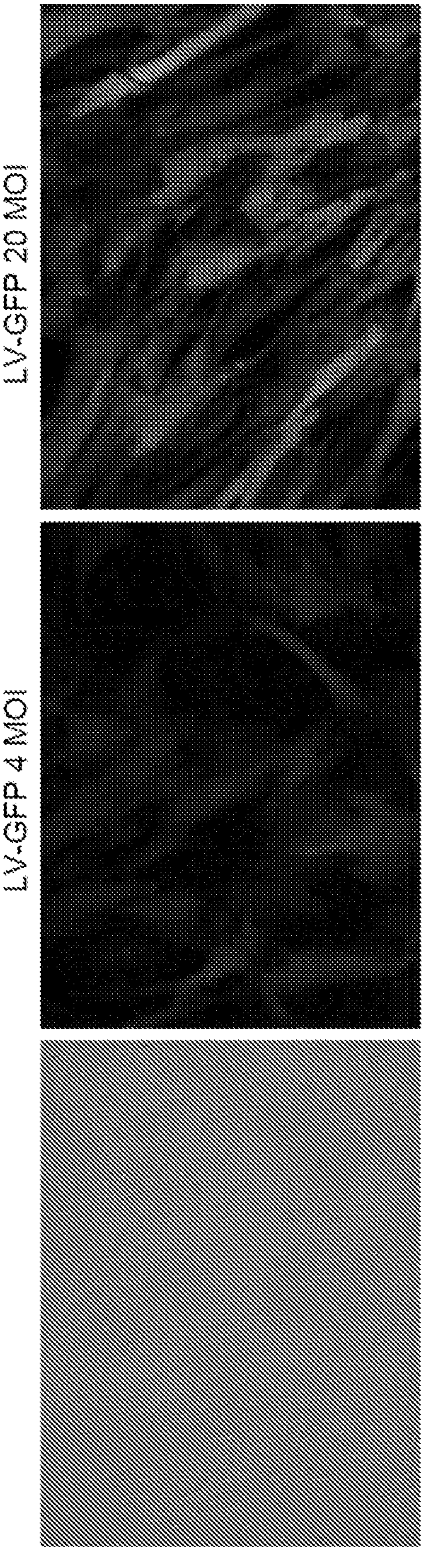
FIG. 9 depicts data demonstrating transduction of mesenchymal stem cells with a lentiviral vector expressing GFP.

Example 7: Transduction of Mesenchymal Stem Cells (MSCs) with a Lentiviral Vector Particle Expressing GFP Results in a Dose-Dependent Increase in GFP Expression MSCs were passaged three times and then seeded in 24 well plates at $2\times10^4$ cells per well. After 24 hours, the cells were transduced with a lentiviral vector (LV) particle expressing GFP at 4 and 20 multiplicity of infection (MOI) (based on a 293T titer value). After three days, the cells were imaged for GFP Fluorescence. As shown in FIG. 9, there was a dose-dependent increase in GFP brightness of the cells. As shown in the middle panel (LV-GFP 4 MOI), about 80% of the MSCs stained positive for GFP. As shown in the right panel (LV-GFP 20 MOI), close to 100% of the MSCs stained positive for GFP.

Example 8: Multiplicity of Infection Equal to 4 was Sufficient to Achieve 10 Vector Genomes Per Mesenchymal Stem Cell (MSC)

MSCs were passaged three times and then seeded in 6-well plates at $1\times10^5$ cells per well. After 24 hours, the cells were transduced with lentiviral vector particles expressing KIF11 shRNA sequence #3 (SEQ ID NO: 3) alone or KIF11 shRNA sequence #3 (SEQ ID NO: 3) with the KIF11 sequence (SEQ ID NO: 4). The vector particles also expressed GFP as a transduction marker. After 72 hours, genomic DNA was extracted with the DNeasy kit (Qiagen). A duplex PCR reaction was performed with 25 and 50 ng of DNA on a QuantStudio 3 qPCR machine using vector-specific Gag primers (Gag forward primer (SEQ ID NO: 53); Gag reverse primer (SEQ ID NO: 54)) and a FAM-labeled probe (SEQ ID NO: 55)) and Actin primers (Actin forward primer (SEQ ID NO: 49); Actin reverse primer #2 (SEQ ID NO: 51)) and a VIC-labeled probe (SEQ ID NO: 52)), as a cell control. The number of vector copies from the cell samples were determined with a standard curve using a lentiviral plasmid containing the Gag and actin sequences. The vector copy number was calculated using the formula: (Quantity Mean of Gag sequence/Quantity mean of Actin sequence).

Figure 10:
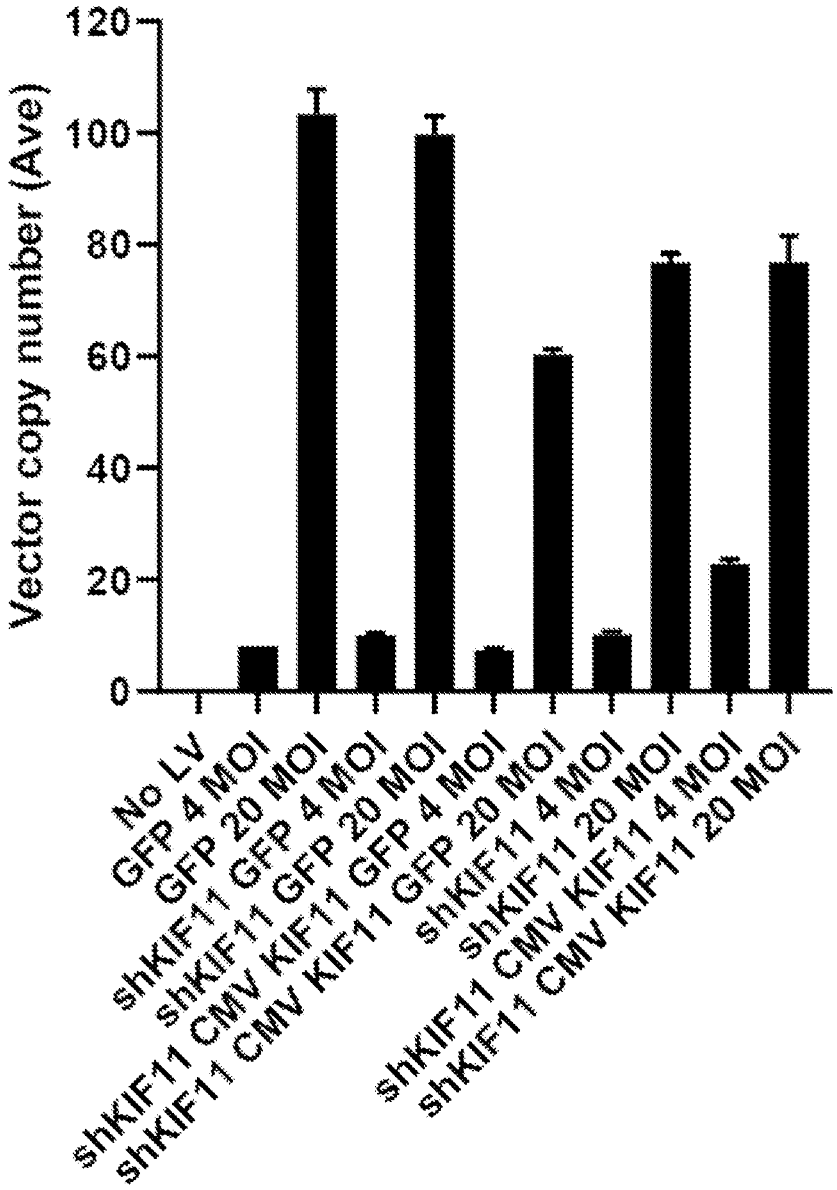
FIG. 10 depicts data demonstrating vector copy number of mesenchymal stem cells after transduction with various lentiviral vectors expressing shRNA against KIF11.

Results showing the vector copy number are shown in FIG. 10. In each of the vector particles in which 4 MOI was used, the vector copy number was between 7 and 20 (see, bars showing vector copy number of vectors transduced at 4 MOI: (i) GFP 4 MOI, (ii) shKIF11 GFP 4 MOI, (iii) shKIF11 CMV KIF11 GFP 4 MOI, (iv) shKIF11 4 MOI, and (iv) shKIF11 CMV KIF11 4 MOI). In each of the vectors in which 20 MOI was used, the vector copy number was between 60 and 100 (see, bars showing vector copy number of vectors transduced at 20 MOI: (i) GFP 20 MOI, (ii) shKIF11 GFP 20 MOI, (iii) shKIF11 CMV KIF11 GFP 20 MOI, (iv) shKIF11 20 MOI, and (v) shKIF11 CMV KIF11 20 MOI).

The preferred vector copy number ranges between 1 and 10, with 5 or less typically being the target. The ideal target for the vector copy number is influenced by the functional efficiency of the vector. For example, a vector expressing a shRNA against a target, should reduce the target gene expression greater than 80% with a vector copy number of 5 or less. However, it is known that a vector copy number that is greater than 10 can cause genotoxicity. Thus, the data indicates that using 20 MOI is too high.

Example 9: Lentiviral Vector Particles Expressing the KIF11 UTR-Targeted shRNA Reduces KIF11 mRNA Levels in Mesenchymal Stem Cells (MSCs); mRNA Levels are Restored in Cells Transduced with a Lentivirus Co-Expressing Truncated KIF11 and the UTR-Targeting shRNA MSCs were passaged three times and then seeded in 6-well plates at $1\times10^5$ cells per well. After 24 hours, the cells were transduced with lentiviral vector particles expressing either KIF11 shRNA sequence #3 (SEQ ID NO: 3) alone or KIF11 shRNA sequence #3 (SEQ ID NO: 3) and the KIF11 coding sequence (SEQ ID NO: 4). Certain lentiviral vector particles also expressed GFP as a transduction marker. After 72 hours, RNA was extracted from the cells with the RNeasy kit (Qiagen) and converted to cDNA with SuperScript VILO (Thermo). Expression of KIF11 cDNA was determined by quantitative PCR using TaqMan probes (SEQ ID NO: 48) and primers for KIF11 (KIF11 forward primer (SEQ ID NO: 46); KIF11 reverse primer (SEQ ID NO: 47)) and actin (Actin forward primer (SEQ ID NO: 49; Actin reverse primer #1 (SEQ ID NO: 50)), and a VIC-labeled probe (SEQ ID NO: 52). KIF11 expression was normalized to actin levels for each sample.

Figure 11:
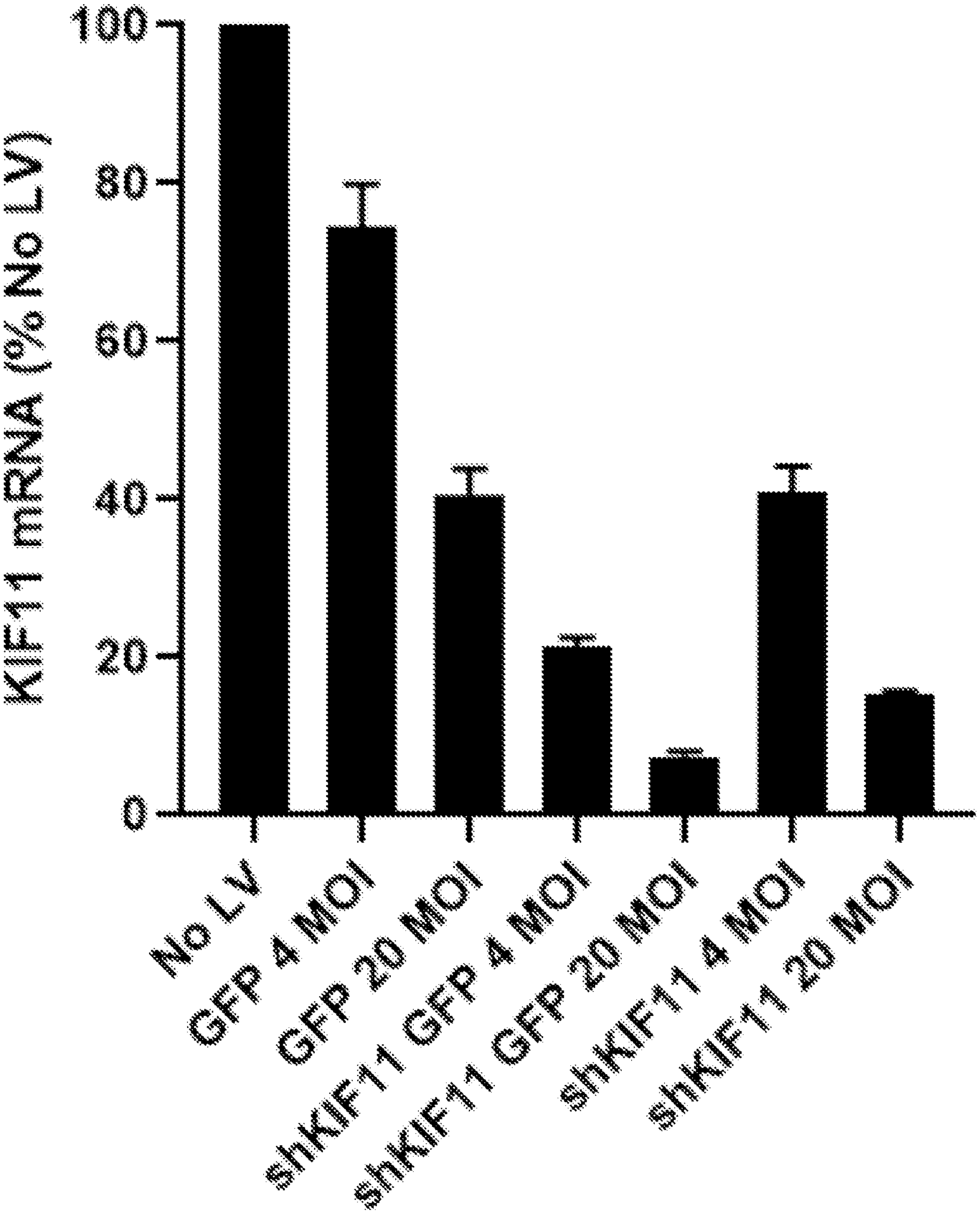
FIGS. 11A and 11B depict data showing KIF11 mRNA expression in mesenchymal stem cells after transduction with lentiviral vectors expressing: (A) a shRNA against KIF11 alone; and (B) a shRNA against KIF11 and a KIF11 coding sequence.

FIG. 11A represents KIF11 RNA expression as a percentage of non-transduced cells (NO LV). As compared to non-transduced MSCs, a vector containing the KIF11 shRNA sequence #3 (SEQ ID NO: 3) and GFP, resulted in a 79 percent decrease in KIF11 RNA and 92.5% decrease in KIF11 RNA at 4 MOI (see, bar showing data of KIF11 mRNA after transduction with shKIF11 GFP 4 MOI) and 20 MOI (see, bar showing data of KIF11 mRNA after transduction with shKIF11 GFP 20 MOI), respectively. As compared to non-transduced MSCs, vectors containing the KIF11 shRNA sequence #3 (SEQ ID NO: 3) without GFP, resulted in a 59 percent decrease in KIF11 RNA and an 85 percent decrease in KIF11 RNA at 4 MOI (see, bar showing data of KIF11 mRNA after transduction with shKIF11 4 MOI) and 20 MOI (see, bar showing data of KIF11 mRNA after transduction with shKIF11 20 MOI), respectively. Thus, in both vectors expressing KIF11 shRNA, increasing the MOI resulted in a greater decrease in KIF11 mRNA expression, regardless of whether the vector expressed GFP.

Of note, transduction with vectors that only contained GFP resulted in a reduction of KIF11 mRNA. For example, as compared to non-transduced MSCs, vectors expressing only GFP resulted in a 59 percent decrease in KIF11 mRNA when the vector was transduced at 20 MOI (see, bar showing data of KIF11 mRNA after transduction with GFP 20 MOI). It is not clear why such a decrease in KIF11 mRNA was observed. However, as revealed from the vector copy number data (see, FIG. 10), 20 MOI results in a high vector copy number. This high vector copy number could be causing toxicity and may, therefore, explain that shRNA-independent effect on KIF11 mRNA.

Figure 11B:
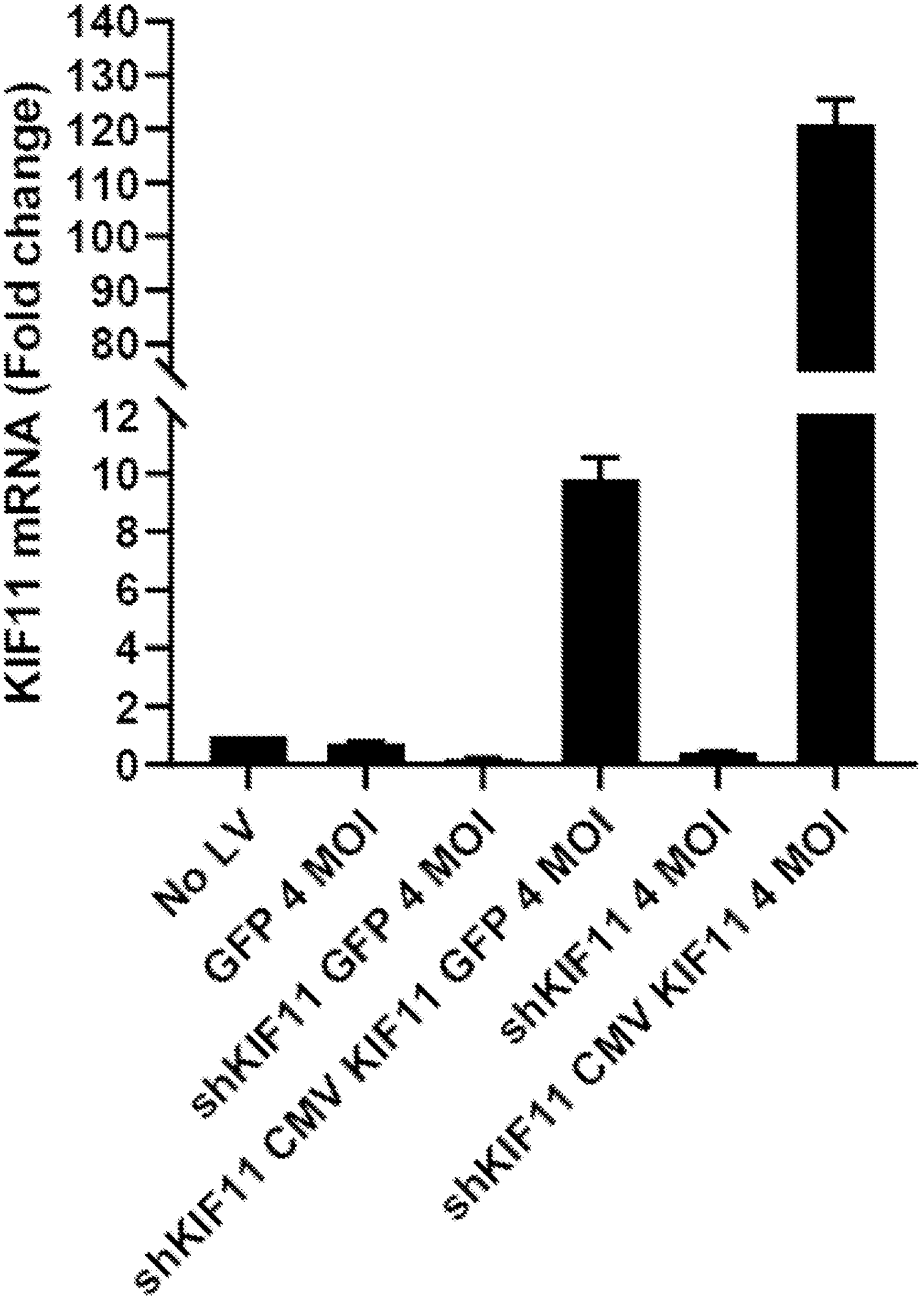

FIG. 11B represents KIF11 mRNA expression as a fold change relative to non-transduced cells (No LV). In the vector that expressed KIF11 shRNA sequence #3 (SEQ ID NO: 3), the KIF11 coding sequence (SEQ ID NO: 4), and GFP, there was a 9.8-fold increase in KIF11 mRNA and the KIF11 coding sequence (see, bar showing KIF11 mRNA after transduction with shKIF11 CMV KIF11 GFP 4 MOI). In the vector that expressed KIF11 shRNA sequence #3 (SEQ ID NO: 3), the KIF11 coding sequence (SEQ ID NO:

4), and no GFP, there was a 121-fold increase in KIF11 mRNA and the KIF11 coding sequence (see, bar showing KIF11 mRNA after transduction with shKIF11 CMV KIF11 4 MOI). This indicates that increasing the complexity of the vector (i.e. adding GFP) causes a reduction in vector-expressed KIF11.

Example 10: KIF11 UTR-Targeted shRNA does not have an Effect on the Proliferation of Mesenchymal Stem Cells (MSCs) During a Single Cell Passage MSCs were passaged three times and then seeded in 24-well plates at $2\times10^4$ cells per well. After 24 hours, the cells were transduced with lentiviral vector particles expressing either KIF11 shRNA sequence #3 (SEQ ID NO: 3) alone or KIF11 shRNA sequence #3 (SEQ ID NO: 3) and the KIF11 coding sequence (SEQ ID NO: 4). After six days, cell number was determined after incubation for two hours with the MTT reagent (Sigma) and detection at 570 nm with a plate reader.

Figure 12:
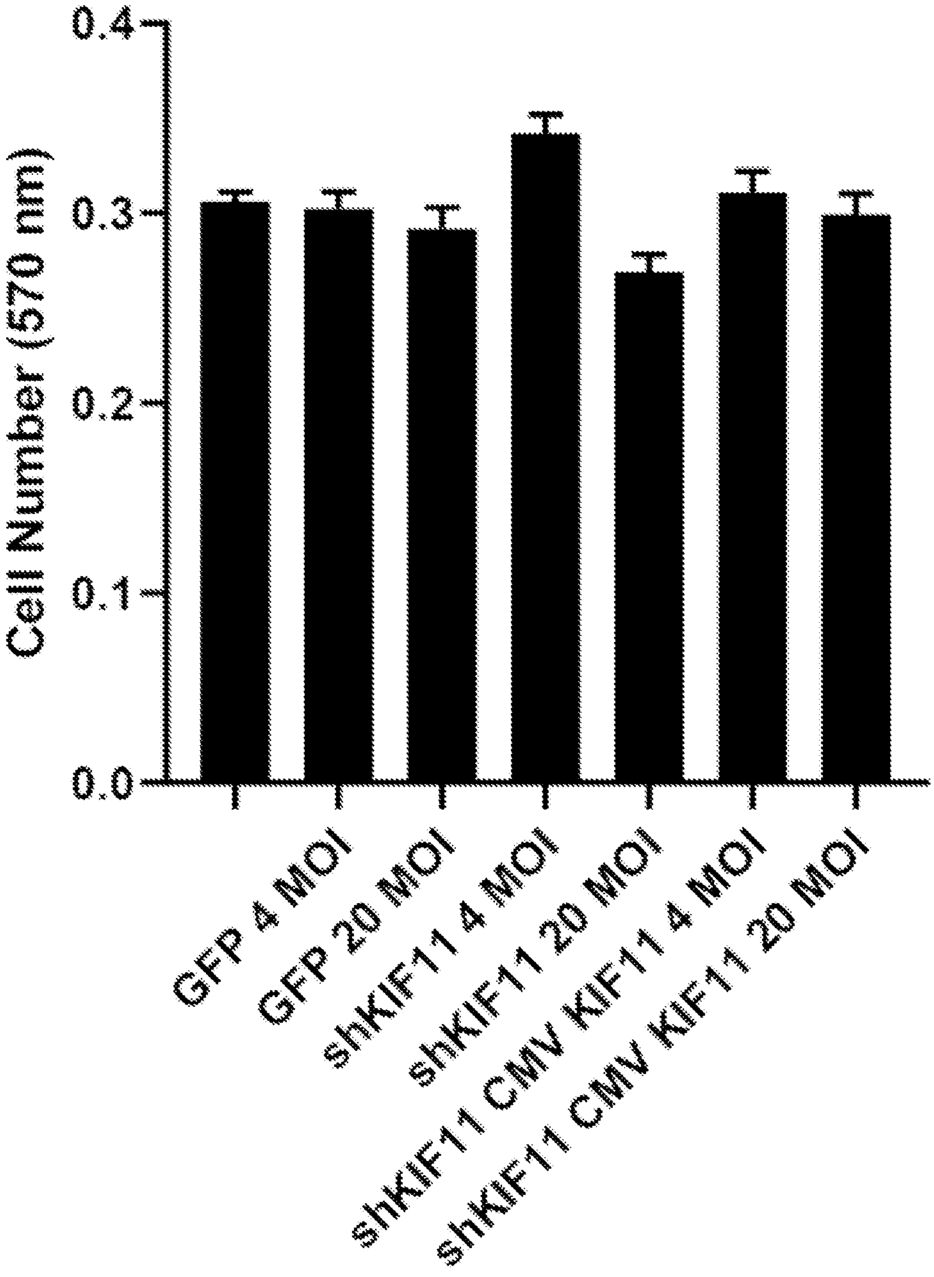
FIG. 12 depicts data showing cell number of mesenchymal stem cells after transduction with vectors expressing shRNA that targets KIF11 or vectors co-expressing shRNA that targets KIF11 and the KIF11 coding sequence.

As shown in FIG. 12, transduction with either lentiviral vector particles expressing the KIF11 shRNA sequence alone (see, bars showing cell number after transduction with shKIF11 4 MOI and shKIF11 20 MOI) or lentiviral vector particles expressing the KIF11 shRNA sequence and the KIF11 coding sequence (see, bars showing cell number after transduction with shKIF11 CMV KIF11 4 MOI and shKIF11 CMV KIF11 20 MOI) resulted in minimal change in the MSCs when compared to control treatments (see, bars showing cell number after transduction with either GFP 4 MOI and GFP 20 MOI). This data may suggest that the vector need not co-express the KIF11 coding sequence in order to maintain survival of the mesenchymal stem cells. Alternatively, expression of the KIF11 shRNA may have a negative impact on survival of the mesenchymal stem cells when trying to expand the MSCs to large, commercial scale cell volumes. Thus, large scale expansion may reveal the benefit of exogenous co-expression of KIF11 to maintain cell yield of the MSCs.

Example 11: Materials and Methods

Detailed methods of: (i) generating lentiviral vectors expression KIF11 shRNA; (ii) generating KIF11 shRNA sequences; (iii) measuring KIF11 RNA expression; (iv) measuring vector copy number; and (v) measuring cell proliferation, which were used to generate the data herein, are described below.

Generation of Lentiviral Vector Particles Expressing KIF11 shRNA

Potential RNA interference sequences were chosen from candidates selected with the shRNA design program from the Broad Institute or the BLOCK-iT™ RNAi Designer from Thermo Scientific. Short-hairpin oligonucleotide sequences containing BamHI and EcoRI restriction sites were synthesized by Eurofins Genomics. Oligonucleotide sequences were annealed by incubating at 70 degrees Celsius and then cooling to room temperature for 1 hour. In parallel, the lentiviral vectors were digested with the restriction enzymes BamHI and EcoRI for one hour at 37 degrees Celsius. The digested lentiviral vectors were purified by agarose gel electrophoresis and extracted from the gel using a DNA gel extraction kit (Thermo Scientific). The DNA concentration was determined for each and 50 ng of vector were added to 2 microliters of annealed oligo. The ligation reactions were performed with T4 DNA ligase for 30 minutes at room temperature. 2.5 microliters of the ligation mix were added to 25 microliters of Stbl3 competent bacterial cells. Transformations were done with a heat-shock step at 42 degrees Celsius. Bacterial cells were streaked onto agar plates containing ampicillin and selected colonies were expanded in LB broth. To check for insertion of the oligo sequences, plasmid DNA was extracted from harvested bacterial cultures with a DNA mini prep kit (Thermo Scientific). Insertions of the shRNA sequence in the lentiviral vector were verified by DNA sequencing using H1 primers. Lentiviral vectors containing shRNA sequences were packaged into lentiviral particles to test for their ability to knock-down KIF11 RNA.

Generating KIF11 shRNA Sequences

The sequence of *Homo sapiens* kinesin family member 11 (KIF11) (Eg5) (NM_004523.4) mRNA was used to search for potential shRNA candidates to reduce KIF11 levels in human cells. The search identified three KIF11 shRNA candidates (SEQ ID NO: 1, SEQ ID NO: 2, and SEQ ID NO: 3).

Measuring KIF11 RNA Expression

The effects of the three different KIF11 shRNA sequences on KIF11 expression were determined by measuring mRNA expression following transduction with the lentiviral vectors. PC3 cells were transduced by adding lentivirus vector at a MOI of 5 (based on 293T titer) plus 8 μg/mL of polybrene (MilliporeSigma) to cells and incubating overnight. After 24 hours, the medium was changed, and the cells were cultured for an additional 72 hours. After 72 hours, cells were lysed, and RNA was extracted using the RNeasy mini kit. cDNA was synthesized from 100 ng of RNA using the SuperScript VILO cDNA synthesis kit. PCR reactions were performed using the TaqMan Fast Advanced Master Mix and the samples were then analyzed by quantitative PCR (qPCR) using an Applied Biosystems QuantStudio3 qPCR machine (Thermo Scientific). KIF11 expression was detected using KIF11 primers/probe (KIF11 forward primer (SEQ ID NO: 46); KIF11 reverse primer (SEQ ID NO: 47); KIF11 probe (SEQ ID NO: 48)) and normalized to actin (Actin forward primer (SEQ ID NO: 49; Actin reverse primer #1 (SEQ ID NOs: 50); Actin probe (SEQ ID NO: 52). The relative expression of KIF11 was determined by its Ct value and normalized to the level of actin for each sample.

Measuring Vector Copy Number

MSCs were transduced by adding lentivirus vector plus 8 μg/mL of polybrene (MilliporeSigma) to cells and incubating overnight. After 24 hours, the medium was changed, and the cells were cultured for another 48-72 hours. Then the cells were washed with PBS 2× and the cell pellet was collected to extract genomic DNA with the DNeasy kit (Qiagen). A 50 ng/mL solution of the genomic DNA was prepared. The vector copy number was determined by performing qPCRs with primer and probe sets for a sequence encoded by the lentiviral vector, Gag (Gag forward primer (SEQ ID NO: 53); Gag reverse primer (SEQ ID NO: 54); Gag probe (SEQ ID NO: 55), and for the cellular beta actin gene (Actin forward primer (SEQ ID NO: 49); Acting reverse primer #2 (SEQ ID NO: 51); Acting probe (SEQ ID NO: 52)) on genomic DNAs from transduced cells alongside standard curve samples created using a plasmid that encodes gag and beta actin. PCR reactions were performed using the TaqMan Fast Advanced Master Mix and the samples were then analyzed by qPCR using an Applied Biosystems QuantStudio3 qPCR machine (Thermo Scientific). The copy number of integrated lentivirus was calculated based on the Ct values as determined by qPCR. The following formula was used to measure vector copy number: Vector copy number=(Quantity mean of Gag sequence/Quantity mean of Actin sequence).

Measuring Cell Proliferation

PC3 and MSC cells were seeded in 24-well plates. After the designated culture time, the media was removed and 0.5 mL of DMEM containing 0.5 mg/mL of MTT was added to the cells. The plate was returned to an incubator at 37 degrees Celsius for 30 minutes for PC3 cells and 2 hours for MSCs. The media was removed, and 0.5 mL of isopropanol was added to the wells. The plate was placed on a rocker at a low speed for 5 minutes and the color was detected with a Bio-Tek plate reader at an absorbance of 570 nm.

Example 12: MSC Isolation, Purification, Expansion, and Characterization

Isolation, purification, and expansion: MSCs are isolated from placentas, which are recovered after elective cesarean section delivery for full-term newborns. The placenta is washed in phosphate buffered saline (PBS) and the maternal decidua is removed. Tissue portions of approximately 1 $cm^3$ or 4 grams wet weight are dissected from the fetal interfacing chorionic villous. Tissue portions are washed again in PBS and treated at 37° C. with 1 mg/mi Collagenase A solution for 60 minutes. Digested material is collected by centrifugation and resuspended in a trypsin/EDTA solution for 10 minutes at 37° C. Trypsin-treated material is collected again by centrifugation, washed once, resuspended in Bio-AMF-1 medium (Biological Industries, Israel) with 1% penicillin-streptomycin solution plus 5 mM L-Glutamine. Cells were transferred to T-25 culture flasks and incubated in a humidified atmosphere at 37° C. with 5% $CO_2$. When MSC reach confluence in the T-25 flask, they are treated with trypsin/EDTA to release cells bound to plastic, diluted with medium and re-plated in new T-25 flasks.

For large scale manufacturing of gene modified MSCs for clinical use, a seed stock containing 10-50 million transduced MSCs are enlarged through serial passage and adapted to suspension culture. The final cell culture volume may reach 100 to 200 L, with cell yields approaching $5\times10^9$ per liter. Cells are recovered by centrifugation and/or filtration, washed and resuspended in medium for in vivo administration. Large scale expansion of MSCs can be performed in suspension cultures of up to 200 L under GMP conditions.

Other methods of isolating and expanding MSCs that are known in the art can be used. Detailed protocols for isolating and expanding MSCs are described in the following references, which are incorporated herein by reference in their entirety: (i) Huang Q, Yang Y, Luo C, Wen Y, Liu R, Li S, Chen T, Sun H, and Tang L. 2019. *An efficient protocol to generate placental chorionic plate-derived mesenchymal stem cells with superior proliferative and immunomodulatory properties*. Stem Cell Research & Therapy 10:301. (ii) Hassan G, Kasem I, Antaki, R, Mohammad M B, AlKadry R, and Aljamali M. 2019. *Isolation of umbilical cord mesenchymal stem cells using blood derivatives accompanied with explant method*. Stem Cell Investigation 6:29.

Characterization: The MSC phenotype varies according to tissue of origin. For chorionic villous MSCs the major phenotypic markers of cell identity include: CD44, CD73, CD105, CD90, alpha-SMA, and Stro-1. Antibody staining and flow cytometry to detect these cell surface markers will confirm the presence of MSC and further indicate the fraction of cells most similar to chorionic villous MSC. Specific patterns of gene expression have also been identified for MSCs. Chorionic villous MSCs express SOX-2 but not NANOG or POU5F1. Expression of all three of these genes is a common marker for embryonic stem cell pluripotency, expression limited to SOX-2 is consistent with the partially pluripotent phenotype of MSC.

Example 13: Lentivirus Vector Particle Genetic Modification of MSCs

Lentivirus vectors are a preferred method for stable genetic modification of MSC and have been evaluated in short-term and long-term cultures of bone marrow-derived and other types of MSC. Creating lentivirus vectors expressing both marker proteins (green or red fluorescence proteins) and puromycin acetyltransferase (confers resistance to puromycin) allow for drug selection of genetically modified MSC, which appear identical to unmodified MSC after a battery of tests for phenotypic changes, altered cell mobility, or capacity for cell amplification in long-term culture.

Lentivirus vector particle transduction can be performed in three steps:

Step 1: confluent MSCs are trypsinized, diluted 1:3 and replated for 2 days.

Step 2: Lentivirus vector stock in PBS plus 8 ug/mL Polybrene is overlayed on the MSC cell monolayer for 4 hours then removed by rinsing cells with medium.

Step 3: MSCs are detached from the plate with trypsin solution and used for DNA, RNA, or protein extraction that will measure the efficiency of transduction.

For most lentivirus vectors, transduction with multiplicity of infection equal to 5 results in >80% of MSCs becoming genetically modified. The modifications are stable and transgene expression persists for many generations.

Sequences

The following sequences are referred to herein.

| SEQ ID NO: | Description | Sequence |
|---|---|---|
| 1 | KIF11 small RNA sequence #1 | TTTGATCTGGCAACCATATTTCTCGAGAAATATGGTTGCCAGATCAAATTTTT |
| 2 | KIF11 small RNA sequence #2 | TGCAATGTAAATACGTATTTCCTCGAGGAAATACGTATTTACATTGCATTTTT |
| 3 | KIF11 small RNA sequence #3 | GCTTGAGCTTACATAGGTAACTCGAGTTACCTATGTAAGCTCAAGCTTTTT |
| 4 | KIF11 sequence | ATGGCGTCGCAGCCAAATTCGTCTGCGAAGAAGAAAGAGGAGAAGGGGAAGAACATCCAGGTGGTGGTGAGATGCAGACCATTTAATTTGGCAGAGCGGAAAGCTAGCGCCCATTCAATAGTAGAATGTGATCCTGTACGAAAAGAAGTTAGTGTACGAACTGGAGGATTGGCTGACAAGAGCTCAAGGAAAACATACACTTTTGATATGGTGTT |

-continued

| SEQ ID NO: | Description | Sequence |
|---|---|---|
| | | TGGAGCATCTACTAAACAGATrGATGTTTACCGAAGTGTTGTT<br>TGTCCAATTCTGGATGAAGTTATTATGGGCTATAATTGCACTA<br>TCTTTGCGTATGGCCAAACTGGCACTGGAAAAACTTTTACAAT<br>GGAAGGTGAAAGGTCACCTAATGAAGAGTATACCTGGGAAGAG<br>GATCCCTTGGCTGGTATAATTCCACGTACCCTTCATCAAATTT<br>TTGAGAAACTTACTGATAATGGTACTGAATTTTCAGTCAAAGT<br>GTCTCTGTTGGAGATCTATAATGAAGAGCTTTTTGATCTTCTT<br>AATCCATCATCTGATGTTTCTGAGAGACTACAGATGTTTGATG<br>ATCCCCGTAACAAGAGAGGAGTGATAATTAAAGGTTTAGAAGA<br>AATTACAGTACACAACAAGGATGAAGTCTATCAAATTTTAGAA<br>AAGGGGGCAGCAAAAAGGACAACTGCAGCTACTCTGATGAATG<br>CATACTCTAGTCGTTCCCACTCAGTTTTCTCTGTTACAATACA<br>TATGAAAGAAACTACGATTGATGGAGAAGAGCTTGTTAAAATC<br>GGAAAGTTGAACTTGGTTGATCTTGCAGGAAGTGAAAACATTG<br>GCCGTTCTGGAGCTGTTGATAAGAGAGCTCGGGAAGCTGGAAA<br>TATAAATCAATCCCTGTTGACTTTGGGAAGGGTCATTACTGCC<br>CTTGTAGAAAGAACACCTCATGTTCCTTATCGAGAATCTAAAC<br>TAACTAGAATCCTCCAGGATTCTCTTGGAGGGCGTACAAGAAC<br>ATCTATAATTGCAACAATTTCTCCTGCATCTCTCAATCTTGAG<br>GAAACTCTGAGTACATTGGAATATGCTCATAGAGCAAAGAACA<br>TATTGAATAAGCCTGAAGTGAATCAGAAACTCACCAAAAAAGC<br>TCTTATTAAGGAGTATACGGAGGAGATAGAACGTTTAAAACGA<br>GATCTTGCTGCAGCCCGTGAGAAAAATGGAGTGTATATTTCTG<br>AAGAAAATTTTAGAGTCATGAGTGGAAAATTAACTGTTCAAGA<br>AGAGCAGATTGTAGAATTGATTGAAAAAATTGGTGCTGTTGAG<br>GAGGAGCTGAATAGGGTTACAGAGTTGTTTATGGATAATAAAA<br>ATGAACTTGACCAGTGTAAATCTGACCTGCAAAATAAAACACA<br>AGAACTTGAAACCACTCAAAAACATTTGCAAGAAACTAAATTA<br>CAACTTGTTAAAGAAGAATATATCACATCAGCTTTGGAAAGTA<br>CTGAGGAGAAACTTCATGATGCTGCCAGCAAGCTGCTTAACAC<br>AGTTGAAGAAACTACAAAAGATGTATCTGGTCTCCATTCCAAA<br>CTGGATCGTAAGAAGGCAGTTGACCAACACAATGCAGAAGCTC<br>AGGATATTTTTGGCAAAAACCTGAATAGTCTGTTTAATAATAT<br>GGAAGAATTAATTAAGGATGGCAGCTCAAAGCAAAAGGCCATG<br>CTAGAAGTACATAAGACCTTATTTGGTAATCTGCTGTCTTCCA<br>GTGTCTCTGCATTAGATACCATTACTACAGTAGCACTTGGATC<br>TCTCACATCTATTCCAGAAAATGTGTCTACTCATGTTTCTCAG<br>ATTTTTAATATGATACTAAAAGAACAATCATTAGCAGCAGAAA<br>GTAAAACTGTACTACAGGAATTGATTAATGTACTCAAGACTGA<br>TCTTCTAAGTTCACTGGAAATGATTTTATCCCCAACTGTGGTG<br>TCTATACTGAAAATCAATAGTCAACTAAAGCATATTTTCAAGA<br>CTTCATTGACAGTGGCCGATAAGATAGAAGATCAAAAAAAGGA<br>ACTAGATGGCTTTCTCAGTATACTGTGTAACAATCTACATGAA<br>CTACAAGAAAATACCATTTGTTCCTTGGTTGAGTCACAAAAGC<br>AATGTGGAAACCTAACTGAAGACCTGAAGACAATAAAGCAGAC<br>CCATTCCCAGGAACTTTGCAAGTTAATGAATCTTTGGACAGAG<br>AGATTCTGTGCTTTGGAGGAAAAGTGTGAAAATATACAGAAAC<br>CACTTAGTAGTGTCCAGGAAAATATACAGCAGAAATCTAAGGA<br>TATAGTCAACAAAATGACTTTTCACAGTCAAAAATTTTGTGCT<br>GATTCTGATGGCTTCTCACAGGAACTCAGAAATTTTAACCAAG<br>AAGGTACAAAATTGGTTGAAGAATCTGTGAAACACTCTGATAA<br>ACTCAATGGCAACCTGGAAAAAATATCTCAAGAGACTGAACAG<br>AGATGTGAATCTCTGAACACAAGAACAGTTTATTTTTCTGAAC<br>AGTGGGTATCTTCCTTAAATGAAAGGGAACAGGAACTTCACAA<br>CTTATTGGAGGTTGTAAGCCAATGTTGTGAGGCTTCAAGTTCA<br>GACATCACTGAGAAATCAGATGGACGTAAGGCAGCTCATGAGA<br>AACAGCATAACATTTTTCTTGATCAGATGACTATTGATGAAGA<br>TAAATTGATAGCACAAAATCTAGAACTTAATGAAACCATAAAA<br>ATTGGTTTGACTAAGCTTAATTGCTTTCTGGAACAGGATCTGA<br>AACTGGATATCCCAACAGGTACGACACCACAGAGGAAAAGTTA<br>TTTATACCCATCAACACTGGTAAGAACTGAACCACGTGAACAT<br>CTCCTTGATCAGCTGAAAAGGAAACAGCCTGAGCTGTTAATGA<br>TGCTAAACTGTTCAGAAAACAACAAAGAAGAGACAATTCCGGA<br>TGTGGATGTAGAAGAGGCAGTTCTGGGGCAGTATACTGAAGAA<br>CCTCTAAGTCAAGAGCCATCTGTAGATGCTGGTGTGGATTGTT<br>CATCAATTGGCGGGGTTCCATTTTTCCAGCATAAAAAATCACA<br>TGGAAAAGACAAAGAAAACAGAGGCATTAACACACTGGAGAGG<br>TCTAAAGTGGAAGAAACTACAGAGCACTTGGTTACAAAGAGCA<br>GATTACCTCTGCGAGCCCAGATCAACCTTTAA |
| 5 | Rous Sarcoma virus (RSV) promoter | GTAGTCTTATGCAATACTCTTGTAGTCTTGCAACATGGTAACG<br>ATGAGTTAGCAACATGCCTTACAAGGAGAGAAAAAGCACCGTG<br>CATGCCGATTGGTGGAAGTAAGGTGGTACGATCGTGCCTTATT<br>AGGAAGGCAACAGACGGGTCTGACATGGATTGGACGAACCACT<br>GAATTGCCGCATTGCAGAGATATTGTATTTAAGTGCCTAGCTC<br>GATACAATAAACG |

-continued

| SEQ ID NO: | Description | Sequence |
|---|---|---|
| 6 | 5' Long terminal repeat (LTR) | GGTCTCTCTGGTTAGACCAGATCTGAGCCTGGGAGCTCTCTGG CTAACTAGGGAACCCACTGCTTAAGCCTCAATAAAGCTTGCCT TGAGTGCTTCAAGTAGTGTGTGCCCGTCTGTTGTGTGACTCTG GTAACTAGAGATCCCTCAGACCCTTTTAGTCAGTGTGGAAAAT CTCTAGCA |
| 7 | Psi Packaging signal | TACGCCAAAAATTTTGACTAGCGGAGGCTAGAAGGAGAGAG |
| 8 | Rev response element (RRE) | AGGAGCTTTGTTCCTTGGGTTCTTGGGAGCAGCAGGAAGCACT ATGGGCGCAGCCTCAATGACGCTGACGGTACAGGCCAGACAAT TATTGTCTGGTATAGTGCAGCAGCAGAACAATTTGCTGAGGGC TATTGAGGCGCAACAGCATCTGTTGCAACTCACAGTCTGGGGC ATCAAGCAGCTCCAGGCAAGAATCCTGGCTGTGGAAAGATACC TAAAGGATCAACAGCTCC |
| 9 | Central polypurine tract (cPPT) | TTTTAAAAGAAAAGGGGGGATTGGGGGGTACAGTGCAGGGGAA AGAATAGTAGACATAATAGCAACAGACATACAAACTAAAGAAT TACAAAAACAAATTACAAAATTCAAAATTTTA |
| 10 | Polymerase ill shRNA promoters; H1 promoter | GAACGCTGACGTCATCAACCCGCTCCAAGGAATCGCGGGCCCA GTGTCACTAGGCGGGAACACCCAGCGCGCGTGCGCCCTGGCAG GAAGATGGCTGTGAGGGACAGGGGAGTGGCGCCCTGCAATATT TGCATGTCGCTATGTGTTCTGGGAAATCACCATAAACGTGAAA TGTCTTTGGATTTGGGAATCTTATAAGTTCTGTATGAGACCAC TT |
| 11 | Long WPRE sequence | AATCAACCTCTGATTACAAAATTTGTGAAAGATTGACTGGTAT TCTTAACTATGTTGCTCCTTTTACGCTATGTGGATACGCTGCT TTAATGCCTTTGTATCATGCTATTGCTTCCCGTATGGCTTTCA TTTTCTCCTCCTTGTATAAATCCTGGTTGCTGTCTCTTTATGA GGAGTTGTGGCCCGTTGTCAGGCAACGTGGCGTGGTGTGCACT GTGTTTGCTGACGCAACCCCCACTGGTTGGGGCATTGCCACCA CCTGTCAGCTCCTTTCCGGGACTTTCGCTTTCCCCCTCCCTAT TGCCACGGCGGAACTCATCGCCGCCTGCCTTGCCCGCTGCTGG ACAGGGGCTCGGCTGTTGGGCACTGACAATTCCGTGGTGTTGT CGGGGAAATCATCGTCCTTTCCTTGGCTGCTCGCCTGTGTTGC CACCTGGATTCTGCGCGGGACGTCCTTCTGCTACGTCCCTTCG GCCCTCAATCCAGCGGACCTTCCTTCCCGCGGCCTGCTGCCGG CTCTGCGGCCTCTTCCGCGTCTTCGCCTTCGCCCTCAGACGAG TCGGATCTCCCTTTGGGCCGCCTCCCCGCCT |
| 12 | 3' delta LTR | TGGAAGGGCTAATTCACTCCCAACGAAGATAAGATCTGCTTTT TGCTTGTACTGGGTCTCTCTGGTTAGACCAGATCTGAGCCTGG GAGCTCTCTGGCTAACTAGGGAACCCACTGCTTAAGCCTCAAT AAAGCTTGCCTTGAGTGCTTCAAGTAGTGTGTGCCCGTCTGTT GTGTGACTCTGGTAACTAGAGATCCCTCAGACCCTTTTAGTCA GTGTGGAAAATCTCTAGCAGTAGTAGTTCATGTCA |
| 13 | Helper/Rev; Chicken beta actin (CAG) promoter; Transcription | GCTATTACCATGGGTCGAGGTGAGCCCCACGTTCTGCTTCACT CTCCCCATCTCCCCCCCCTCCCCACCCCCAATTTTGTATTTAT TTATTTTTTAATTATTTTGTGCAGCGATGGGGGCGGGGGGGGG GGGGGCGCGCGCCAGGCGGGGCGGGGCGGGGCGAGGGGCGGGG CGGGGCGAGGCGGAGAGGTGCGGCGGCAGCCAATCAGAGCGGC GCGCTCCGAAAGTTTCCTTTTATGGCGAGGCGGCGGCGGCGGC GGCCCTATAAAAAGCGAAGCGCGCGGCGGGCG |
| 14 | Helper/Rev; HIV Gag; Viral capsid | ATGGGTGCGAGAGCGTCAGTATTAAGCGGGGGAGAATTAGATC GATGGGAAAAAATTCGGTTAAGGCCAGGGGGAAAGAAAAAATA TAAATTAAAACATATAGTATGGGCAAGCAGGGAGCTAGAACGA TTCGCAGTTAATCCTGGCCTGTTAGAAACATCAGAAGGCTGTA GACAAATACTGGGACAGCTACAACCATCCCTTCAGACAGGATC AGAAGAACTTAGATCATTATATAATACAGTAGCAACCCTCTAT TGTGTGCATCAAAGGATAGAGATAAAAGACACCAAGGAAGCTT TAGACAAGATAGAGGAAGAGCAAAACAAAAGTAAGAAAAAAGC ACAGCAAGCAGCAGCTGACACAGGACACAGCAATCAGGTCAGC CAAAATTACCCTATAGTGCAGAACATCCAGGGGCAAATGGTAC ATCAGGCCATATCACCTAGAACTTTAAATGCATGGGTAAAAGT AGTAGAAGAGAAGGCTTTCAGCCCAGAAGTGATACCCATGTTT TCAGCATTATCAGAAGGAGCCACCCCACAAGATTTAAACACCA TGCTAAACACAGTGGGGGGACATCAAGCAGCCATGCAAATGTT AAAAGAGACCATCAATGAGGAAGCTGCAGAATGGGATAGAGTG CATCCAGTGCATGCAGGGCCTATTGCACCAGGCCAGATGAGAG AACCAAGGGGAAGTGACATAGCAGGAACTACTAGTACCCTTCA GGAACAAATAGGATGGATGACACATAATCCACCTATCCCAGTA GGAGAAATCTATAAAAGATGGATAATCCTGGGATTAAATAAAA |

-continued

| SEQ ID NO: | Description | Sequence |
|---|---|---|
| | | TAGTAAGAATGTATAGCCCTACCAGCATTCTGGACATAAGACA<br>AGGACCAAAGGAACCCTTTAGAGACTATGTAGACCGATTCTAT<br>AAAACTCTAAGAGCCGAGCAAGCTTCACAAGAGGTAAAAAATT<br>GGATGACAGAAACCTTGTTGGTCCAAAATGCGAACCCAGATTG<br>TAAGACTATTTTAAAAGCATTGGGACCAGGAGCGACACTAGAA<br>GAAATGATGACAGCATGTCAGGGAGTGGGGGGACCCGGCCATA<br>AAGCAAGAGTTTTGGCTGAAGCAATGAGCCAAGTAACAAATCC<br>AGCTACCATAATGATACAGAAAGGCAATTTTAGGAACCAAAGA<br>AAGACTGTTAAGTGTTTCAATTGTGGCAAAGAAGGGCACATAG<br>CCAAAAATTGCAGGGCCCCTAGGAAAAAGGGCTGTTGGAAATG<br>TGGAAAGGAAGGACACCAAATGAAAGATTGTACTGAGAGACAG<br>GCTAATTTTTTAGGGAAGATCTGGCCTTCCCACAAGGGAAGGC<br>CAGGGAATTTTCTTCAGAGCAGACCAGAGCCAACAGCCCCACC<br>AGAAGAGAGCTTCAGGTTTGGGGAAGAGACAACAACTCCCTCT<br>CAGAAGCAGGAGCCGATAGACAAGGAACTGTATCCTTTAGCTT<br>CCCTCAGATCACTCTTTGGCAGCGACCCCTCGTCACAATAA |
| 15 | Helper/Rev; HIV Pol; Protease and reverse transcriptase | ATGAATTTGCCAGGAAGATGGAAACCAAAAATGATAGGGGGAA<br>TTGGAGGTTTTATCAAAGTAGGACAGTATGATCAGATACTCAT<br>AGAAATCTGCGGACATAAAGCTATAGGTACAGTATTAGTAGGA<br>CCTACACCTGTCAACATAATTGGAAGAAATCTGTTGACTCAGA<br>TTGGCTGCACTTTAAATTTTCCCATTAGTCCTATTGAGACTGT<br>ACCAGTAAAATTAAAGCCAGGAATGGATGGCCCAAAAGTTAAA<br>CAATGGCCATTGACAGAAGAAAAAATAAAAGCATTAGTAGAAA<br>TTTGTACAGAAATGGAAAAGGAAGGAAAAATTTCAAAAATTGG<br>GCCTGAAAATCCATACAATACTCCAGTATTTGCCATAAAGAAA<br>AAAGACAGTACTAAATGGAGAAAATTAGTAGATTTCAGAGAAC<br>TTAATAAGAGAACTCAAGATTTCTGGGAAGTTCAATTAGGAAT<br>ACCACATCCTGCAGGGTTAAAACAGAAAAAATCAGTAACAGTA<br>CTGGATGTGGGCGATGCATATTTTTCAGTTCCCTTAGATAAAG<br>ACTTCAGGAAGTATACTGCATTTACCATACCTAGTATAAACAA<br>TGAGACACCAGGGATTAGATATCAGTACAATGTGCTTCCACAG<br>GGATGGAAAGGATCACCAGCAATATTCCAGTGTAGCATGACAA<br>AAATCTTAGAGCCTTTTAGAAAACAAAATCCAGACATAGTCAT<br>CTATCAATACATGGATGATTTGTATGTAGGATCTGACTTAGAA<br>ATAGGGCAGCATAGAACAAAAATAGAGGAACTGAGACAACATC<br>TGTTGAGGTGGGGATTTACCACACCAGACAAAAAACATCAGAA<br>AGAACCTCCATTCCTTTGGATGGGTTATGAACTCCATCCTGAT<br>AAATGGACAGTACAGCCTATAGTGCTGCCAGAAAAGGACAGCT<br>GGACTGTCAATGACATACAGAAATTAGTGGGAAAATTGAATTG<br>GGCAAGTCAGATTTATGCAGGGATTAAAGTAAGGCAATTATGT<br>AAACTTCTTAGGGGAACCAAAGCACTAACAGAAGTAGTACCAC<br>TAACAGAAGAAGCAGAGCTAGAACTGGCAGAAAACAGGGAGAT<br>TCTAAAAGAACCGGTACATGGAGTGTATTATGACCCATCAAAA<br>GACTTAATAGCAGAAATACAGAAGCAGGGGCAAGGCCAATGGA<br>CATATCAAATTTATCAAGAGCCATTTAAAAATCTGAAAACAGG<br>AAAATATGCAAGAATGAAGGGTGCCCACACTAATGATGTGAAA<br>CAATTAACAGAGGCAGTACAAAAAATAGCCACAGAAAGCATAG<br>TAATATGGGGAAAGACTCCTAAATTTAAATTACCCATACAAAA<br>GGAAACATGGGAAGCATGGTGGACAGAGTATTGGCAAGCCACC<br>TGGATTCCTGAGTGGGAGTTTGTCAATACCCCTCCCTTAGTGA<br>AGTTATGGTACCAGTTAGAGAAAGAACCCATAATAGGAGCAGA<br>AACTTTCTATGTAGATGGGGCAGCCAATAGGGAAACTAAATTA<br>GGAAAAGCAGGATATGTAACTGACAGAGGAAGACAAAAAGTTG<br>TCCCCCTAACGGACACAACAAATCAGAAGACTGAGTTACAAGC<br>AATTCATCTAGCTTTGCAGGATTCGGGATTAGAAGTAAACATA<br>GTGACAGACTCACAATATGCATTGGGAATCATTCAAGCACAAC<br>CAGATAAGAGTGAATCAGAGTTAGTCAGTCAAATAATAGAGCA<br>GTTAATAAAAAAGGAAAAAGTCTACCTGGCATGGGTACCAGCA<br>CACAAAGGAATTGGAGGAAATGAACAAGTAGATGGGTTGGTCA<br>GTGCTGGAATCAGGAAAGTACTA |
| 16 | Helper Rev; HIV Integrase; Integration of viral RNA | TTTTTAGATGGAATAGATAAGGCCCAAGAAGAACATGAGAAAT<br>ATCACAGTAATTGGAGAGCAATGGCTAGTGATTTTAACCTACC<br>ACCTGTAGTAGCAAAAGAAATAGTAGCCAGCTGTGATAAATGT<br>CAGCTAAAAGGGGAAGCCATGCATGGACAAGTAGACTGTAGCC<br>CAGGAATATGGCAGCTAGATTGTACACATTTAGAAGGAAAAGT<br>TATCTTGGTAGCAGTTCATGTAGCCAGTGGATATATAGAAGCA<br>GAAGTAATTCCAGCAGAGACAGGGCAAGAAACAGCATACTTCC<br>TCTTAAAATTAGCAGGAAGATGGCCAGTAAAAACAGTACATAC<br>AGACAATGGCAGCAATTTCACCAGTACTACAGTTAAGGCCGCC<br>TGTTGGTGGGCGGGGATCAAGCAGGAATTTGGCATTCCCTACA<br>ATCCCCAAAGTCAAGGAGTAATAGAATCTATGAATAAAGAATT<br>AAAGAAAATTATAGGACAGGTAAGAGATCAGGCTGAACATCTT<br>AAGACAGCAGTACAAATGGCAGTATTCATCCACAATTTTAAAA<br>GAAAAGGGGGGATTGGGGGGTACAGTGCAGGGGAAAGAATAGT |

-continued

| SEQ ID NO: | Description | Sequence |
|---|---|---|
| | | AGACATAATAGCAACAGACATACAAACTAAAGAATTACAAAAA CAAATTACAAAAATTCAAAATTTTCGGGTTTATTACAGGGACA GCAGAGATCCAGTTTGGAAAGGACCAGCAAAGCTCCTCTGGAA AGGTGAAGGGGCAGTAGTAATACAAGATAATAGTGACATAAAA GTAGTGCCAAGAAGAAAAGCAAAGATCATCAGGGATTATGGAA AACAGATGGCAGGTGATGATTGTGTGGCAAGTAGACAGGATGA GGATTAA |
| 17 | Helper/Rev; HIV RRE; Binds Rev element | AGGAGCTTTGTTCCTTGGGTTCTTGGGAGCAGCAGGAAGCACT ATGGGCGCAGCGTCAATGACGCTGACGGTACAGGCCAGACAAT TATTGTCTGGTATAGTGCAGCAGCAGAACAATTTGCTGAGGGC TATTGAGGCGCAACAGCATCTGTTGCAACTCACAGTCTGGGGC ATCAAGCAGCTCCAGGCAAGAATCCTGGCTGTGGAAAGATACC TAAAGGATCAACAGCTCCT |
| 18 | Helper/Rev; HIV Rev; Nuclear export and stabilize viral mRNA | ATGGCAGGAAGAAGCGGAGACAGCGACGAAGAACTCCTCAAGG CAGTCAGACTCATCAAGTTTCTCTATCAAAGCAACCCACCTCC CAATCCCGAGGGGACCCGACAGGCCCGAAGGAATAGAAGAAGA AGGTGGAGAGAGAGACAGAGACAGATCCATTCGATTAGTGAAC GGATCCTTAGCACTTATCTGGGACGATCTGCGGAGCCTGTGCC TCTTCAGCTACCACCGCTTGAGAGACTTACTCTTGATTGTAAC GAGGATTGTGGAACTTCTGGGACGCAGGGGGTGGGAAGCCCTC AAATATTGGTGGAATCTCCTACAATATTGGAGTCAGGAGCTAA AGAATAG |
| 19 | Helper/Rev; CMV early (CAG) enhancer; Enhance Transcription | TAGTTATTAATAGTAATCAATTACGGGGTCATTAGTTCATAGC CCATATATGGAGTTCCGCGTTACATAACTTACGGTAAATGGCC CGCCTGGCTGACCGCCCAACGACCCCCGCCCATTGACGTCAAT AATGACGTATGTTCCCATAGTAACGCCAATAGGGACTTTCCAT TGACGTCAATGGGTGGACTATTTACGGTAAACTGCCCACTTGG CAGTACATCAAGTGTATCATATGCCAAGTACGCCCCCTATTGA CGTCAATGACGGTAAATGGCCCGCCTGGCATTATGCCCAGTAC ATGACCTTATGGGACTTTCCTACTTGGCAGTACATCTACGTAT TAGTCATC |
| 20 | Helper/Rev; Chicken beta actin intron; Enhance gene expression | GGAGTCGCTGCGTTGCCTTCGCCCCGTGCCCCGCTCCGCGCCG CCTCGCGCCGCCCGCCCCGGCTCTGACTGACCGCGTTACTCCC ACAGGTGAGCGGGCGGGACGGCCCTTCTCCTCCGGGCTGTAAT TAGCGCTTGGTTTAATGACGGCTCGTTTCTTTTCTGTGGCTGC GTGAAAGCCTTAAAGGGCTCCGGGAGGGCCCTTTGTGCGGGGG GGAGCGGCTCGGGGGGTGCGTGCGTGTGTGTGTGCGTGGGGAG CGCCGCGTGCGGCCCGCGCTGCCCGGCGGCTGTGAGCGCTGCG GGCGCGGCGCGGGGCTTTGTGCGCTCCGCGTGTGCGCGAGGGG AGCGCGGCCGGGGGCGGTGCCCCGCGGTGCGGGGGGGCTGCGA GGGGAACAAAGGCTGCGTGCGGGGTGTGTGCGTGGGGGGGTGA GCAGGGGGTGTGGGCGCGGCGGTCGGGCTGTAACCCCCCCCTG CACCCCCCTCCCCGAGTTGCTGAGCACGGCCCGGCTTCGGGTG CGGGGCTCCGTGCGGGGCGTGGCGCGGGGCTCGCCGTGCCGGG CGGGGGGTGGCGGCAGGTGGGGGTGCCGGGCGGGGCGGGGCCG CCTCGGGCCGGGGAGGGCTCGGGGGAGGGGCGCGGCGGCCCCG GAGCGCCGGCGGCTGTCGAGGCGCGGCGAGCCGCAGCCATTGC CTTTTATGGTAATCGTGCGAGAGGGCGCAGGGACTTCCTTTGT CCCAAATCTGGCGGAGCCGAAATCTGGGAGGCGCCGCCGCACC CCCTCTAGCGGGCGCGGGCGAAGCGGTGCGGCGCCGGCAGGAA GGAAATGGGCGGGGAGGGCCTTCGTGCGTCGCCGCGCCGCCGT CCCCTTCTCCATCTCCAGCCTCGGGGCTGCCGCAGGGGGACGG CTGCCTTCGGGGGGGACGGGGCAGGGCGGGGTTCGGCTTCTGG CGTGTGACCGGCGG |
| 21 | Helper/Rev; Rabbit beta globin poly A; RNA stability | AGATCTTTTTCCCTCTGCCAAAAATTATGGGGACATCATGAAG CCCCTTGAGCATCTGACTTCTGGCTAATAAAGGAAATTTATTT TCATTGCAATAGTGTGTTGGAATTTTTTGTGTCTCTCACTCGG AAGGACATATGGGAGGGCAAATCATTTAAAACATCAGAATGAG TATTTGGTTTAGAGTTTGGCAACATATGCCATATGCTGGCTGC CATGAACAAAGGTGGCTATAAAGAGGTCATCAGTATATGAAAC AGCCCCCTGCTGTCCATTCCTTATTCCATAGAAAAGCCTTGAC TTGAGGTTAGATTTTTTTTATATTTTGTTTTGTGTTATTTTTT TCTTTAACATCCCTAAAATTTTCCTTACATGTTTTACTAGCCA GATTTTTCCTCCTCTCCTGACTACTCCCAGTCATAGCTGTCCC TCTTCTCTTATGAAGATC |
| 22 | Envelope; CMV promoter; Transcription | ACATTGATTATTGACTAGTTATTAATAGTAATCAATTACGGGG TCATTAGTTCATAGCCCATATATGGAGTTCCGCGTTACATAAC TTACGGTAAATGGCCCGCCTGGCTGACCGCCCAACGACCCCCG CCCATTGACGTCAATAATGACGTATGTTCCCATAGTAACGCCA ATAGGGACTTTCCATTGACGTCAATGGGTGGAGTATTTACGGT |

-continued

| SEQ ID NO: | Description | Sequence |
|---|---|---|
| | | AAACTGCCCACTTGGCAGTACATCAAGTGTATCATATGCCAAG TACGCCCCCTATTGACGTCAATGACGGTAAATGGCCCGCCTGG CATTATGCCCAGTACATGACCTTATGGGACTTTCCTACTTGGC AGTACATCTACGTATTAGTCATCGCTATTACCATGGTGATGCG GTTTTGGCAGTACATCAATGGGCGTGGATAGCGGTTTGACTCA CGGGGATTTCCAAGTCTCCACCCCATTGACGTCAATGGGAGTT TGTTTTGGCACCAAAATCAACGGGACTTTCCAAAATGTCGTAA CAACTCCGCCCCATTGACGCAAATGGGCGGTAGGCGTGTACGG TGGGAGGTCTATATAAGC |
| 23 | Envelope; Beta globin intron; Enhance gene expression | GTGAGTTTGGGGACCCTTGATTGTTCTTTCTTTTTCGCTATTG TAAAATTCATGTTATATGGAGGGGGCAAAGTTTTCAGGGTGTT GTTTAGAATGGGAAGATGTCCCTTGTATCACCATGGACCCTCA TGATAATTTTGTTTCTTTCACTTTCTACTCTGTTGACAACCAT TGTCTCCTCTTATTTTCTTTTCATTTTCTGTAACTTTTTCGTT AAACTTTAGCTTGCATTTGTAACGAATTTTTAAATTCACTTTT GTTTATTTGTCAGATTGTAAGTACTTTCTCTAATCACTTTTTT TTCAAGGCAATCAGGGTATATTATATTGTACTTCAGCACAGTT TTAGAGAACAATTGTTATAATTAAATGATAAGGTAGAATATTT CTGCATATAAATTCTGGCTGGCGTGGAAATATTCTTATTGGTA GAAACAACTACACCCTGGTCATCATCCTGCCTTTCTCTTTATG GTTACAATGATATACACTGTTTGAGATGAGGATAAAATACTCT GAGTCCAAACCGGGCCCCTCTGCTAACCATGTTCATGCCTTCT TCTCTTTCCTACAG |
| 24 | DNA fragment containing VSV-G | GAATTCATGAAGTGCCTTTTGTACTTAGCCTTTTTATTCATTG GGGTGAATTGCAAGTTCACCATAGTTTTTCCACACAACCAAAA AGGAAACTGGAAAAATGTTCCTTCTAATTACCATTATTGCCCG TCAAGCTCAGATTTAAATTGGCATAATGACTTAATAGGCACAG CCTTACAAGTCAAAATGCCCAAGAGTCACAAGGCTATTCAAGC AGACGGTTGGATGTGTCATGCTTCCAAATGGGTCACTACTTGT GATTTCCGCTGGTATGGACCGAAGTATATAACACATTCCATCC GATCCTTCACTCCATCTGTAGAACAATGCAAGGAAAGCATTGA ACAAACGAAACAAGGAACTTGGCTGAATCCAGGCTTCCCTCCT CAAAGTTGTGGATATGCAACTGTGACGGATGCCGAAGCAGTGA TTGTCCAGGTGACTCCTCACCATGTGCTGGTTGATGAATACAC AGGAGAATGGGTTGATTCACAGTTCATCAACGGAAAATGCAGC AATTACATATGCCCCACTGTCCATAACTCTACAACCTGGCATT CTGACTATAAGGTCAAAGGGCTATGTGATTCTAACCTCATTTC CATGGACATCACCTTCTTCTCAGAGGACGGAGAGCTATCATCC CTGGGAAAGGAGGGCACAGGGTTCAGAAGTAACTACTTTGCTT ATGAAACTGGAGGCAAGGCCTGCAAAATGCAATACTGCAAGCA TTGGGGAGTCAGACTCCCATCAGGTGTCTGGTTCGAGATGGCT GATAAGGATCTCTTTGCTGCAGCCAGATTCCCTGAATGCCCAG AAGGGTCAAGTATCTCTGCTCCATCTCAGACCTCAGTGGATGT AAGTCTAATTCAGGACGTTGAGAGGATCTTGGATTATTCCCTC TGCCAAGAAACCTGGAGCAAAATCAGAGCGGGTCTTCCAATCT CTCCAGTGGATCTCAGCTATCTTGCTCCTAAAAACCCAGGAAC CGGTCCTGCTTTCACCATAATCAATGGTACCCTAAAATACTTT GAGACCAGATACATCAGAGTCGATATTGCTGCTCCAATCCTCT CAAGAATGGTCGGAATGATCAGTGGAACTACCACAGAAAGGGA ACTGTGGGATGACTGGGCACCATATGAAGACGTGGAAATTGGA CCCAATGGAGTTCTGAGGACCAGTTCAGGATATAAGTTTCCTT TATACATGATTGGACATGGTATGTTGGACTCCGATCTTCATCT TAGCTCAAAGGCTCAGGTGTTCGAACATCCTCACATTCAAGAC GCTGCTTCGCAACTTCCTGATGATGAGAGTTTATTTTTTGGTG ATACTGGGCTATCCAAAAATCCAATCGAGCTTGTAGAAGGTTG GTTCAGTAGTTGGAAAAGCTCTATTGCCTCTTTTTTCTTTATC ATAGGGTTAATCATTGGACTATTCTTGGTTCTCCGAGTTGGTA TCCATCTTTGCATTAAATTAAAGCACACCAAGAAAAGACAGAT TTATACAGACATAGAGATGAGAATTC |
| 25 | Envelope; Rabbit beta globin poly A; RNA stability | AGATCTTTTTCCCTCTGCCAAAAATTATGGGGACATCATGAAG CCCCTTGAGCATCTGACTTCTGGCTAATAAAGGAAATTTATTT TCATTGCAATAGTGTGTTGGAATTTTTTGTGTCTCTCACTCGG AAGGACATATGGGAGGGCAAATCATTTAAAACATCAGAATGAG TATTTGGTTTAGAGTTTGGCAACATATGCCCATATGCTGGCTG CCATGAACAAAGGTTGGCTATAAAGAGGTCATCAGTATATGAA ACAGCCCCCTGCTGTCCATTCCTTATTCCATAGAAAAGCCTTG ACTTGAGGTTAGATTTTTTTTATATTTTGTTTTGTGTTATTTT TTTCTTTAACATCCCTAAAATTTTCCTTACATGTTTTACTAGC CAGATTTTTCCTCCTCTCCTGACTACTCCCAGTCATAGCTGTC CCTCTTCTCTTATGGAGATC |

-continued

| SEQ ID NO: | Description | Sequence |
|---|---|---|
| 26 | Gag, Pol, Integrase fragment | GAATTCATGAATTTGCCAGGAAGATGGAAACCAAAAATGATAG<br>GGGGAATTGGAGGTTTTATCAAAGTAAGACAGTATGATCAGAT<br>ACTCATAGAAATCTGCGGACATAAAGCTATAGGTACAGTATTA<br>GTAGGACCTACACCTGTCAACATAATTGGAAGAAATCTGTTGA<br>CTCAGATTGGCTGCACTTTAAATTTTCCCATTAGTCCTATTGA<br>GACTGTACCAGTAAAATTAAAGCCAGGAATGGATGGCCCAAAA<br>GTTAAACAATGGCCATTGACAGAAGAAAAAATAAAAGCATTAG<br>TAGAAATTTGTACAGAAATGGAAAAGGAAGGAAAAATTTCAAA<br>AATTGGGCCTGAAAATCCATACAATACTCCAGTATTTGCCATA<br>AAGAAAAAAGACAGTACTAAATGGAGAAAATTAGTAGATTTCA<br>GAGAACTTAATAAGAGAACTCAAGATTTCTGGGAAGTTCAATT<br>AGGAATACCACATCCTGCAGGGTTAAAACAGAAAAAATCAGTA<br>ACAGTACTGGATGTGGGCGATGCATATTTTTCAGTTCCCTTAG<br>ATAAAGACTTCAGGAAGTATACTGCATTTACCATACCTAGTAT<br>AAACAATGAGACACCAGGGATTAGATATCAGTACAATGTGCTT<br>CCACAGGGATGGAAAGGATCACCAGCAATATTCCAGTGTAGCA<br>TGACAAAAATCTTAGAGCCTTTTAGAAAACAAAATCCAGACAT<br>AGTCATCTATCAATACATGGATGATTTGTATGTAGGATCTGAC<br>TTAGAAATAGGGCAGCATAGAACAAAAATAGAGGAACTGAGAC<br>AACATCTGTTGAGGTGGGGATTTACCACACCAGACAAAAAACA<br>TCAGAAAGAACCTCCATTCCTTTGGATGGGTTATGAACTCCAT<br>CCTGATAAATGGACAGTACAGCCTATAGTGCTGCCAGAAAAGG<br>ACAGCTGGACTGTCAATGACATACAGAAATTAGTGGGAAAATT<br>GAATTGGGCAAGTCAGATTTATGCAGGGATTAAAGTAAGGCAA<br>TTATGTAAACTTCTTAGGGGAACCAAAGCACTAACAGAAGTAG<br>TACCACTAACAGAAGAAGCAGAGCTAGAACTGGCAGAAAACAG<br>GGAGATTCTAAAAGAACCGGTACATGGAGTGTATTATGACCCA<br>TCAAAAGACTTAATAGCAGAAATACAGAAGCAGGGGCAAGGCC<br>AATGGACATATCAAATTTATCAAGAGCCATTTAAAAATCTGAA<br>AACAGGAAAGTATGCAAGAATGAAGGGTGCCCACACTAATGAT<br>GTGAAACAATTAACAGAGGCAGTACAAAAAATAGCCACAGAAA<br>GCATAGTAATATGGGGAAAGACTCCTAAATTTAAATTACCCAT<br>ACAAAAGGAAACATGGGAAGCATGGTGGACAGAGTATTGGCAA<br>GCCACCTGGATTCCTGAGTGGGAGTTTGTCAATACCCCTCCCT<br>TAGTGAAGTTATGGTACCAGTTAGAGAAAGAACCCATAATAGG<br>AGCAGAAACTTTCTATGTAGATGGGGCAGCCAATAGGGAAACT<br>AAATTAGGAAAAGCAGGATATGTAACTGACAGAGGAAGACAAA<br>AAGTTGTCCCCCTAACGGACACAACAAATCAGAAGACTGAGTT<br>ACAAGCAATTCATCTAGCTTTGCAGGATTCGGGATTAGAAGTA<br>AACATAGTGACAGACTCACAATATGCATTGGGAATCATTCAAG<br>CACAACCAGATAAGAGTGAATCAGAGTTAGTCAGTCAAATAAT<br>AGAGCAGTTAATAAAAAAGGAAAAAGTCTACCTGGCATGGGTA<br>CCAGCACACAAAGGAATTGGAGGAAATGAACAAGTAGATAAAT<br>TGGTCAGTGCTGGAATCAGGAAAGTACTATTTTTAGATGGAAT<br>AGATAAGGCCCAAGAAGAACATGAGAAATATCACAGTAATTGG<br>AGAGCAATGGCTAGTGATTTTAACCTACCACCTGTAGTAGCAA<br>AAGAAATAGTAGCCAGCTGTGATAAATGTCAGCTAAAAGGGGA<br>AGCCATGCATGGACAAGTAGACTGTAGCCCAGGAATATGGCAG<br>CTAGATTGTACACATTTAGAAGGAAAAGTTATCTTGGTAGCAG<br>TTCATGTAGCCAGTGGATATATAGAAGCAGAAGTAATTCCAGC<br>AGAGACAGGGCAAGAAACAGCATACTTCCTCTTAAAATTAGCA<br>GGAAGATGGCCAGTAAAAACAGTACATACAGACAATGGCAGCA<br>ATTTCACCAGTACTACAGTTAAGGCCGCCTGTTGGTGGGCGGG<br>GATCAAGCAGGAATTTGGCATTCCCTACAATCCCCAAAGTCAA<br>GGAGTAATAGAATCTATGAATAAAGAATTAAAGAAAATTATAG<br>GACAGGTAAGAGATCAGGCTGAACATCTTAAGACAGCAGTACA<br>AATGGCAGTATTCATCCACAATTTTAAAAGAAAAGGGGGGATT<br>GGGGGGTACAGTGCAGGGGAAAGAATAGTAGACATAATAGCAA<br>CAGACATACAAACTAAAGAATTACAAAAACAAATTACAAAAAT<br>TCAAAATTTTCGGGTTTATTACAGGGACAGCAGAGATCCAGTT<br>TGGAAAGGACCAGCAAAGCTCCTCTGGAAAGGTGAAGGGGCAG<br>TAGTAATACAAGATAATAGTGACATAAAAGTAGTGCCAAGAAG<br>AAAAGCAAAGATCATCAGGGATTATGGAAAACAGATGGCAGGT<br>GATGATTGTGTGGCAAGTAGACAGGATGAGGATTAA |
| 27 | DNA Fragment containing Rev, RRE and rabbit beta globin poly A | TCTAGAATGGCAGGAAGAAGCGGAGACAGCGACGAAGAGCTCA<br>TCAGAACAGTCAGACTCATCAAGCTTCTCTATCAAAGCAACCC<br>ACCTCCCAATCCCGAGGGGACCCGACAGGCCCGAAGGAATAGA<br>AGAAGAAGGTGGAGAGAGAGACAGAGACAGATCCATTCGATTA<br>GTGAACGGATCCTTGGCACTTATCTGGGACGATCTGCGGAGCC<br>TGTGCCTCTTCAGCTACCACCGCTTGAGAGACTTACTCTTGAT<br>TGTAACGAGGATTGTGGAACTTCTGGGACGCAGGGGGTGGGAA<br>GCCCTCAAATATTGGTGGAATCTCCTACAATATTGGAGTCAGG<br>AGCTAAAGAATAGAGGAGCTTTGTTCCTTGGGTTCTTGGGAGC<br>AGCAGGAAGCACTATGGGCGCAGCGTCAATGACGCTGACGGTA |

-continued

| SEQ ID NO: | Description | Sequence |
|---|---|---|
| | | CAGGCCAGACAATTATTGTCTGGTATAGTGCAGCAGCAGAACA<br>ATTTGCTGAGGGCTATTGAGGCGCAACAGCATCTGTTGCAACT<br>CACAGTCTGGGGCATCAAGCAGCTCCAGGCAAGAATCCTGGCT<br>GTGGAAAGATACCTAAAGGATCAACAGCTCCTAGATCTTTTTC<br>CCTCTGCCAAAAATTATGGGGACATCATGAAGCCCCTTGAGCA<br>TCTGACTTCTGGCTAATAAAGGAAATTTATTTTCATTGCAATA<br>GTGTGTTGGAATTTTTTGTGTCTCTCACTCGGAAGGACATATG<br>GGAGGGCAAATCATTTAAAACATCAGAATGAGTATTTGGTTTA<br>GAGTTTGGCAACATATGCCATATGCTGGCTGCCATGAACAAAG<br>GTGGCTATAAAGAGGTCATCAGTATATGAAACAGCCCCCTGCT<br>GTCCATTCCTTATTCCATAGAAAAGCCTTGACTTGAGGTTAGA<br>TTTTTTTTATATTTTGTTTTGTGTTATTTTTTTCTTTAACATC<br>CCTAAAATTTTCCTTACATGTTTTACTAGCCAGATTTTTCCTC<br>CTCTCCTGACTACTCCCAGTCATAGCTGTCCCTCTTCTCTTAT<br>GAAGATCCCTCGACCTGCAGCCCAAGCTTGGCGTAATCATGGT<br>CATAGCTGTTTCCTGTGTGAAATTGTTATCCGCTCACAATTCC<br>ACACAACATACGAGCCGGAAGCATAAAGTGTAAAGCCTGGGGT<br>GCCTAATGAGTGAGCTAACTCACATTAATTGCGTTGCGCTCAC<br>TGCCCGCTTTCCAGTCGGGAAACCTGTCGTGCCAGCGGATCCG<br>CATCTCAATTAGTCAGCAACCATAGTCCCGCCCCTAACTCCGC<br>CCATCCCGCCCCTAACTCCGCCCAGTTCCGCCCATTCTCCGCC<br>CCATGGCTGACTAATTTTTTTTATTTATGCAGAGGCCGAGGCC<br>GCCTCGGCCTCTGAGCTATTCCAGAAGTAGTGAGGAGGCTTTT<br>TTGGAGGCCTAGGCTTTTGCAAAAAGCTAACTTGTTTATTGCA<br>GCTTATAATGGTTACAAATAAAGCAATAGCATCACAAATTTCA<br>CAAATAAAGCATTTTTTTCACTGCATTCTAGTTGTGGTTTGTC<br>CAAACTCATCAATGTATCTTATCAGCGGCCGCCCCGGG |
| 28 | DNA fragment containing the CAG enhancer/promoter/ intron sequence | ACGCGTTAGTTATTAATAGTAATCAATTACGGGGTCATTAGTT<br>CATAGCCCATATATGGAGTTCCGCGTTACATAACTTACGGTAA<br>ATGGCCCGCCTGGCTGACCGCCCAACGACCCCCGCCCATTGAC<br>GTCAATAATGACGTATGTTCCCATAGTAACGCCAATAGGGACT<br>TTCCATTGACGTCAATGGGTGGACTATTTACGGTAAACTGCCC<br>ACTTGGCAGTACATCAAGTGTATCATATGCCAAGTACGCCCCC<br>TATTGACGTCAATGACGGTAAATGGCCCGCCTGGCATTATGCC<br>CAGTACATGACCTTATGGGACTTTCCTACTTGGCAGTACATCT<br>ACGTATTAGTCATCGCTATTACCATGGGTCGAGGTGAGCCCCA<br>CGTTCTGCTTCACTCTCCCCATCTCCCCCCCCTCCCCACCCCC<br>AATTTTGTATTTATTTATTTTTTAATTATTTTGTGCAGCGATG<br>GGGGCGGGGGGGGGGGGGGCGCGCGCCAGGCGGGGCGGGGCGG<br>GGCGAGGGGCGGGGCGGGGCGAGGCGGAGAGGTGCGGCGGCAG<br>CCAATCAGAGCGGCGCGCTCCGAAAGTTTCCTTTTATGGCGAG<br>GCGGCGGCGGCGGCGGCCCTATAAAAAGCGAAGCGCGCGGCGG<br>GCGGGAGTCGCTGCGTTGCCTTCGCCCCGTGCCCCGCTCCGCG<br>CCGCCTCGCGCCGCCCGCCCCGGCTCTGACTGACCGCGTTACT<br>CCCACAGGTGAGCGGGCGGGACGGCCCTTCTCCTCCGGGCTGT<br>AATTAGCGCTTGGTTTAATGACGGCTCGTTTCTTTTCTGTGGC<br>TGCGTGAAAGCCTTAAAGGGCTCCGGGAGGGCCCTTTGTGCGG<br>GGGGGAGCGGCTCGGGGGGTGCGTGCGTGTGTGTGTGCGTGGG<br>GAGCGCCGCGTGCGGCCCGCGCTGCCCGGCGGCTGTGAGCGCT<br>GCGGGCGCGGCGCGGGGCTTTGTGCGCTCCGCGTGTGCGCGAG<br>GGGAGCGCGGCCGGGGGCGGTGCCCCGCGGTGCGGGGGGGCTG<br>CGAGGGGAACAAAGGCTGCGTGCGGGGTGTGTGCGTGGGGGGG<br>TGAGCAGGGGGTGTGGGCGCGGCGGTCGGGCTGTAACCCCCCC<br>CTGCACCCCCCTCCCCGAGTTGCTGAGCACGGCCCGGCTTCGG<br>GTGCGGGGCTCCGTGCGGGGCGTGGCGCGGGGCTCGCCGTGCC<br>GGGCGGGGGGTGGCGGCAGGTGGGGGTGCCGGGCGGGGCGGGG<br>CCGCCTCGGGCCGGGGAGGGCTCGGGGGAGGGGCGCGGCGGCC<br>CCGGAGCGCCGGCGGCTGTCGAGGCGCGGCGAGCCGCAGCCAT<br>TGCCTTTTATGGTAATCGTGCGAGAGGGCGCAGGGACTTCCTT<br>TGTCCCAAATCTGGCGGAGCCGAAATCTGGGAGGCGCCGCCGC<br>ACCCCCTCTAGCGGGCGCGGGCGAAGCGGTGCGGCGCCGGCAG<br>GAAGGAAATGGGCGGGGAGGGCCTTCGTGCGTCGCCGCGCCGC<br>CGTCCCCTTCTCCATCTCCAGCCTCGGGGCTGCCGCAGGGGGA<br>CGGCTGCCTTCGGGGGGGACGGGGCAGGGCGGGGTTCGGCTTC<br>TGGCGTGTGACCGGCGGGAATTC |
| 29 | RSV promoter and HIV Rev | CAATTGCGATGTACGGGCCAGATATACGCGTATCTGAGGGGAC<br>TAGGGTGTGTTTAGGCGAAAAGCGGGGCTTCGGTTGTACGCGG<br>TTAGGAGTCCCCTCAGGATATAGTAGTTTCGCTTTTGCATAGG<br>GAGGGGGAAATGTAGTCTTATGCAATACACTTGTAGTCTTGCA<br>ACATGGTAACGATGAGTTAGCAACATGCCTTACAAGGAGAGAA<br>AAAGCACCGTGCATGCCGATTGGTGGAAGTAAGGTGGTACGAT<br>CGTGCCTTATTAGGAAGGCAACAGACAGGTCTGACATGGATTG<br>GACGAACCACTGAATTCCGCATTGCAGAGATAATTGTATTTAA<br>GTGCCTAGCTCGATACAATAAACGCCATTTGACCATTCACCAC |

-continued

| SEQ ID NO: | Description | Sequence |
|---|---|---|
| | | ATTGGTGTGCACCTCCAAGCTCGAGCTCGTTTAGTGAACCGTC<br>AGATCGCCTGGAGACGCCATCCACGCTGTTTTGACCTCCATAG<br>AAGACACCGGGACCGATCCAGCCTCCCCTCGAAGCTAGCGATT<br>AGGCATCTCCTATGGCAGGAAGAAGCGGAGACAGCGACGAAGA<br>ACTCCTCAAGGCAGTCAGACTCATCAAGTTTCTCTATCAAAGC<br>AACCCACCTCCCAATCCCGAGGGGACCCGACAGGCCCGAAGGA<br>ATAGAAGAAGAAGGTGGAGAGAGAGACAGAGACAGATCCATTC<br>GATTAGTGAACGGATCCTTAGCACTTATCTGGGACGATCTGCG<br>GAGCCTGTGCCTCTTCAGCTACCACCGCTTGAGAGACTTACTC<br>TTGATTGTAACGAGGATTGTGGAACTTCTGGGACGCAGGGGGT<br>GGGAAGCCCTCAAATATTGGTGGAATCTCCTACAATATTGGAG<br>TCAGGAGCTAAAGAATAGTCTAGA |
| 30 | RRE/rabbit poly A beta globin | TCTAGAAGGAGCTTTGTTCCTTGGGTTCTTGGGAGCAGCAGGA<br>AGCACTATGGGCGCAGCGTCAATGACGCTGACGGTACAGGCCA<br>GACAATTATTGTCTGGTATAGTGCAGCAGCAGAACAATTTGCT<br>GAGGGCTATTGAGGCGCAACAGCATCTGTTGCAACTCACAGTC<br>TGGGGCATCAAGCAGCTCCAGGCAAGAATCCTGGCTGTGGAAA<br>GATACCTAAAGGATCAACAGCTCCTAGATCTTTTTCCCTCTGC<br>CAAAAATTATGGGGACATCATGAAGCCCCTTGAGCATCTGACT<br>TCTGGCTAATAAAGGAAATTTATTTTCATTGCAATAGTGTGTT<br>GGAATTTTTTGTGTCTCTCACTCGGAAGGACATATGGGAGGGC<br>AAATCATTTAAAACATCAGAATGAGTATTTGGTTTAGAGTTTG<br>GCAACATATGCCATATGCTGGCTGCCATGAACAAAGGTGGCTA<br>TAAAGAGGTCATCAGTATATGAAACAGCCCCCTGCTGTCCATT<br>CCTTATTCCATAGAAAAGCCTTGACTTGAGGTTAGATTTTTTT<br>TATATTTTGTTTTGTGTTATTTTTTTCTTTAACATCCCTAAAA<br>TTTTCCTTACATGTTTTACTAGCCAGATTTTTCCTCCTCTCCT<br>GACTACTCCCAGTCATAGCTGTCCCTCTTCTCTTATGAAGATC<br>CCTCGACCTGCAGCCCAAGCTTGGCGTAATCATGGTCATAGCT<br>GTTTCCTGTGTGAAATTGTTATCCGCTCACAATTCCACACAAC<br>ATACGAGCCGGAAGCATAAAGTGTAAAGCCTGGGGTGCCTAAT<br>GAGTGAGCTAACTCACATTAATTGCGTTGCGCTCACTGCCCGC<br>TTTCCAGTCGGGAAACCTGTCGTGCCAGCGGATCCGCATCTCA<br>ATTAGTCAGCAACCATAGTCCCGCCCCTAACTCCGCCCATCCC<br>GCCCCTAACTCCGCCCAGTTCCGCCCATTCTCCGCCCCATGGC<br>TGACTAATTTTTTTTATTTATGCAGAGGCCGAGGCCGCCTCGG<br>CCTCTGAGCTATTCCAGAAGTAGTGAGGAGGCTTTTTTGGAGG<br>CCTAGGCTTTTGCAAAAAGCTAACTTGTTTATTGCAGCTTATA<br>ATGGTTACAAATAAAGCAATAGCATCACAAATTTCACAAATAA<br>AGCATTTTTTTCACTGCATTCTAGTTGTGGTTTGTCCAAACTC<br>ATCAATGTATCTTATCACCCGGG |
| 31 | Elongation Factor-1 alpha (EF1-alpha) promoter | CCGGTGCCTAGAGAAGGTGGCGCGGGGTAAACTGGAAAGTGA<br>TGTCGTGTACTGGCTCCGCCTTTTTCCCGAGGGTGGGGGAGAA<br>CCGTATATAAGTGCAGTAGTCGCCGTGAACGTTCTTTTTCGCA<br>ACGGGTTTGCCGCCAGAACACAGGTAAGTGCCGTGTGTGGTTC<br>CCGCGGGCCTGGCCTCTTTACGGGTTATGGCCCTTGCGTGCCT<br>TGAATTACTTCCACGCCCCTGGCTGCAGTACGTGATTCTTGAT<br>CCCGAGCTTCGGGTTGGAAGTGGGTGGGAGAGTTCGAGGCCTT<br>GCGCTTAAGGAGCCCCTTCGCCTCGTGCTTGAGTTGAGGCCTG<br>GCCTGGGCGCTGGGGCCGCCGCGTGCGAATCTGGTGGCACCTT<br>CGCGCCTGTCTCGCTGCTTTCGATAAGTCTCTAGCCATTTAAA<br>ATTTTTGATGACCTGCTGCGACGCTTTTTTTCTGGCAAGATAG<br>TCTTGTAAATGCGGGCCAAGATCTGCACACTGGTATTTCGGTT<br>TTTGGGGCCGCGGGCGGCGACGGGGCCCGTGCGTCCCAGCGCA<br>CATGTTCGGCGAGGCGGGGCCTGCGAGCGCGGCCACCGAGAAT<br>CGGACGGGGGTAGTCTCAAGCTGGCCGGCCTGCTCTGGTGCCT<br>GGCCTCGCGCCGCCGTGTATCGCCCCGCCCTGGGCGGCAAGGC<br>TGGCCCGGTCGGCACCAGTTGCGTGAGCGGAAAGATGGCCGCT<br>TCCCGGCCCTGCTGCAGGGAGCTCAAAATGGAGGACGCGGCGC<br>TCGGGAGAGCGGGCGGGTGAGTCACCCACACAAAGGAAAAGGG<br>CCTTTCCGTCCTCAGCCGTCGCTTCATGTGACTCCACGGAGTA<br>CCGGGCGCCGTCCAGGCACCTCGATTAGTTCTCGAGCTTTTGG<br>AGTACGTCGTCTTTAGGTTGGGGGGAGGGGTTTTATGCGATGG<br>AGTTTCCCCACACTGAGTGGGTGGAGACTGAAGTTAGGCCAGC<br>TTGGCACTTGATGTAATTCTCCTTGGAATTTGCCCTTTTTGAG<br>TTTGGATCTTGGTTCATTCTCAAGCCTCAGACAGTGGTTCAAA<br>GTTTTTTTCTTCCATTTCAGGTGTCGTGA |
| 32 | Promoter; PGK | GGGGTTGGGGTTGCGCCTTTTCCAAGGCAGCCCTGGGTTTGCG<br>CAGGGACGCGGCTGCTCTGGGCGTGGTTCCGGGAAACGCAGCG<br>GCGCCGACCCTGGGTCTCGCACATTCTTCACGTCCGTTCGCAG<br>CGTCACCCGGATCTTCGCCGCTACCCTTGTGGGCCCCCCGGCG<br>ACGCTTCCTGCTCCGCCCCTAAGTCGGGAAGGTTCCTTGCGGT<br>TCGCGGCGTGCCGGACGTGACAAACGGAAGCCGCACGTCTCAC |

-continued

| SEQ ID NO: | Description | Sequence |
|---|---|---|
| | | TAGTACCCTCGCAGACGGACAGCGCCAGGGAGCAATGGCAGCG CGCCGACCGCGATGGGCTGTGGCCAATAGCGGCTGCTCAGCAG GGCGCGCCGAGAGCAGCGGCCGGGAAGGGGCGGTGCGGGAGGC GGGGTGTGGGGCGGTAGTGTGGGCCCTGTTCCTGCCCGCGCGG TGTTCCGCATTCTGCAAGCCTCCGGAGCGCACGTCGGCAGTCG GCTCCCTCGTTGACCGAATCACCGACCTCTCTCCCCAG |
| 33 | Promoter; UbC | GCGCCGGGTTTTGGCGCCTCCCGCGGGCGCCCCCCTCCTCACG GCGAGCGCTGCCACGTCAGACGAAGGGCGCAGGAGCGTTCCTG ATCCTTCCGCCCGGACGCTCAGGACAGCGGCCCGCTGCTCATA AGACTCGGCCTTAGAACCCCAGTATCAGCAGAAGGACATTTTA GGACGGGACTTGGGTGACTCTAGGGCACTGGTTTTCTTTCCAG AGAGCGGAACAGGCGAGGAAAAGTAGTCCCTTCTCGGCGATTC TGCGGAGGGATCTCCGTGGGGCGGTGAACGCCGATGATTATAT AAGGACGCGCCGGGTGTGGCACAGCTAGTTCCGTCGCAGCCGG GATTTGGGTCGCGGTTCTTGTTTGTGGATCGCTGTGATCGTCA CTTGGTGAGTTGCGGGCTGCTGGGCTGGCCGGGGCTTTCGTGG CCGCCGGGCCGCTCGGTGGGACGGAAGCGTGTGGAGAGACCGC CAAGGGCTGTAGTCTGGGTCCGCGAGCAAGGTTGCCCTGAACT GGGGGTTGGGGGGAGCGCACAAAATGGCGGCTGTTCCCGAGTC TTGAATGGAAGACGCTTGTAAGGCGGGCTGTGAGGTCGTTGAA ACAAGGTGGGGGGCATGGTGGGCGGCAAGAACCCAAGGTCTTG AGGCCTTCGCTAATGCGGGAAAGCTCTTATTCGGGTGAGATGG GCTGGGGCACCATCTGGGGACCCTGACGTGAAGTTTGTCACTG ACTGGAGAACTCGGGTTTGTCGTCTGGTTGCGGGGGCGGCAGT TATGCGGTGCCGTTGGGCAGTGCACCCGTACCTTTGGGAGCGC GCGCCTCGTCGTGTCGTGACGTCACCCGTTCTGTTGGCTTATA ATGCAGGGTGGGGCCACCTGCCGGTAGGTGTGCGGTAGGCTTT TCTCCGTCGCAGGACGCAGGGTTCGGGCCTAGGGTAGGCTCTC CTGAATCGACAGGCGCCGGACCTCTGGTGAGGGGAGGGATAAG TGAGGCGTCAGTTTCTTTGGTCGGTTTTATGTACCTATCTTCT TAAGTAGCTGAAGCTCCGGTTTTGAACTATGCGCTCGGGGTTG GCGAGTGTGTTTTGTGAAGTTTTTTAGGCACCTTTTGAAATGT AATCATTTGGGTCAATATGTAATTTTCAGTGTTAGACTAGTAA A |
| 34 | Poly A; SV40 | GTTTATTGCAGCTTATAATGGTTACAAATAAAGCAATAGCATC ACAAATTTCACAAATAAAGCATTTTTTTCACTGCATTCTAGTT GTGGTTTGTCCAAACTCATCAATGTATCTTATCA |
| 35 | Poly A; bGH | GACTGTGCCTTCTAGTTGCCAGCCATCTGTTGTTTGCCCCTCC CCCGTGCCTTCCTTGACCCTGGAAGGTGCCACTCCCACTGTCC TTTCCTAATAAAATGAGGAAATTGCATCGCATTGTCTGAGTAG GTGTCATTCTATTCTGGGGGGTGGGGTGGGGCAGGACAGCAAG GGGGAGGATTGGGAAGACAATAGCAGGCATGCTGGGGATGCGG TGGGCTCTATGG |
| 36 | Envelope; RD 114 | ATGAAACTCCCAACAGGAATGGTCATTTTATGTAGCCTAATAA TAGTTCGGGCAGGGTTTGACGACCCCCGCAAGGCTATCGCATT AGTACAAAAACAACATGGTAAACCATGCGAATGCAGCGGAGGG CAGGTATCCGAGGCCCCACCGAACTCCATCCAACAGGTAACTT GCCCAGGCAAGACGGCCTACTTAATGACCAACCAAAAATGGAA ATGCAGAGTCACTCCAAAAAATCTCACCCCTAGCGGGGGAGAA CTCCAGAACTGCCCCTGTAACACTTTCCAGGACTCGATGCACA GTTCTTGTTATACTGAATACCGGCAATGCAGGGCGAATAATAA GACATACTACACGGCCACCTTGCTTAAAATACGGTCTGGGAGC CTCAACGAGGTACAGATATTACAAAACCCCAATCAGCTCCTAC AGTCCCCTTGTAGGGGCTCTATAAATCAGCCCGTTTGCTGGAG TGCCACAGCCCCCATCCATATCTCCGATGGTGGAGGACCCCTC GATACTAAGAGAGTGTGGACAGTCCAAAAAAGGCTAGAACAAA TTCATAAGGCTATGCATCCTGAACTTCAATACCACCCCTTAGC CCTGCCCAAAGTCAGAGATGACCTTAGCCTTGATGCACGGACT TTTGATATCCTGAATACCACTTTTAGGTTACTCCAGATGTCCA ATTTTAGCCTTGCCCAAGATTGTTGGCTCTGTTTAAAACTAGG TACCCCTACCCCTCTTGCGATACCCACTCCCTCTTTAACCTAC TCCCTAGCAGACTCCCTAGCGAATGCCTCCTGTCAGATTATAC CTCCCCTCTTGGTTCAACCGATGCAGTTCTCCAACTCGTCCTG TTTATCTTCCCCTTTCATTAACGATACGGAACAAATAGACTTA GGTGCAGTCACCTTTACTAACTGCACCTCTGTAGCCAATGTCA GTAGTCCTTTATGTGCCCTAAACGGGTCAGTCTTCCTCTGTGG AAATAACATGGCATACACCTATTTACCCCAAAACTGGACAGGA CTTTGCGTCCAAGCCTCCCTCCTCCCCGACATTGACATCATCC CGGGGGATGAGCCAGTCCCCATTCCTGCCATTGATCATTATAT ACATAGACCTAAACGAGCTGTACAGTTCATCCCTTTACTAGCT GGACTGGGAATCACCGCAGCATTCACCACCGGAGCTACAGGCC TAGGTGTCTCCGTCACCCAGTATACAAAATTATCCCATCAGTT |

-continued

| SEQ ID NO: | Description | Sequence |
|---|---|---|
| | | AATATCTGATGTCCAAGTCTTATCCGGTACCATACAAGATTTA<br>CAAGACCAGGTAGACTCGTTAGCTGAAGTAGTTCTCCAAAATA<br>GGAGGGGACTGGACCTACTAACGGCAGAACAAGGAGGAATTTG<br>TTTAGCCTTACAAGAAAAATGCTGTTTTTATGCTAACAAGTCA<br>GGAATTGTGAGAAACAAAATAAGAACCCTACAAGAAGAATTAC<br>AAAAACGCAGGGAAAGCCTGGCATCCAACCCTCTCTGGACCGG<br>GCTGCAGGGCTTTCTTCCGTACCTCCTACCTCTCCTGGGACCC<br>CTACTCACCCTCCTACTCATACTAACCATTGGGCCATGCGTTT<br>TCAATCGATTGGTCCAATTTGTTAAAGACAGGATCTCAGTGGT<br>CCAGGCTCTGGTTTTGACTCAGCAATATCACCAGCTAAAACCC<br>ATAGAGTACGAGCCATGA |
| 37 | Envelope; GALV | ATGCTTCTCACCTCAAGCCCGCACCACCTTCGGCACCAGATGA<br>GTCCTGGGAGCTGGAAAAGACTGATCATCCTCTTAAGCTGCGT<br>ATTCGGAGACGGCAAAACGAGTCTGCAGAATAAGAACCCCCAC<br>CAGCCTGTGACCCTCACCTGGCAGGTACTGTCCCAAACTGGGG<br>ACGTTGTCTGGGACAAAAAGGCAGTCCAGCCCCTTTGGACTTG<br>GTGGCCCTCTCTTACACCTGATGTATGTGCCCTGGCGGCCGGT<br>CTTGAGTCCTGGGATATCCCGGGATCCGATGTATCGTCCTCTA<br>AAAGAGTTAGACCTCCTGATTCAGACTATACTGCCGCTTATAA<br>GCAAATCACCTGGGGAGCCATAGGGTGCAGCTACCCTCGGGCT<br>AGGACCAGGATGGCAAATTCCCCCTTCTACGTGTGTCCCCGAG<br>CTGGCCGAACCCATTCAGAAGCTAGGAGGTGTGGGGGGCTAGA<br>ATCCCTATACTGTAAAGAATGGAGTTGTGAGACCACGGGTACC<br>GTTTATTGGCAACCCAAGTCCTCATGGGACCTCATAACTGTAA<br>AATGGGACCAAAATGTGAAATGGGAGCAAAAATTTCAAAAGTG<br>TGAACAAACCGGCTGGTGTAACCCCCTCAAGATAGACTTCACA<br>GAAAAAGGAAAACTCTCCAGAGATTGGATAACGGAAAAAACCT<br>GGGAATTAAGGTTCTATGTATATGGACACCCAGGCATACAGTT<br>GACTATCCGCTTAGAGGTCACTAACATGCCGGTTGTGGCAGTG<br>GGCCCAGACCCTGTCCTTGCGGAACAGGGACCTCCTAGCAAGC<br>CCCTCACTCTCCCTCTCTCCCCACGGAAAGCGCCGCCCACCCC<br>TCTACCCCCGGCGGCTAGTGAGCAAACCCCTGCGGTGCATGGA<br>GAAACTGTTACCCTAAACTCTCCGCCTCCCACCAGTGGCGACC<br>GACTCTTTGGCCTTGTGCAGGGGGCCTTCCTAACCTTGAATGC<br>TACCAACCCAGGGGCCACTAAGTCTTGCTGGCTCTGTTTGGGC<br>ATGAGCCCCCCTTATTATGAAGGGATAGCCTCTTCAGGAGAGG<br>TCGCTTATACCTCCAACCATACCCGATGCCACTGGGGGGCCCA<br>AGGAAAGCTTACCCTCACTGAGGTCTCCGGACTCGGGTCATGC<br>ATAGGGAAGGTGCCTCTTACCCATCAACATCTTTGCAACCAGA<br>CCTTACCCATCAATTCCTCTAAAAACCATCAGTATCTGCTCCC<br>CTCAAACCATAGCTGGTGGGCCTGCAGCACTGGCCTCACCCCC<br>TGCCTCTCCACCTCAGTTTTTAATCAGTCTAAAGACTTCTGTG<br>TCCAGGTCCAGCTGATCCCCCGCATCTATTACCATTCTGAAGA<br>AACCTTGTTACAAGCCTATGACAAATCACCCCCCAGGTTTAAA<br>AGAGAGCCTGCCTCACTTACCCTAGCTGTCTTCCTGGGGTTAG<br>GGATTGCGGCAGGTATAGGTACTGGCTCAACCGCCCTAATTAA<br>AGGGCCCATAGACCTCCAGCAAGGCCTAACCAGCCTCCAAATC<br>GCCATTGACGCTGACCTCCGGGCCCTTCAGGACTCAATCAGCA<br>AGCTAGAGGACTCACTGACTTCCCTATCTGAGGTAGTACTCCA<br>AAATAGGAGAGGCCTTGACTTACTATTCCTTAAAGAAGGAGGC<br>CTCTGCGCGGCCCTAAAAGAAGAGTGCTGTTTTTATGTAGACC<br>ACTCAGGTGCAGTACGAGACTCCATGAAAAAACTTAAAGAAAG<br>ACTAGATAAAAGACAGTTAGAGCGCCAGAAAAACCAAAACTGG<br>TATGAAGGGTGGTTCAATAACTCCCCTTGGTTTACTACCCTAC<br>TATCAACCATCGCTGGGCCCCTATTGCTCCTCCTTTTGTTACT<br>CACTCTTGGGCCCTGCATCATCAATAAATTAATCCAATTCATC<br>AATGATAGGATAAGTGCAGTCAAAATTTTAGTCCTTAGACAGA<br>AATATCAGACCCTAGATAACGAGGAAAACCTTTAA |
| 38 | Envelope; FUG | ATGGTTCCGCAGGTTCTTTTGTTTGTACTCCTTCTGGGTTTTT<br>CGTTGTGTTTCGGGAAGTTCCCCATTTACACGATACCAGACGA<br>ACTTGGTCCCTGGAGCCCTATTGACATACACCATCTCAGCTGT<br>CCAAATAACCTGGTTGTGGAGGATGAAGGATGTACCAACCTGT<br>CCGAGTTCTCCTACATGGAACTCAAAGTGGGATACATCTCAGC<br>CATCAAAGTGAACGGGTTCACTTGCACAGGTGTTGTGACAGAG<br>GCAGAGACCTACACCAACTTTGTTGGTTATGTCACAACCACAT<br>TCAAGAGAAAGCATTTCCGCCCCACCCCAGACGCATGTAGAGC<br>CGCGTATAACTGGAAGATGGCCGGTGACCCCAGATATGAAGAG<br>TCCCTACACAATCCATACCCCGACTACCACTGGCTTCGAACTG<br>TAAGAACCACCAAAGAGTCCCTCATTATCATATCCCCAAGTGT<br>GACAGATTTGGACCCATATGACAAATCCCTTCACTCAAGGGTC<br>TTCCCTGGCGGAAAGTGCTCAGGAATAACGGTGTCCTCTACCT<br>ACTGCTCAACTAACCATGATTACACCATTTGGATGCCCGAGAA<br>TCCGAGACCAAGGACACCTTGTGACATTTTTACCAATAGCAGA<br>GGGAAGAGAGCATCCAACGGGAACAAGACTTGCGGCTTTGTGG |

-continued

| SEQ ID NO: | Description | Sequence |
|---|---|---|
| | | ATGAAAGAGGCCTGTATAAGTCTCTAAAAGGAGCATGCAGGCT<br>CAAGTTATGTGGAGTTCTTGGACTTAGACTTATGGATGGAACA<br>TGGGTCGCGATGCAAACATCAGATGAGACCAAATGGTGCCCTC<br>CAGATCAGTTGGTGAATTTGCACGACTTTCGCTCAGACGAGAT<br>CGAGCATCTCGTTGTGGAGGAGTTAGTTAAGAAAAGAGAGGAA<br>TGTCTGGATGCATTAGAGTCCATCATGACCACCAAGTCAGTAA<br>GTTTCAGACGTCTCAGTCACCTGAGAAAACTTGTCCCAGGGTT<br>TGGAAAAGCATATACCATATTCAACAAAACCTTGATGGAGGCT<br>GATGCTCACTACAAGTCAGTCCGGACCTGGAATGAGATCATCC<br>CCTCAAAAGGGTGTTTGAAAGTTGGAGGAAGGTGCCATCCTCA<br>TGTGAACGGGGTGTTTTTCAATGGTATAATATTAGGGCCTGAC<br>GACCATGTCCTAATCCCAGAGATGCAATCATCCCTCCTCCAGC<br>AACATATGGAGTTGTTGGAATCTTCAGTTATCCCCCTGATGCA<br>CCCCCTGGCAGACCCTTCTACAGTTTTCAAAGAAGGTGATGAG<br>GCTGAGGATTTTGTTGAAGTTCACCTCCCCGATGTGTACAAAC<br>AGATCTCAGGGGTTGACCTGGGTCTCCCGAACTGGGGAAAGTA<br>TGTATTGATGACTGCAGGGGCCATGATTGGCCTGGTGTTGATA<br>TTTTCCCTAATGACATGGTGCAGAGTTGGTATCCATCTTTGCA<br>TTAAATTAAAGCACACCAAGAAAAGACAGATTTATACAGACAT<br>AGAGATGAACCGACTTGGAAAGTAA |
| 39 | Envelope; LCMV | ATGGGTCAGATTGTGACAATGTTTGAGGCTCTGCCTCACATCA<br>TCGATGAGGTGATCAACATTGTCATTATTGTGCTTATCGTGAT<br>CACGGGTATCAAGGCTGTCTACAATTTTGCCACCTGTGGGATA<br>TTCGCATTGATCAGTTTCCTACTTCTGGCTGGCAGGTCCTGTG<br>GCATGTACGGTCTTAAGGGACCCGACATTTACAAAGGAGTTTA<br>CCAATTTAAGTCAGTGGAGTTTGATATGTCACATCTGAACCTG<br>ACCATGCCCAACGCATGTTCAGCCAACAACTCCCACCATTACA<br>TCAGTATGGGGACTTCTGGACTAGAATTGACCTTCACCAATGA<br>TTCCATCATCAGTCACAACTTTTGCAATCTGACCTCTGCCTTC<br>AACAAAAAGACCTTTGACCACACACTCATGAGTATAGTTTCGA<br>GCCTACACCTCAGTATCAGAGGGAACTCCAACTATAAGGCAGT<br>ATCCTGCGACTTCAACAATGGCATAACCATCCAATACAACTTG<br>ACATTCTCAGATCGACAAAGTGCTCAGAGCCAGTGTAGAACCT<br>TCAGAGGTAGAGTCCTAGATATGTTTAGAACTGCCTTCGGGGG<br>GAAATACATGAGGAGTGGCTGGGGCTGGACAGGCTCAGATGGC<br>AAGACCACCTGGTGTAGCCAGACGAGTTACCAATACCTGATTA<br>TACAAAATAGAACCTGGGAAAACCACTGCACATATGCAGGTCC<br>TTTTGGGATGTCCAGGATTCTCCTTTCCCAAGAGAAGACTAAG<br>TTCTTCACTAGGAGACTAGCGGGCACATTCACCTGGACTTTGT<br>CAGACTCTTCAGGGGTGGAGAATCCAGGTGGTTATTGCCTGAC<br>CAAATGGATGATTCTTGCTGCAGAGCTTAAGTGTTTCGGGAAC<br>ACAGCAGTTGCGAAATGCAATGTAAATCATGATGCCGAATTCT<br>GTGACATGCTGCGACTAATTGACTACAACAAGGCTGCTTTGAG<br>TAAGTTCAAAGAGGACGTAGAATCTGCCTTGCACTTATTCAAA<br>ACAACAGTGAATTCTTTGATTTCAGATCAACTACTGATGAGGA<br>ACCACTTGAGAGATCTGATGGGGGTGCCATATTGCAATTACTC<br>AAAGTTTTGGTACCTAGAACATGCAAAGACCGGCGAAACTAGT<br>GTCCCCAAGTGCTGGCTTGTCACCAATGGTTCTTACTTAAATG<br>AGACCCACTTCAGTGATCAAATCGAACAGGAAGCCGATAACAT<br>GATTACAGAGATGTTGAGGAAGGATTACATAAAGAGGCAGGGG<br>AGTACCCCCCTAGCATTGATGGACCTTCTGATGTTTTCCACAT<br>CTGCATATCTAGTCAGCATCTTCCTGCACCTTGTCAAAATACC<br>AACACACAGGCACATAAAAGGTGGCTCATGTCCAAAGCCACAC<br>CGATTAACCAACAAAGGAATTTGTAGTTGTGGTGCATTTAAGG<br>TGCCTGGTGTAAAAACCGTCTGGAAAAGACGCTGA |
| 40 | Envelope; FPV | ATGAACACTCAAATCCTGGTTTTCGCCCTTGTGGCAGTCATCC<br>CCACAAATGCAGACAAAATTTGTCTTGGACATCATGCTGTATC<br>AAATGGCACCAAAGTAAACACACTCACTGAGAGAGGAGTAGAA<br>GTTGTCAATGCAACGGAAACAGTGGAGCGGACAAACATCCCCA<br>AAATTTGCTCAAAAGGGAAAAGAACCACTGATCTTGGCCAATG<br>CGGACTGTTAGGGACCATTACCGGACCACCTCAATGCGACCAA<br>TTTCTAGAATTTTCAGCTGATCTAATAATCGAGAGACGAGAAG<br>GAAATGATGTTTGTTACCCGGGGAAGTTTGTTAATGAAGAGGC<br>ATTGCGACAAATCCTCAGAGGATCAGGTGGGATTGACAAAGAA<br>ACAATGGGATTCACATATAGTGGAATAAGGACCAACGGAACAA<br>CTAGTGCATGTAGAAGATCAGGGTCTTCATTCTATGCAGAAAT<br>GGAGTGGCTCCTGTCAAATACAGACAATGCTGCTTTCCCACAA<br>ATGACAAAATCATACAAAAACACAAGGAGAGAATCAGCTCTGA<br>TAGTCTGGGGAATCCACCATTCAGGATCAACCACCGAACAGAC<br>CAAACTATATGGGAGTGGAAATAAACTGATAACAGTCGGGAGT<br>TCCAAATATCATCAATCTTTTGTGCCGAGTCCAGGAACACGAC<br>CGCAGATAAATGGCCAGTCCGGACGGATTGATTTTCATTGGTT<br>GATCTTGGATCCCAATGATACAGTTACTTTTAGTTTCAATGGG<br>GCTTTCATAGCTCCAAATCGTGCCAGCTTCTTGAGGGGAAAGT |

-continued

| SEQ ID NO: | Description | Sequence |
|---|---|---|
| | | CCATGGGGATCCAGAGCGATGTGCAGGTTGATGCCAATTGCGA<br>AGGGGAATGCTACCACAGTGGAGGGACTATAACAAGCAGATTG<br>CCTTTTCAAAACATCAATAGCAGAGCAGTTGGCAAATGCCCAA<br>GATATGTAAAACAGGAAAGTTTATTATTGGCAACTGGGATGAA<br>GAACGTTCCCGAACCTTCCAAAAAAAGGAAAAAAAGAGGCCTG<br>TTTGGCGCTATAGCAGGGTTTATTGAAAATGGTTGGGAAGGTC<br>TGGTCGACGGGTGGTACGGTTTCAGGCATCAGAATGCACAAGG<br>AGAAGGAACTGCAGCAGACTACAAAAGCACCCAATCGGCAATT<br>GATCAGATAACCGGAAAGTTAAATAGACTCATTGAGAAAACCA<br>ACCAGCAATTTGAGCTAATAGATAATGAATTCACTGAGGTGGA<br>AAAGCAGATTGGCAATTTAATTAACTGGACCAAAGACTCCATC<br>ACAGAAGTATGGTCTTACAATGCTGAACTTCTTGTGGCAATGG<br>AAAACCAGCACACTATTGATTTGGCTGATTCAGAGATGAACAA<br>GCTGTATGAGCGAGTGAGGAAACAATTAAGGGAAAATGCTGAA<br>GAGGATGGCACTGGTTGCTTTGAAATTTTTCATAAATGTGACG<br>ATGATTGTATGGCTAGTATAAGGAACAATACTTATGATCACAG<br>CAAATACAGAGAAGAAGCGATGCAAAATAGAATACAAATTGAC<br>CCAGTCAAATTGAGTAGTGGCTACAAAGATGTGATACTTTGGT<br>TTAGCTTCGGGGCATCATGCTTTTTGCTTCTTGCCATTGCAAT<br>GGGCCTTGTTTTCATATGTGTGAAGAACGGAAACATGCGGTGC<br>ACTATTTGTATATAA |
| 41 | Envelope; RRV | AGTGTAACAGAGCACTTTAATGTGTATAAGGCTACTAGACCAT<br>ACCTAGCACATTGCGCCGATTGCGGGGACGGGTACTTCTGCTA<br>TAGCCCAGTTGCTATCGAGGAGATCCGAGATGAGGCGTCTGAT<br>GGCATGCTTAAGATCCAAGTCTCCGCCCAAATAGGTCTGGACA<br>AGGCAGGCACCCACGCCCACACGAAGCTCCGATATATGGCTGG<br>TCATGATGTTCAGGAATCTAAGAGAGATTCCTTGAGGGTGTAC<br>ACGTCCGCAGCGTGCTCCATACATGGGACGATGGGACACTTCA<br>TCGTCGCACACTGTCCACCAGGCGACTACCTCAAGGTTTCGTT<br>CGAGGACGCAGATTCGCACGTGAAGGCATGTAAGGTCCAATAC<br>AAGCACAATCCATTGCCGGTGGGTAGAGAGAAGTTCGTGGTTA<br>GACCACACTTTGGCGTAGAGCTGCCATGCACCTCATACCAGCT<br>GACAACGGCTCCCACCGACGAGGAGATTGACATGCATACACCG<br>CCAGATATACCGGATCGCACCCTGCTATCACAGACGGCGGGCA<br>ACGTCAAAATAACAGCAGGCGGCAGGACTATCAGGTACAACTG<br>TACCTGCGGCCGTGACAACGTAGGCACTACCAGTACTGACAAG<br>ACCATCAACACATGCAAGATTGACCAATGCCATGCTGCCGTCA<br>CCAGCCATGACAAATGGCAATTTACCTCTCCATTTGTTCCCAG<br>GGCTGATCAGACAGCTAGGAAAGGCAAGGTACACGTTCCGTTC<br>CCTCTGACTAACGTCACCTGCCGAGTGCCGTTGGCTCGAGCGC<br>CGGATGCCACCTATGGTAAGAAGGAGGTGACCCTGAGATTACA<br>CCCAGATCATCCGACGCTCTTCTCCTATAGGAGTTTAGGAGCC<br>GAACCGCACCCGTACGAGGAATGGGTTGACAAGTTCTCTGAGC<br>GCATCATCCCAGTGACGGAAGAAGGGATTGAGTACCAGTGGGG<br>CAACAACCCGCCGGTCTGCCTGTGGGCGCAACTGACGACCGAG<br>GGCAAACCCCATGGCTGGCCACATGAAATCATTCAGTACTATT<br>ATGGACTATACCCCGCCGCCACTATTGCCGCAGTATCCGGGGC<br>GAGTCTGATGGCCCTCCTAACTCTGGCGGCCACATGCTGCATG<br>CTGGCCACCGCGAGGAGAAAGTGCCTAACACCGTACGCCCTGA<br>CGCCAGGAGCGGTGGTACCGTTGACACTGGGGCTGCTTTGCTG<br>CGCACCGAGGGCGAATGCA |
| 42 | Envelope; MLV 10A1 | ATGGAAGGTCCAGCGTTCTCAAAACCCCTTAAAGATAAGATTA<br>ACCCGTGGAAGTCCTTAATGGTCATGGGGGTCTATTTAAGAGT<br>AGGGATGGCAGAGAGCCCCCATCAGGTCTTTAATGTAACCTGG<br>AGAGTCACCAACCTGATGACTGGGCGTACCGCCAATGCCACCT<br>CCCTTTTAGGAACTGTACAAGATGCCTTCCCAAGATTATATTT<br>TGATCTATGTGATCTGGTCGGAGAAGAGTGGGACCCTTCAGAC<br>CAGGAACCATATGTCGGGTATGGCTGCAAATACCCCGGAGGGA<br>GAAAGCGGACCCGGACTTTTGACTTTTACGTGTGCCCTGGGCA<br>TACCGTAAAATCGGGGTGTGGGGGGCCAAGAGAGGGCTACTGT<br>GGTGAATGGGGTTGTGAAACCACCGGACAGGCTTACTGGAAGC<br>CCACATCATCATGGGACCTAATCTCCCTTAAGCGCGGTAACAC<br>CCCCTGGGACACGGGATGCTCCAAAATGGCTTGTGGCCCCTGC<br>TACGACCTCTCCAAAGTATCCAATTCCTTCCAAGGGGCTACTC<br>GAGGGGGCAGATGCAACCCTCTAGTCCTAGAATTCACTGATGC<br>AGGAAAAAAGGCTAATTGGGACGGGCCCAAATCGTGGGGACTG<br>AGACTGTACCGGACAGGAACAGATCCTATTACCATGTTCTCCC<br>TGACCCGCCAGGTCCTCAATATAGGGCCCCGCATCCCCATTGG<br>GCCTAATCCCGTGATCACTGGTCAACTACCCCCCTCCCGACCC<br>GTGCAGATCAGGCTCCCCAGGCCTCCTCAGCCTCCTCCTACAG<br>GCGCAGCCTCTATAGTCCCTGAGACTGCCCCACCTTCTCAACA<br>ACCTGGGACGGGAGACAGGCTGCTAAACCTGGTAGAAGGAGCC<br>TATCAGGCGCTTAACCTCACCAATCCCGACAAGACCCAAGAAT<br>GTTGGCTGTGCTTAGTGTCGGGACCTCCTTATTACGAAGGAGT |

-continued

| SEQ ID NO: | Description | Sequence |
|---|---|---|
| | | AGCGGTCGTGGGCACTTATACCAATCATTCTACCGCCCCGGCC<br>AGCTGTACGGCCACTTCCCAACATAAGCTTACCCTATCTGAAG<br>TGACAGGACAGGGCCTATGCATGGGAGCACTACCTAAAACTCA<br>CCAGGCCTTATGTAACACCACCCAAAGTGCCGGCTCAGGATCC<br>TACTACCTTGCAGCACCCGCTGGAACAATGTGGGCTTGTAGCA<br>CTGGATTGACTCCCTGCTTGTCCACCACGATGCTCAATCTAAC<br>CACAGACTATTGTGTATTAGTTGAGCTCTGGCCCAGAATAATT<br>TACCACTCCCCCGATTATATGTATGGTCAGCTTGAACAGCGTA<br>CCAAATATAAGAGGGAGCCAGTATCGTTGACCCTGGCCCTTCT<br>GCTAGGAGGATTAACCATGGGAGGGATTGCAGCTGGAATAGGG<br>ACGGGGACCACTGCCCTAATCAAAACCCAGCAGTTTGAGCAGC<br>TTCACGCCGCTATCCAGACAGACCTCAACGAAGTCGAAAAATC<br>AATTACCAACCTAGAAAAGTCACTGACCTCGTTGTCTGAAGTA<br>GTCCTACAGAACCGAAGAGGCCTAGATTTGCTCTTCCTAAAAG<br>AGGGAGGTCTCTGCGCAGCCCTAAAAGAAGAATGTTGTTTTTA<br>TGCAGACCACACGGGACTAGTGAGAGACAGCATGGCCAAACTA<br>AGGGAAAGGCTTAATCAGAGACAAAAACTATTTGAGTCAGGCC<br>AAGGTTGGTTCGAAGGGCAGTTTAATAGATCCCCCTGGTTTAC<br>CACCTTAATCTCCACCATCATGGGACCTCTAATAGTACTCTTA<br>CTGATCTTACTCTTTGGACCCTGCATTCTCAATCGATTGGTCC<br>AATTTGTTAAAGACAGGATCTCAGTGGTCCAGGCTCTGGTTTT<br>GACTCAACAATATCACCAGCTAAAACCTATAGAGTACGAGCCA<br>TGA |
| 43 | Envelope; Ebola | ATGGGTGTTACAGGAATATTGCAGTTACCTCGTGATCGATTCA<br>AGAGGACATCATTCTTTCTTTGGGTAATTATCCTTTTCCAAAG<br>AACATTTTCCATCCCACTTGGAGTCATCCACAATAGCACATTA<br>CAGGTTAGTGATGTCGACAAACTGGTTTGCCGTGACAAACTGT<br>CATCCACAAATCAATTGAGATCAGTTGGACTGAATCTCGAAGG<br>GAATGGAGTGGCAACTGACGTGCCATCTGCAACTAAAAGATGG<br>GGCTTCAGGTCCGGTGTCCCACCAAAGGTGGTCAATTATGAAG<br>CTGGTGAATGGGCTGAAAACTGCTACAATCTTGAAATCAAAAA<br>ACCTGACGGGAGTGAGTGTCTACCAGCAGCGCCAGACGGGATT<br>CGGGGCTTCCCCCGGTGCCGGTATGTGCACAAAGTATCAGGAA<br>CGGGACCGTGTGCCGGAGACTTTGCCTTCCACAAAGAGGGTGC<br>TTTCTTCCTGTATGACCGACTTGCTTCCACAGTTATCTACCGA<br>GGAACGACTTTCGCTGAAGGTGTCGTTGCATTTCTGATACTGC<br>CCCAAGCTAAGAAGGACTTCTTCAGCTCACACCCCTTGAGAGA<br>GCCGGTCAATGCAACGGAGGACCCGTCTAGTGGCTACTATTCT<br>ACCACAATTAGATATCAAGCTACCGGTTTTGGAACCAATGAGA<br>CAGAGTATTTGTTCGAGGTTGACAATTTGACCTACGTCCAACT<br>TGAATCAAGATTCACACCACAGTTTCTGCTCCAGCTGAATGAG<br>ACAATATATACAAGTGGGAAAAGGAGCAATACCACGGGAAAAC<br>TAATTTGGAAGGTCAACCCCGAAATTGATACAACAATCGGGGA<br>GTGGGCCTTCTGGGAAACTAAAAAAACCTCACTAGAAAAATTC<br>GCAGTGAAGAGTTGTCTTTCACAGCTGTATCAAACAGAGCCAA<br>AAACATCAGTGGTCAGAGTCCGGCGCGAACTTCTTCCGACCCA<br>GGGACCAACACAACAACTGAAGACCACAAAATCATGGCTTCAG<br>AAAATTCCTCTGCAATGGTTCAAGTGCACAGTCAAGGAAGGGA<br>AGCTGCAGTGTCGCATCTGACAACCCTTGCCACAATCTCCACG<br>AGTCCTCAACCCCCCACAACCAAACCAGGTCCGGACAACAGCA<br>CCCACAATACACCCGTGTATAAACTTGACATCTCTGAGGCAAC<br>TCAAGTTGAACAACATCACCGCAGAACAGACAACGACAGCACA<br>GCCTCCGACACTCCCCCCGCCACGACCGCAGCCGGACCCCTAA<br>AAGCAGAGAACACCAACACGAGCAAGGGTACCGACCTCCTGGA<br>CCCCGCCACCACAACAAGTCCCCAAAACCACAGCGAGACCGCT<br>GGCAACAACAACACTCATCACCAAGATACCGGAGAAGAGAGTG<br>CCAGCAGCGGGAAGCTAGGCTTAATTACCAATACTATTGCTGG<br>AGTCGCAGGACTGATCACAGGCGGGAGGAGAGCTCGAAGAGAA<br>GCAATTGTCAATGCTCAACCCAAATGCAACCCTAATTTACATT<br>ACTGGACTACTCAGGATGAAGGTGCTGCAATCGGACTGGCCTG<br>GATACCATATTTCGGGCCAGCAGCCGAGGGAATTTACATAGAG<br>GGGCTGATGCACAATCAAGATGGTTTAATCTGTGGGTTGAGAC<br>AGCTGGCCAACGAGACGACTCAAGCTCTTCAACTGTTCCTGAG<br>AGCCACAACCGAGCTACGCACCTTTTCAATCCTCAACCGTAAG<br>GCAATTGATTTCTTGCTGCAGCGATGGGGCGGCACATGCCACA<br>TTTTGGGACCGGACTGCTGTATCGAACCACATGATTGGACCAA<br>GAACATAACAGACAAAATTGATCAGATTATTCATGATTTTGTT<br>GATAAAACCCTTCCGGACCAGGGGGACAATGACAATTGGTGGA<br>CAGGATGGAGACAATGGATACCGGCAGGTATTGGAGTTACAGG<br>CGTTATAATTGCAGTTATCGCTTTATTCTGTATATGCAAATTT<br>GTCTTTTAG |

-continued

| SEQ ID NO: | Description | Sequence |
|---|---|---|
| 44 | Forward Primer to amplify Gag, Pol, and Integrase | TAAGCAGAATTCATGAATTTGCCAGGAAGAT |
| 45 | Reverse Primer to amplify Gag, Pol, and Integrase | CCATACAATGAATGGACACTAGGCGGCCGCACGAAT |
| 46 | KTF11 Forward Primer | CCGTTCTGGAGCTGTTGATAA |
| 47 | KIF11 Reverse Primer | TGTTCTTTCTACAAGGGCAGTAA |
| 48 | KIFU TaqMan Probe (Fam/Iowa Black Zen quencher) | CCCTGTTGACTTTGGGAAGGGTCA |
| 49 | Actin forward primer | GGACCTGACTGACTACCTCAT |
| 50 | Actin reverse primer #1 | CGTAGCACAGCTTCTCCTTAAT |
| 51 | Actin reverse primer #2 | ATTAAGGAGAAGCTGTGCTACG |
| 52 | Actin probe (FAM or VIC/lowa Black Zen) | AGCGGGAAATCGTGCGTGAC |
| 53 | Gag forward primer | GGAGCTAGAACGATTCGCAGTTA |
| 54 | Gag reverse primer | TGTAGCTGTCCCAGTATTTGTC |
| 55 | Gag probe (FAM/Iowa Black Zen) | CCTGGCCTGTTAGAAACATCAGAAGGCTGT |
| 56 | Non-targeting shRNA sequence | GCCGCTTTGTAGGATAGAGCTCGAGCTCTATCCTACAAAGCGG CTTTTT |

What is claimed is:

1. A modified mesenchymal stem cell comprising a mesenchymal stem cell infected with a lentiviral particle, wherein the lentiviral particle comprises:
   an envelope protein capable of infecting the mesenchymal stem cell; and
   a first nucleotide sequence encoding a small RNA capable of binding a non-coding region of a host copy of KIF11, wherein the first nucleotide sequence encoding a small RNA is present in the modified mesenchymal stem cell at between about 1 and about 10 copies per cell.

2. The modified mesenchymal stem cell of claim 1, wherein the non-coding region of the host copy of KIF11 is a 3' untranslated region or a 5' untranslated region.

3. A method of producing a modified mesenchymal stem cell, the method comprising: infecting a mesenchymal stem cell with an effective amount of a lentiviral particle, wherein the lentiviral particle comprises:
   an envelope protein capable of infecting the mesenchymal stem cell; and
   a first nucleotide sequence encoding a small RNA capable of binding a non-coding region of a host copy of KIF11, wherein the first nucleotide sequence is present in the modified mesenchymal stem cell at between about 1 and about 10 copies per cell.

4. The method of claim 3, wherein the non-coding region of the host copy of KIF11 is a 3' untranslated region or a 5' untranslated region.

5. A method of treating cancer in a subject, the method comprising administering a therapeutically-effective amount of the modified mesenchymal stem cell of claim 1 to the subject.

6. The method of claim 5, wherein the modified mesenchymal stem cell is allogeneic to the subject.

7. The method of claim 5, wherein the modified mesenchymal stem cell is autologous to the subject.

8. The method of claim 5, wherein the cancer is selected from any one or more of a carcinoma, a sarcoma, a myeloma, a lymphoma, a mixed type, or a mixture of the foregoing.

9. A lentiviral particle produced by a packaging cell and capable of infecting a target cell, the lentiviral particle comprising:
   an envelope protein capable of infecting the target cell; and
   a first nucleotide sequence encoding a small RNA capable of binding a non-coding region of a host copy of KIF11, wherein the non-coding region of the host copy of KIF11 is a 3' untranslated region or a 5' untranslated region,
   wherein the lentiviral particle further comprises a second nucleotide sequence encoding a KIF11 gene or a variant thereof, wherein the KIF11 gene or the variant thereof lacks at least one sequence portion,
   wherein the sequence portion is in a non-coding region of the KIF11 gene, and wherein the non-coding region of the KIF11 gene is in at least one of a 5' untranslated region or a 3' untranslated region, and wherein the target cell is a mesenchymal stem cell.

10. A method of treating cancer in a subject, the method comprising administering a therapeutically effective amount of the lentiviral particle of claim 9 to the subject.

11. The method of claim 10, wherein the cancer is selected from any one or more of a carcinoma, a sarcoma, a myeloma, a lymphoma, a mixed type, or a mixture of the foregoing.

12. The method of claim 10, wherein the lentiviral particle is administered to the subject via an infected target cell.

13. The method of claim 12, wherein the target cell comprises a somatic cell.

14. The method of claim 13, wherein the somatic cell comprises a hepatocyte or a lymphocyte.

15. The method of claim 14, wherein the somatic cell comprises a lymphocyte, wherein the lymphocyte comprises a tumor specific T cell.

16. The method of claim 12, wherein the target cell comprises a stem cell.

17. The method of claim 16, wherein the stem cell comprises an induced pluripotent stem cell or a mesenchymal stem cell.

* * * * *

SEQUENCE LISTING

```
<160> NUMBER OF SEQ ID NOS: 56

<210> SEQ ID NO 1
<211> LENGTH: 53
<212> TYPE: DNA
<213> ORGANISM: Artificial Sequence
<220> FEATURE:
<223> OTHER INFORMATION: KIF11 small RNA sequence #1

<400> SEQUENCE: 1

tttgatctgg caaccatatt tctcgagaaa tatggttgcc agatcaaatt ttt            53


<210> SEQ ID NO 2
<211> LENGTH: 53
<212> TYPE: DNA
<213> ORGANISM: Artificial Sequence
<220> FEATURE:
<223> OTHER INFORMATION: KIF11 small RNA sequence #2

<400> SEQUENCE: 2

tgcaatgtaa atacgtattt cctcgaggaa atacgtattt acattgcatt ttt            53
```

-continued

<210> SEQ ID NO 3
<211> LENGTH: 51
<212> TYPE: DNA
<213> ORGANISM: Artificial Sequence
<220> FEATURE:
<223> OTHER INFORMATION: KIF11 small RNA sequence #3

<400> SEQUENCE: 3
gcttgagctt acataggtaa ctcgagttac ctatgtaagc tcaagctttt t 51

<210> SEQ ID NO 4
<211> LENGTH: 3171
<212> TYPE: DNA
<213> ORGANISM: Artificial Sequence
<220> FEATURE:
<223> OTHER INFORMATION: KIF11 sequence

<400> SEQUENCE: 4
atggcgtcgc agccaaattc gtctgcgaag aagaaagagg agaaggggaa gaacatccag 60
gtggtggtga gatgcagacc atttaatttg gcagagcgga aagctagcgc ccattcaata 120
gtagaatgtg atcctgtacg aaaagaagtt agtgtacgaa ctggaggatt ggctgacaag 180
agctcaagga aaacatacac ttttgatatg gtgtttggag catctactaa acagattgat 240
gtttaccgaa gtgttgtttg tccaattctg gatgaagtta ttatgggcta taattgcact 300
atctttgcgt atggccaaac tggcactgga aaaactttta caatggaagg tgaaaggtca 360
cctaatgaag agtatacctg ggaagaggat cccttggctg gtataattcc acgtaccctt 420
catcaaattt ttgagaaact tactgataat ggtactgaat tttcagtcaa agtgtctctg 480
ttggagatct ataatgaaga gctttttgat cttcttaatc catcatctga tgtttctgag 540
agactacaga tgtttgatga tccccgtaac aagagaggag tgataattaa aggtttagaa 600
gaaattacag tacacaacaa ggatgaagtc tatcaaattt tagaaaaggg ggcagcaaaa 660
aggacaactg cagctactct gatgaatgca tactctagtc gttcccactc agttttctct 720
gttacaatac atatgaaaga aactacgatt gatggagaag agcttgttaa aatcggaaag 780
ttgaacttgg ttgatcttgc aggaagtgaa aacattggcc gttctggagc tgttgataag 840
agagctcggg aagctggaaa tataaatcaa tccctgttga ctttgggaag ggtcattact 900
gcccttgtag aaagaacacc tcatgttcct tatcgagaat ctaaactaac tagaatcctc 960
caggattctc ttggagggcg tacaagaaca tctataattg caacaatttc tcctgcatct 1020
ctcaatcttg aggaaactct gagtacattg gaatatgctc atagagcaaa gaacatattg 1080
aataagcctg aagtgaatca gaaactcacc aaaaaagctc ttattaagga gtatacggag 1140
gagatagaac gtttaaaacg agatcttgct gcagcccgtg agaaaaatgg agtgtatatt 1200
tctgaagaaa attttagagt catgagtgga aaattaactg ttcaagaaga gcagattgta 1260
gaattgattg aaaaaattgg tgctgttgag gaggagctga atagggttac agagttgttt 1320
atggataata aaaatgaact tgaccagtgt aaatctgacc tgcaaaataa aacacaagaa 1380
cttgaaacca ctcaaaaaca tttgcaagaa actaaattac aacttgttaa agaagaatat 1440
atcacatcag ctttggaaag tactgaggag aaacttcatg atgctgccag caagctgctt 1500
aacacagttg aagaaactac aaaagatgta tctggtctcc attccaaact ggatcgtaag 1560
aaggcagttg accaacacaa tgcagaagct caggatattt ttggcaaaaa cctgaatagt 1620
ctgtttaata atatggaaga attaattaag gatggcagct caaagcaaaa ggccatgcta 1680
gaagtacata agaccttatt tggtaatctg ctgtcttcca gtgtctctgc attagatacc 1740

-continued

```
attactacag tagcacttgg atctctcaca tctattccag aaaatgtgtc tactcatgtt   1800
tctcagattt ttaatatgat actaaaagaa caatcattag cagcagaaag taaaactgta   1860
ctacaggaat tgattaatgt actcaagact gatcttctaa gttcactgga aatgatttta   1920
tccccaactg tggtgtctat actgaaaatc aatagtcaac taaagcatat tttcaagact   1980
tcattgacag tggccgataa gatagaagat caaaaaaagg aactagatgg ctttctcagt   2040
atactgtgta acaatctaca tgaactacaa gaaaatacca tttgttcctt ggttgagtca   2100
caaaagcaat gtggaaacct aactgaagac ctgaagacaa taaagcagac ccattcccag   2160
gaactttgca agttaatgaa tctttggaca gagagattct gtgctttgga ggaaaagtgt   2220
gaaaatatac agaaaccact tagtagtgtc caggaaaata tacagcagaa atctaaggat   2280
atagtcaaca aaatgacttt tcacagtcaa aaattttgtg ctgattctga tggcttctca   2340
caggaactca gaaattttaa ccaagaaggt acaaaattgg ttgaagaatc tgtgaaacac   2400
tctgataaac tcaatggcaa cctggaaaaa atatctcaag agactgaaca gagatgtgaa   2460
tctctgaaca caagaacagt ttatttttct gaacagtggg tatcttcctt aaatgaaagg   2520
gaacaggaac ttcacaactt attggaggtt gtaagccaat gttgtgaggc ttcaagttca   2580
gacatcactg agaaatcaga tggacgtaag gcagctcatg agaaacagca taacattttt   2640
cttgatcaga tgactattga tgaagataaa ttgatagcac aaaatctaga acttaatgaa   2700
accataaaaa ttggtttgac taagcttaat tgctttctgg aacaggatct gaaactggat   2760
atcccaacag gtacgacacc acagaggaaa agttatttat acccatcaac actggtaaga   2820
actgaaccac gtgaacatct ccttgatcag ctgaaaagga aacagcctga gctgttaatg   2880
atgctaaact gttcagaaaa caacaaagaa gagacaattc cggatgtgga tgtagaagag   2940
gcagttctgg ggcagtatac tgaagaacct ctaagtcaag agccatctgt agatgctggt   3000
gtggattgtt catcaattgg cggggttcca tttttccagc ataaaaaatc acatggaaaa   3060
gacaaagaaa acagaggcat taacacactg gagaggtcta aagtggaaga aactacagag   3120
cacttggtta caaagagcag attacctctg cgagcccaga tcaaccttta a            3171
```

<210> SEQ ID NO 5
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 5

```
gtagtcttat gcaatactct tgtagtcttg caacatggta acgatgagtt agcaacatgc     60
cttacaagga gagaaaaagc accgtgcatg ccgattggtg gaagtaaggt ggtacgatcg    120
tgccttatta ggaaggcaac agacgggtct gacatggatt ggacgaacca ctgaattgcc    180
gcattgcaga gatattgtat ttaagtgcct agctcgatac aataaacg                 228
```

<210> SEQ ID NO 6
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 6

```
ggtctctctg gttagaccag atctgagcct gggagctctc tggctaacta gggaacccac     60
tgcttaagcc tcaataaagc ttgccttgag tgcttcaagt agtgtgtgcc cgtctgttgt    120
```

gtgactctgg taactagaga tccctcagac ccttttagtc agtgtggaaa atctctagca 180

<210> SEQ ID NO 7
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 7
tacgccaaaa attttgacta gcggaggcta gaaggagaga g 41

<210> SEQ ID NO 8
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 8
aggagctttg ttccttgggt tcttgggagc agcaggaagc actatgggcg cagcctcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcc 233

<210> SEQ ID NO 9
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 9
ttttaaaaga aaagggggga ttggggggta cagtgcaggg gaaagaatag tagacataat 60
agcaacagac atacaaacta aagaattaca aaaacaaatt acaaaattca aaatttta 118

<210> SEQ ID NO 10
<211> LENGTH: 217
<212> TYPE: DNA
<213> ORGANISM: Artificial Sequence
<220> FEATURE:
<223> OTHER INFORMATION: Polymerase III shRNA promoters - H1 promoter

<400> SEQUENCE: 10
gaacgctgac gtcatcaacc cgctccaagg aatcgcgggc ccagtgtcac taggcgggaa 60
cacccagcgc gcgtgcgccc tggcaggaag atggctgtga gggacagggg agtggcgccc 120
tgcaatattt gcatgtcgct atgtgttctg ggaaatcacc ataaacgtga aatgtctttg 180
gatttgggaa tcttataagt tctgtatgag accactt 217

<210> SEQ ID NO 11
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 11
aatcaacctc tgattacaaa atttgtgaaa gattgactgg tattcttaac tatgttgctc 60
cttttacgct atgtggatac gctgctttaa tgcctttgta tcatgctatt gcttcccgta 120

-continued

```
tggctttcat tttctcctcc ttgtataaat cctggttgct gtctctttat gaggagttgt    180

ggcccgttgt caggcaacgt ggcgtggtgt gcactgtgtt tgctgacgca acccccactg    240

gttggggcat tgccaccacc tgtcagctcc tttccgggac tttcgctttc cccctcccta    300

ttgccacggc ggaactcatc gccgcctgcc ttgcccgctg ctggacaggg gctcggctgt    360

tgggcactga caattccgtg gtgttgtcgg ggaaatcatc gtcctttcct tggctgctcg    420

cctgtgttgc cacctggatt ctgcgcggga cgtccttctg ctacgtccct tcggccctca    480

atccagcgga ccttccttcc cgcggcctgc tgccggctct gcggcctctt ccgcgtcttc    540

gccttcgccc tcagacgagt cggatctccc tttgggccgc ctccccgcct                590
```

<210> SEQ ID NO 12
<211> LENGTH: 250
<212> TYPE: DNA
<213> ORGANISM: Artificial Sequence
<220> FEATURE:
<223> OTHER INFORMATION: 3' delta LTR

<400> SEQUENCE: 12

```
tggaagggct aattcactcc caacgaagat aagatctgct tttgcttgt actgggtctc      60

tctggttaga ccagatctga gcctgggagc tctctggcta actagggaac ccactgctta    120

agcctcaata aagcttgcct tgagtgcttc aagtagtgtg tgcccgtctg ttgtgtgact    180

ctggtaacta gagatccctc agaccctttt agtcagtgtg gaaaatctct agcagtagta    240

gttcatgtca                                                           250
```

<210> SEQ ID NO 13
<211> LENGTH: 290
<212> TYPE: DNA
<213> ORGANISM: Artificial Sequence
<220> FEATURE:
<223> OTHER INFORMATION: Helper/Rev - Chicken beta actin (CAG)
promoter - Transcription

<400> SEQUENCE: 13

```
gctattacca tgggtcgagg tgagccccac gttctgcttc actctcccca tctccccccc     60

ctccccaccc ccaattttgt atttatttat tttttaatta ttttgtgcag cgatgggggc    120

gggggggggg ggggcgcgcg ccaggcgggg cggggcgggg cgaggggcgg ggcggggcga    180

ggcggagagg tgcggcggca gccaatcaga gcggcgcgct ccgaaagttt ccttttatgg    240

cgaggcggcg gcggcggcgg ccctataaaa agcgaagcgc gcggcgggcg               290
```

<210> SEQ ID NO 14
<211> LENGTH: 1503
<212> TYPE: DNA
<213> ORGANISM: Artificial Sequence
<220> FEATURE:
<223> OTHER INFORMATION: Helper/Rev - HIV Gag - Viral capsid

<400> SEQUENCE: 14

```
atgggtgcga gagcgtcagt attaagcggg ggagaattag atcgatggga aaaaattcgg     60

ttaaggccag ggggaaagaa aaaatataaa ttaaaacata tagtatgggc aagcagggag    120

ctagaacgat tcgcagttaa tcctggcctg ttagaaacat cagaaggctg tagacaaata    180

ctgggacagc tacaaccatc ccttcagaca ggatcagaag aacttagatc attatataat    240

acagtagcaa ccctctattg tgtgcatcaa aggatagaga taaaagacac caaggaagct    300

ttagacaaga tagaggaaga gcaaaacaaa agtaagaaaa aagcacagca agcagcagct    360
```

-continued

```
gacacaggac acagcaatca ggtcagccaa aattacccta tagtgcagaa catccagggg    420

caaatggtac atcaggccat atcacctaga actttaaatg catgggtaaa agtagtagaa    480

gagaaggctt tcagcccaga agtgataccc atgttttcag cattatcaga aggagccacc    540

ccacaagatt taaacaccat gctaaacaca gtgggggac atcaagcagc catgcaaatg    600

ttaaaagaga ccatcaatga ggaagctgca gaatgggata gagtgcatcc agtgcatgca    660

gggcctattg caccaggcca gatgagagaa ccaaggggaa gtgacatagc aggaactact    720

agtacccttc aggaacaaat aggatggatg acacataatc cacctatccc agtaggagaa    780

atctataaaa gatggataat cctgggatta aataaaatag taagaatgta tagccctacc    840

agcattctgg acataagaca aggaccaaag gaacccttta gagactatgt agaccgattc    900

tataaaactc taagagccga gcaagcttca caagaggtaa aaaattggat gacagaaacc    960

ttgttggtcc aaaatgcgaa cccagattgt aagactattt taaaagcatt gggaccagga   1020

gcgacactag aagaaatgat gacagcatgt cagggagtgg ggggacccgg ccataaagca   1080

agagttttgg ctgaagcaat gagccaagta acaaatccag ctaccataat gatacagaaa   1140

ggcaatttta ggaaccaaag aaagactgtt aagtgtttca attgtggcaa agaagggcac   1200

atagccaaaa attgcagggc ccctaggaaa aagggctgtt ggaaatgtgg aaaggaagga   1260

caccaaatga aagattgtac tgagagacag gctaattttt tagggaagat ctggccttcc   1320

cacaagggaa ggccagggaa ttttcttcag agcagaccag agccaacagc cccaccagaa   1380

gagagcttca ggtttgggga agagacaaca actccctctc agaagcagga gccgatagac   1440

aaggaactgt atcctttagc ttccctcaga tcactctttg gcagcgaccc ctcgtcacaa   1500

taa                                                                 1503
```

<210> SEQ ID NO 15
<211> LENGTH: 1872
<212> TYPE: DNA
<213> ORGANISM: Artificial Sequence
<220> FEATURE:
<223> OTHER INFORMATION: Helper/Rev - HIV Pol - Protease and reverse transcriptase

<400> SEQUENCE: 15

```
atgaatttgc caggaagatg gaaaccaaaa atgatagggg gaattggagg ttttatcaaa     60

gtaggacagt atgatcagat actcatagaa atctgcggac ataaagctat aggtacagta    120

ttagtaggac ctacacctgt caacataatt ggaagaaatc tgttgactca gattggctgc    180

actttaaatt ttcccattag tcctattgag actgtaccag taaaattaaa gccaggaatg    240

gatggcccaa aagttaaaca atggccattg acagaagaaa aaataaaagc attagtagaa    300

atttgtacag aaatggaaaa ggaaggaaaa atttcaaaaa ttgggcctga aaatccatac    360

aatactccag tatttgccat aaagaaaaaa gacagtacta aatggagaaa attagtagat    420

ttcagagaac ttaataagag aactcaagat ttctgggaag ttcaattagg aataccacat    480

cctgcagggt taaaacagaa aaaatcagta acagtactgg atgtgggcga tgcatatttt    540

tcagttccct tagataaaga cttcaggaag tatactgcat ttaccatacc tagtataaac    600

aatgagacac cagggattag atatcagtac aatgtgcttc cacagggatg gaaaggatca    660

ccagcaatat tccagtgtag catgacaaaa atcttagagc cttttagaaa acaaaatcca    720

gacatagtca tctatcaata catggatgat ttgtatgtag gatctgactt agaaataggg    780

cagcatagaa caaaaataga ggaactgaga caacatctgt tgaggtgggg atttaccaca    840
```

-continued

```
ccagacaaaa aacatcagaa agaacctcca ttcctttgga tgggttatga actccatcct    900
gataaatgga cagtacagcc tatagtgctg ccagaaaagg acagctggac tgtcaatgac    960
atacagaaat tagtgggaaa attgaattgg gcaagtcaga tttatgcagg gattaaagta   1020
aggcaattat gtaaacttct taggggaacc aaagcactaa cagaagtagt accactaaca   1080
gaagaagcag agctagaact ggcagaaaac agggagattc taaaagaacc ggtacatgga   1140
gtgtattatg acccatcaaa agacttaata gcagaaatac agaagcaggg gcaaggccaa   1200
tggacatatc aaatttatca agagccattt aaaaatctga aaacaggaaa atatgcaaga   1260
atgaagggtg cccacactaa tgatgtgaaa caattaacag aggcagtaca aaaaatagcc   1320
acagaaagca tagtaatatg gggaaagact cctaaattta aattacccat acaaaaggaa   1380
acatgggaag catggtggac agagtattgg caagccacct ggattcctga gtgggagttt   1440
gtcaataccc ctcccttagt gaagttatgg taccagttag agaaagaacc cataatagga   1500
gcagaaactt tctatgtaga tggggcagcc aatagggaaa ctaaattagg aaaagcagga   1560
tatgtaactg acagaggaag acaaaaagtt gtcccccctaa cggacacaac aaatcagaag   1620
actgagttac aagcaattca tctagctttg caggattcgg gattagaagt aaacatagtg   1680
acagactcac aatatgcatt gggaatcatt caagcacaac cagataagag tgaatcagag   1740
ttagtcagtc aaataataga gcagttaata aaaaaggaaa aagtctacct ggcatgggta   1800
ccagcacaca aaggaattgg aggaaatgaa caagtagatg ggttggtcag tgctggaatc   1860
aggaaagtac ta                                                       1872
```

<210> SEQ ID NO 16
<211> LENGTH: 867
<212> TYPE: DNA
<213> ORGANISM: Artificial Sequence
<220> FEATURE:
<223> OTHER INFORMATION: Helper Rev - HIV Integrase - Integration of viral RNA

<400> SEQUENCE: 16

```
tttttagatg gaatagataa ggcccaagaa gaacatgaga aatatcacag taattggaga     60
gcaatggcta gtgattttaa cctaccacct gtagtagcaa aagaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
agtggatata tagaagcaga agtaattcca gcagagacag ggcaagaaac agcatacttc    300
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaaagaaa    480
attataggac aggtaagaga tcaggctgaa catcttaaga cagcagtaca aatggcagta    540
ttcatccaca attttaaaag aaaagggggg attggggggt acagtgcagg ggaaagaata    600
gtagacataa tagcaacaga catacaaact aaagaattac aaaaacaaat tacaaaaatt    660
caaaattttc gggtttatta cagggacagc agagatccag tttggaaagg accagcaaag    720
ctcctctgga aaggtgaagg ggcagtagta atacaagata atagtgacat aaaagtagtg    780
ccaagaagaa aagcaaagat catcagggat tatggaaaac agatggcagg tgatgattgt    840
gtggcaagta gacaggatga ggattaa                                        867
```

<210> SEQ ID NO 17

-continued

<211> LENGTH: 234
<212> TYPE: DNA
<213> ORGANISM: Artificial Sequence
<220> FEATURE:
<223> OTHER INFORMATION: Helper/Rev - HIV RRE - Binds Rev element

<400> SEQUENCE: 17
aggagctttg ttccttgggt tcttgggagc agcaggaagc actatgggcg cagcgtcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcct 234

<210> SEQ ID NO 18
<211> LENGTH: 351
<212> TYPE: DNA
<213> ORGANISM: Artificial Sequence
<220> FEATURE:
<223> OTHER INFORMATION: Helper/Rev - HIV Rev - Nuclear export and stabilize viral mRNA

<400> SEQUENCE: 18
atggcaggaa gaagcggaga cagcgacgaa gaactcctca aggcagtcag actcatcaag 60
tttctctatc aaagcaaccc acctcccaat cccgagggga cccgacaggc ccgaaggaat 120
agaagaagaa ggtggagaga gagacagaga cagatccatt cgattagtga acggatcctt 180
agcacttatc tgggacgatc tgcggagcct gtgcctcttc agctaccacc gcttgagaga 240
cttactcttg attgtaacga ggattgtgga acttctggga cgcagggggt gggaagccct 300
caaatattgg tggaatctcc tacaatattg gagtcaggag ctaaagaata g 351

<210> SEQ ID NO 19
<211> LENGTH: 352
<212> TYPE: DNA
<213> ORGANISM: Artificial Sequence
<220> FEATURE:
<223> OTHER INFORMATION: Helper/Rev - CMV early (CAG) enhancer - EnhanceTranscription

<400> SEQUENCE: 19
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggac tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tc 352

<210> SEQ ID NO 20
<211> LENGTH: 960
<212> TYPE: DNA
<213> ORGANISM: Artificial Sequence
<220> FEATURE:
<223> OTHER INFORMATION: Helper/Rev - Chicken beta actin intron - Enhance gene expression

<400> SEQUENCE: 20
ggagtcgctg cgttgccttc gccccgtgcc ccgctccgcg ccgcctcgcg ccgcccgccc 60
cggctctgac tgaccgcgtt actcccacag gtgagcgggc gggacggccc ttctcctccg 120
ggctgtaatt agcgcttggt ttaatgacgg ctcgtttctt ttctgtggct gcgtgaaagc 180

-continued

```
cttaaagggc tccgggaggg ccctttgtgc ggggggggagc ggctcggggg gtgcgtgcgt    240

gtgtgtgtgc gtggggagcg ccgcgtgcgg cccgcgctgc ccggcggctg tgagcgctgc    300

gggcgcggcg cggggctttg tgcgctccgc gtgtgcgcga ggggagcgcg gccgggggcg    360

gtgccccgcg gtgcgggggg gctgcgaggg gaacaaaggc tgcgtgcggg gtgtgtgcgt    420

ggggggggtga gcagggggtg tgggcgcggc ggtcgggctg taaccccccc ctgcaccccc    480

ctccccgagt tgctgagcac ggcccggctt cgggtgcggg gctccgtgcg gggcgtggcg    540

cggggctcgc cgtgccgggc ggggggtggc ggcaggtggg ggtgccgggc ggggcggggc    600

cgcctcgggc cggggagggc tcgggggagg ggcgcggcgg ccccggagcg ccggcggctg    660

tcgaggcgcg gcgagccgca gccattgcct tttatggtaa tcgtgcgaga gggcgcaggg    720

acttcctttg tcccaaatct ggcggagccg aaatctggga ggcgccgccg caccccctct    780

agcgggcgcg ggcgaagcgg tgcggcgccg gcaggaagga aatgggcggg gagggccttc    840

gtgcgtcgcc gcgccgccgt ccccttctcc atctccagcc tcggggctgc cgcaggggga    900

cggctgcctt cggggggggac ggggcagggc ggggttcggc ttctggcgtg tgaccggcgg    960
```

<210> SEQ ID NO 21
<211> LENGTH: 448
<212> TYPE: DNA
<213> ORGANISM: Artificial Sequence
<220> FEATURE:
<223> OTHER INFORMATION: Helper/Rev - Rabbit beta globin poly A - RNA stability

<400> SEQUENCE: 21

```
agatcttttt ccctctgcca aaaattatgg ggacatcatg aagccccttg agcatctgac     60

ttctggctaa taaaggaaat ttattttcat tgcaatagtg tgttggaatt ttttgtgtct    120

ctcactcgga aggacatatg ggagggcaaa tcatttaaaa catcagaatg agtatttggt    180

ttagagtttg gcaacatatg ccatatgctg gctgccatga acaaaggtgg ctataaagag    240

gtcatcagta tatgaaacag ccccctgctg tccattcctt attccataga aaagccttga    300

cttgaggtta gattttttttt atattttgtt ttgtgttatt tttttcttta acatccctaa    360

aattttcctt acatgtttta ctagccagat ttttcctcct ctcctgacta ctcccagtca    420

tagctgtccc tcttctctta tgaagatc                                        448
```

<210> SEQ ID NO 22
<211> LENGTH: 577
<212> TYPE: DNA
<213> ORGANISM: Artificial Sequence
<220> FEATURE:
<223> OTHER INFORMATION: Envelope - CMV promoter - Transcription

<400> SEQUENCE: 22

```
acattgatta ttgactagtt attaatagta atcaattacg gggtcattag ttcatagccc     60

atatatggag ttccgcgtta cataacttac ggtaaatggc ccgcctggct gaccgcccaa    120

cgacccccgc ccattgacgt caataatgac gtatgttccc atagtaacgc caatagggac    180

tttccattga cgtcaatggg tggagtattt acggtaaact gcccacttgg cagtacatca    240

agtgtatcat atgccaagta cgccccctat tgacgtcaat gacggtaaat ggcccgcctg    300

gcattatgcc cagtacatga ccttatggga ctttcctact tggcagtaca tctacgtatt    360

agtcatcgct attaccatgg tgatgcggtt ttggcagtac atcaatgggc gtggatagcg    420

gtttgactca cggggatttc caagtctcca ccccattgac gtcaatggga gtttgttttg    480
```

-continued

```
gcaccaaaat caacgggact ttccaaaatg tcgtaacaac tccgccccat tgacgcaaat    540

gggcggtagg cgtgtacggt gggaggtcta tataagc                             577


<210> SEQ ID NO 23
<211> LENGTH: 573
<212> TYPE: DNA
<213> ORGANISM: Artificial Sequence
<220> FEATURE:
<223> OTHER INFORMATION: Envelope - Beta globin intron - Enhance gene
      expression

<400> SEQUENCE: 23

gtgagtttgg ggacccttga ttgttctttc tttttcgcta ttgtaaaatt catgttatat     60

ggagggggca aagttttcag ggtgttgttt agaatgggaa gatgtccctt gtatcaccat    120

ggaccctcat gataattttg tttctttcac tttctactct gttgacaacc attgtctcct    180

cttattttct tttcattttc tgtaactttt tcgttaaact ttagcttgca tttgtaacga    240

atttttaaat tcacttttgt ttatttgtca gattgtaagt actttctcta atcacttttt    300

tttcaaggca atcagggtat attatattgt acttcagcac agttttagag aacaattgtt    360

ataattaaat gataaggtag aatatttctg catataaatt ctggctggcg tggaaatatt    420

cttattggta gaaacaacta caccctggtc atcatcctgc ctttctcttt atggttacaa    480

tgatatacac tgtttgagat gaggataaaa tactctgagt ccaaaccggg cccctctgct    540

aaccatgttc atgccttctt ctctttccta cag                                 573


<210> SEQ ID NO 24
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 24

gaattcatga agtgcctttt gtacttagcc tttttattca ttggggtgaa ttgcaagttc     60

accatagttt ttccacacaa ccaaaaagga aactggaaaa atgttccttc taattaccat    120

tattgcccgt caagctcaga tttaaattgg cataatgact taataggcac agccttacaa    180

gtcaaaatgc ccaagagtca caaggctatt caagcagacg gttggatgtg tcatgcttcc    240

aaatgggtca ctacttgtga tttccgctgg tatggaccga agtatataac acattccatc    300

cgatccttca ctccatctgt agaacaatgc aaggaaagca ttgaacaaac gaaacaagga    360

acttggctga atccaggctt ccctcctcaa agttgtggat atgcaactgt gacggatgcc    420

gaagcagtga ttgtccaggt gactcctcac catgtgctgg ttgatgaata cacaggagaa    480

tgggttgatt cacagttcat caacggaaaa tgcagcaatt acatatgccc cactgtccat    540

aactctacaa cctggcattc tgactataag gtcaaagggc tatgtgattc taacctcatt    600

tccatggaca tcaccttctt ctcagaggac ggagagctat catccctggg aaaggagggc    660

acagggttca gaagtaacta ctttgcttat gaaactggag gcaaggcctg caaaatgcaa    720

tactgcaagc attggggagt cagactccca tcaggtgtct ggttcgagat ggctgataag    780

gatctctttg ctgcagccag attccctgaa tgcccagaag ggtcaagtat ctctgctcca    840

tctcagacct cagtggatgt aagtctaatt caggacgttg agaggatctt ggattattcc    900

ctctgccaag aaacctggag caaaatcaga gcgggtcttc caatctctcc agtggatctc    960

agctatcttg ctcctaaaaa cccaggaacc ggtcctgctt tcaccataat caatggtacc   1020
```

-continued

```
ctaaaatact ttgagaccag atacatcaga gtcgatattg ctgctccaat cctctcaaga   1080

atggtcggaa tgatcagtgg aactaccaca gaaagggaac tgtgggatga ctgggcacca   1140

tatgaagacg tggaaattgg acccaatgga gttctgagga ccagttcagg atataagttt   1200

cctttataca tgattggaca tggtatgttg gactccgatc ttcatcttag ctcaaaggct   1260

caggtgttcg aacatcctca cattcaagac gctgcttcgc aacttcctga tgatgagagt   1320

ttatttttg gtgatactgg gctatccaaa aatccaatcg agcttgtaga aggttggttc   1380

agtagttgga aaagctctat tgcctctttt ttctttatca tagggttaat cattggacta   1440

ttcttggttc tccgagttgg tatccatctt tgcattaaat taaagcacac caagaaaaga   1500

cagatttata cagacataga gatgagaatt c                                  1531
```

<210> SEQ ID NO 25
<211> LENGTH: 450
<212> TYPE: DNA
<213> ORGANISM: Artificial Sequence
<220> FEATURE:
<223> OTHER INFORMATION: Envelope - Rabbit beta globin poly A - RNA stability

<400> SEQUENCE: 25

```
agatcttttt ccctctgcca aaaattatgg ggacatcatg aagccccttg agcatctgac     60

ttctggctaa taaaggaaat ttattttcat tgcaatagtg tgttggaatt ttttgtgtct    120

ctcactcgga aggacatatg ggagggcaaa tcatttaaaa catcagaatg agtatttggt    180

ttagagtttg gcaacatatg cccatatgct ggctgccatg aacaaaggtt ggctataaag    240

aggtcatcag tatatgaaac agccccctgc tgtccattcc ttattccata gaaaagcctt    300

gacttgaggt tagatttttt ttatattttg ttttgtgtta tttttttctt taacatccct    360

aaaattttcc ttacatgttt tactagccag atttttcctc ctctcctgac tactcccagt    420

catagctgtc cctcttctct tatggagatc                                     450
```

<210> SEQ ID NO 26
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 26

```
gaattcatga atttgccagg aagatggaaa ccaaaaatga tagggggaat tggaggtttt     60

atcaaagtaa gacagtatga tcagatactc atagaaatct gcggacataa agctataggt    120

acagtattag taggacctac acctgtcaac ataattggaa gaaatctgtt gactcagatt    180

ggctgcactt taaattttcc cattagtcct attgagactg taccagtaaa attaaagcca    240

ggaatggatg gcccaaaagt taaacaatgg ccattgacag aagaaaaaat aaaagcatta    300

gtagaaattt gtacagaaat ggaaaaggaa ggaaaaattt caaaaattgg gcctgaaaat    360

ccatacaata ctccagtatt tgccataaag aaaaaagaca gtactaaatg gagaaaatta    420

gtagatttca gagaacttaa taagagaact caagatttct gggaagttca attaggaata    480

ccacatcctg cagggttaaa acagaaaaaa tcagtaacag tactggatgt gggcgatgca    540

tatttttcag ttcccttaga taaagacttc aggaagtata ctgcatttac catacctagt    600

ataaacaatg agacaccagg gattagatat cagtacaatg tgcttccaca gggatggaaa    660

ggatcaccag caatattcca gtgtagcatg acaaaaatct tagagccttt tagaaaacaa    720
```

-continued

```
aatccagaca tagtcatcta tcaatacatg gatgatttgt atgtaggatc tgacttagaa    780

atagggcagc atagaacaaa aatagaggaa ctgagacaac atctgttgag gtggggattt    840

accacaccag acaaaaaaca tcagaaagaa cctccattcc tttggatggg ttatgaactc    900

catcctgata aatggacagt acagcctata gtgctgccag aaaaggacag ctggactgtc    960

aatgacatac agaaattagt gggaaaattg aattgggcaa gtcagattta tgcagggatt   1020

aaagtaaggc aattatgtaa acttcttagg ggaaccaaag cactaacaga agtagtacca   1080

ctaacagaag aagcagagct agaactggca gaaaacaggg agattctaaa agaaccggta   1140

catggagtgt attatgaccc atcaaaagac ttaatagcag aaatacagaa gcaggggcaa   1200

ggccaatgga catatcaaat ttatcaagag ccatttaaaa atctgaaaac aggaaagtat   1260

gcaagaatga agggtgccca cactaatgat gtgaaacaat taacagaggc agtacaaaaa   1320

atagccacag aaagcatagt aatatgggga aagactccta aatttaaatt acccatacaa   1380

aaggaaacat gggaagcatg gtggacagag tattggcaag ccacctggat tcctgagtgg   1440

gagtttgtca ataccccctcc cttagtgaag ttatggtacc agttagagaa agaacccata   1500

ataggagcag aaactttcta tgtagatggg gcagccaata gggaaactaa attaggaaaa   1560

gcaggatatg taactgacag aggaagacaa aaagttgtcc ccctaacgga cacaacaaat   1620

cagaagactg agttacaagc aattcatcta gctttgcagg attcgggatt agaagtaaac   1680

atagtgacag actcacaata tgcattggga atcattcaag cacaaccaga taagagtgaa   1740

tcagagttag tcagtcaaat aatagagcag ttaataaaaa aggaaaaagt ctacctggca   1800

tgggtaccag cacacaaagg aattggagga aatgaacaag tagataaatt ggtcagtgct   1860

ggaatcagga aagtactatt tttagatgga atagataagg cccaagaaga acatgagaaa   1920

tatcacagta attggagagc aatggctagt gattttaacc taccacctgt agtagcaaaa   1980

gaaatagtag ccagctgtga taaatgtcag ctaaaagggg aagccatgca tggacaagta   2040

gactgtagcc caggaatatg gcagctagat tgtacacatt tagaaggaaa agttatcttg   2100

gtagcagttc atgtagccag tggatatata gaagcagaag taattccagc agagacaggg   2160

caagaaacag catacttcct cttaaaatta gcaggaagat ggccagtaaa aacagtacat   2220

acagacaatg gcagcaattt caccagtact acagttaagg ccgcctgttg gtgggcgggg   2280

atcaagcagg aatttggcat tccctacaat ccccaaagtc aaggagtaat agaatctatg   2340

aataaagaat taaagaaaat tataggacag gtaagagatc aggctgaaca tcttaagaca   2400

gcagtacaaa tggcagtatt catccacaat tttaaaagaa aaggggggat tgggggggtac   2460

agtgcagggg aaagaatagt agacataata gcaacagaca tacaaactaa agaattacaa   2520

aaacaaatta caaaaattca aaattttcgg gtttattaca gggacagcag agatccagtt   2580

tggaaaggac cagcaaagct cctctggaaa ggtgaagggg cagtagtaat acaagataat   2640

agtgacataa aagtagtgcc aagaagaaaa gcaaagatca tcagggatta tggaaaacag   2700

atggcaggtg atgattgtgt ggcaagtaga caggatgagg attaa                   2745
```

<210> SEQ ID NO 27
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 27

-continued

```
tctagaatgg caggaagaag cggagacagc gacgaagagc tcatcagaac agtcagactc     60

atcaagcttc tctatcaaag caacccacct cccaatcccg aggggacccg acaggcccga    120

aggaatagaa gaagaaggtg gagagagaga cagagacaga tccattcgat tagtgaacgg    180

atccttggca cttatctggg acgatctgcg gagcctgtgc ctcttcagct accaccgctt    240

gagagactta ctcttgattg taacgaggat tgtggaactt ctgggacgca gggggtggga    300

agccctcaaa tattggtgga atctcctaca atattggagt caggagctaa agaatagagg    360

agctttgttc cttgggttct tgggagcagc aggaagcact atgggcgcag cgtcaatgac    420

gctgacggta caggccagac aattattgtc tggtatagtg cagcagcaga acaatttgct    480

gagggctatt gaggcgcaac agcatctgtt gcaactcaca gtctggggca tcaagcagct    540

ccaggcaaga atcctggctg tggaaagata cctaaaggat caacagctcc tagatctttt    600

tccctctgcc aaaaattatg gggacatcat gaagcccctt gagcatctga cttctggcta    660

ataaaggaaa tttattttca ttgcaatagt gtgttggaat tttttgtgtc tctcactcgg    720

aaggacatat gggagggcaa atcatttaaa acatcagaat gagtatttgg tttagagttt    780

ggcaacatat gccatatgct ggctgccatg aacaaaggtg gctataaaga ggtcatcagt    840

atatgaaaca gccccctgct gtccattcct tattccatag aaaagccttg acttgaggtt    900

agattttttt tatattttgt tttgtgttat ttttttcttt aacatcccta aaattttcct    960

tacatgtttt actagccaga tttttcctcc tctcctgact actcccagtc atagctgtcc   1020

ctcttctctt atgaagatcc ctcgacctgc agcccaagct tggcgtaatc atggtcatag   1080

ctgtttcctg tgtgaaattg ttatccgctc acaattccac acaacatacg agccggaagc   1140

ataaagtgta aagcctgggg tgcctaatga gtgagctaac tcacattaat tgcgttgcgc   1200

tcactgcccg ctttccagtc gggaaacctg tcgtgccagc ggatccgcat ctcaattagt   1260

cagcaaccat agtcccgccc ctaactccgc ccatcccgcc cctaactccg cccagttccg   1320

cccattctcc gccccatggc tgactaattt tttttattta tgcagaggcc gaggccgcct   1380

cggcctctga gctattccag aagtagtgag gaggcttttt tggaggccta ggcttttgca   1440

aaaagctaac ttgtttattg cagcttataa tggttacaaa taaagcaata gcatcacaaa   1500

tttcacaaat aaagcatttt tttcactgca ttctagttgt ggtttgtcca aactcatcaa   1560

tgtatcttat cagcggccgc cccggg                                        1586
```

```
<210> SEQ ID NO 28
<211> LENGTH: 1614
<212> TYPE: DNA
<213> ORGANISM: Artificial Sequence
<220> FEATURE:
<223> OTHER INFORMATION: DNA fragment containing the CAG
      enhancer/promoter/intron sequence

<400> SEQUENCE: 28

acgcgttagt tattaatagt aatcaattac ggggtcatta gttcatagcc catatatgga     60

gttccgcgtt acataactta cggtaaatgg cccgcctggc tgaccgccca acgacccccg    120

cccattgacg tcaataatga cgtatgttcc catagtaacg ccaataggga ctttccattg    180

acgtcaatgg gtggactatt tacggtaaac tgcccacttg gcagtacatc aagtgtatca    240

tatgccaagt acgcccccta ttgacgtcaa tgacggtaaa tggcccgcct ggcattatgc    300

ccagtacatg accttatggg actttcctac ttggcagtac atctacgtat tagtcatcgc    360

tattaccatg gtcgaggtg agccccacgt tctgcttcac tctccccatc tcccccccct    420
```

-continued

```
ccccaccccc aattttgtat ttatttattt tttaattatt ttgtgcagcg atgggggcgg    480

gggggggggg ggcgcgcgcc aggcggggcg gggcggggcg aggggcgggg cggggcgagg    540

cggagaggtg cggcggcagc caatcagagc ggcgcgctcc gaaagtttcc ttttatggcg    600

aggcggcggc ggcggcggcc ctataaaaag cgaagcgcgc ggcgggcggg agtcgctgcg    660

ttgccttcgc cccgtgcccc gctccgcgcc gcctcgcgcc gcccgccccg gctctgactg    720

accgcgttac tcccacaggt gagcgggcgg gacggccctt ctcctccggg ctgtaattag    780

cgcttggttt aatgacggct cgtttctttt ctgtggctgc gtgaaagcct taaagggctc    840

cgggagggcc ctttgtgcgg gggggagcgg ctcggggggt gcgtgcgtgt gtgtgtgcgt    900

ggggagcgcc gcgtgcggcc cgcgctgccc ggcggctgtg agcgctgcgg gcgcggcgcg    960

gggctttgtg cgctccgcgt gtgcgcgagg ggagcgcggc cgggggcggt gccccgcggt   1020

gcgggggggc tgcgagggga acaaaggctg cgtgcggggt gtgtgcgtgg gggggtgagc   1080

agggggtgtg ggcgcggcgg tcgggctgta accccccct gcaccccct ccccgagttg   1140

ctgagcacgg cccggcttcg ggtgcggggc tccgtgcggg gcgtggcgcg gggctcgccg   1200

tgccgggcgg ggggtggcgg caggtggggg tgccgggcgg ggcggggccg cctcgggccg   1260

gggagggctc gggggagggg cgcggcggcc ccggagcgcc ggcggctgtc gaggcgcggc   1320

gagccgcagc cattgccttt tatggtaatc gtgcgagagg gcgcagggac ttcctttgtc   1380

ccaaatctgg cggagccgaa atctgggagg cgccgccgca cccctctag cgggcgcggg   1440

cgaagcggtg cggcgccggc aggaaggaaa tgggcgggga gggccttcgt gcgtcgccgc   1500

gccgccgtcc ccttctccat ctccagcctc ggggctgccg caggggggacg gctgccttcg   1560

gggggacgg ggcagggcgg ggttcggctt ctggcgtgtg accggcggga attc          1614
```

<210> SEQ ID NO 29
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 29

```
caattgcgat gtacgggcca gatatacgcg tatctgaggg gactagggtg tgtttaggcg     60

aaaagcgggg cttcggttgt acgcggttag gagtcccctc aggatatagt agtttcgctt    120

ttgcataggg agggggaaat gtagtcttat gcaatacact tgtagtcttg caacatggta    180

acgatgagtt agcaacatgc cttacaagga gagaaaaagc accgtgcatg ccgattggtg    240

gaagtaaggt ggtacgatcg tgccttatta ggaaggcaac agacaggtct gacatggatt    300

ggacgaacca ctgaattccg cattgcagag ataattgtat ttaagtgcct agctcgatac    360

aataaacgcc atttgaccat tcaccacatt ggtgtgcacc tccaagctcg agctcgttta    420

gtgaaccgtc agatcgcctg gagacgccat ccacgctgtt ttgacctcca tagaagacac    480

cgggaccgat ccagcctccc ctcgaagcta gcgattaggc atctcctatg gcaggaagaa    540

gcggagacag cgacgaagaa ctcctcaagg cagtcagact catcaagttt ctctatcaaa    600

gcaacccacc tcccaatccc gaggggaccc gacaggcccg aaggaataga agaagaaggt    660

ggagagagag acagagacag atccattcga ttagtgaacg gatccttagc acttatctgg    720

gacgatctgc ggagcctgtg cctcttcagc taccaccgct tgagagactt actcttgatt    780

gtaacgagga ttgtggaact tctgggacgc agggggtggg aagccctcaa atattggtgg    840

aatctcctac aatattggag tcaggagcta aagaatagtc taga                     884
```

<210> SEQ ID NO 30
<211> LENGTH: 1227
<212> TYPE: DNA
<213> ORGANISM: Artificial Sequence
<220> FEATURE:
<223> OTHER INFORMATION: RRE/rabbit poly A beta globin

<400> SEQUENCE: 30
tctagaagga gctttgttcc ttgggttctt gggagcagca ggaagcacta tgggcgcagc 60
gtcaatgacg ctgacggtac aggccagaca attattgtct ggtatagtgc agcagcagaa 120
caatttgctg agggctattg aggcgcaaca gcatctgttg caactcacag tctggggcat 180
caagcagctc caggcaagaa tcctggctgt ggaaagatac ctaaaggatc aacagctcct 240
agatcttttt ccctctgcca aaaattatgg ggacatcatg aagccccttg agcatctgac 300
ttctggctaa taaaggaaat ttattttcat tgcaatagtg tgttggaatt ttttgtgtct 360
ctcactcgga aggacatatg ggagggcaaa tcatttaaaa catcagaatg agtatttggt 420
ttagagtttg gcaacatatg ccatatgctg gctgccatga acaaaggtgg ctataaagag 480
gtcatcagta tatgaaacag ccccctgctg tccattcctt attccataga aaagccttga 540
cttgaggtta gatttttttt atattttgtt ttgtgttatt tttttcttta acatccctaa 600
aattttcctt acatgtttta ctagccagat ttttcctcct ctcctgacta ctcccagtca 660
tagctgtccc tcttctctta tgaagatccc tcgacctgca gcccaagctt ggcgtaatca 720
tggtcatagc tgtttcctgt gtgaaattgt tatccgctca caattccaca caacatacga 780
gccggaagca taaagtgtaa agcctggggt gcctaatgag tgagctaact cacattaatt 840
gcgttgcgct cactgcccgc tttccagtcg ggaaacctgt cgtgccagcg gatccgcatc 900
tcaattagtc agcaaccata gtcccgcccc taactccgcc catcccgccc ctaactccgc 960
ccagttccgc ccattctccg ccccatggct gactaatttt ttttatttat gcagaggccg 1020
aggccgcctc ggcctctgag ctattccaga agtagtgagg aggctttttt ggaggcctag 1080
gcttttgcaa aaagctaact tgtttattgc agcttataat ggttacaaat aaagcaatag 1140
catcacaaat ttcacaaata aagcattttt ttcactgcat tctagttgtg gtttgtccaa 1200
actcatcaat gtatcttatc acccggg 1227

<210> SEQ ID NO 31
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 31
ccggtgccta gagaaggtgg cgcggggtaa actgggaaag tgatgtcgtg tactggctcc 60
gcctttttcc cgagggtggg ggagaaccgt atataagtgc agtagtcgcc gtgaacgttc 120
tttttcgcaa cgggtttgcc gccagaacac aggtaagtgc cgtgtgtggt tcccgcgggc 180
ctggcctctt tacgggttat ggcccttgcg tgccttgaat tacttccacg cccctggctg 240
cagtacgtga ttcttgatcc cgagcttcgg gttggaagtg ggtgggagag ttcgaggcct 300
tgcgcttaag gagccccttc gcctcgtgct tgagttgagg cctggcctgg gcgctggggc 360
cgccgcgtgc gaatctggtg gcaccttcgc gcctgtctcg ctgctttcga taagtctcta 420
gccatttaaa atttttgatg acctgctgcg acgctttttt tctggcaaga tagtcttgta 480
aatgcgggcc aagatctgca cactggtatt tcggtttttg gggccgcggg cggcgacggg 540
gcccgtgcgt cccagcgcac atgttcggcg aggcggggcc tgcgagcgcg gccaccgaga 600
atcggacggg ggtagtctca agctggccgg cctgctctgg tgcctggcct cgcgccgccg 660
tgtatcgccc cgccctgggc ggcaaggctg gcccggtcgg caccagttgc gtgagcggaa 720
agatggccgc ttcccggccc tgctgcaggg agctcaaaat ggaggacgcg gcgctcggga 780
gagcgggcgg gtgagtcacc cacacaaagg aaaagggcct ttccgtcctc agccgtcgct 840
tcatgtgact ccacggagta ccgggcgccg tccaggcacc tcgattagtt ctcgagcttt 900
tggagtacgt cgtctttagg ttggggggag gggttttatg cgatggagtt tccccacact 960
gagtgggtgg agactgaagt taggccagct tggcacttga tgtaattctc cttggaattt 1020
gccctttttg agtttggatc ttggttcatt ctcaagcctc agacagtggt tcaaagtttt 1080
tttcttccat ttcaggtgtc gtga 1104

<210> SEQ ID NO 32
<211> LENGTH: 511
<212> TYPE: DNA
<213> ORGANISM: Artificial Sequence
<220> FEATURE:
<223> OTHER INFORMATION: Promoter - PGK

<400> SEQUENCE: 32
ggggttgggg ttgcgccttt tccaaggcag ccctgggttt gcgcagggac gcggctgctc 60
tgggcgtggt tccgggaaac gcagcggcgc cgaccctggg tctcgcacat tcttcacgtc 120
cgttcgcagc gtcacccgga tcttcgccgc taccettgtg ggcccccegg cgacgcttcc 180 tgctccgccc ctaagtcggg aaggttcctt gcggttcgcg gcgtgccgga cgtgacaaac 240
ggaagccgca cgtctcacta gtaccctcgc agacggacag cgccagggag caatggcagc 300
gcgccgaccg cgatgggctg tggccaatag cggctgctca gcagggcgcg ccgagagcag 360
cggccgggaa ggggcggtgc gggaggcggg gtgtggggcg gtagtgtggg ccctgttcct 420
gcccgcgcgg tgttccgcat tctgcaagcc tccggagcgc acgtcggcag tcggctccct 480
cgttgaccga atcaccgacc tctctcccca g 511

<210> SEQ ID NO 33
<211> LENGTH: 1162
<212> TYPE: DNA
<213> ORGANISM: Artificial Sequence
<220> FEATURE:
<223> OTHER INFORMATION: Promoter - UbC

<400> SEQUENCE: 33
gcgccgggtt ttggcgcctc ccgcgggcgc ccccctcctc acggcgagcg ctgccacgtc 60
agacgaaggg cgcaggagcg ttcctgatcc ttccgcccgg acgctcagga cagcggcccg 120
ctgctcataa gactcggcct tagaacccca gtatcagcag aaggacattt taggacggga 180
cttgggtgac tctagggcac tggttttctt tccagagagc ggaacaggcg aggaaaagta 240
gtcccttctc ggcgattctg cggagggatc tccgtggggc ggtgaacgcc gatgattata 300
taaggacgcg ccgggtgtgg cacagctagt tccgtcgcag ccgggatttg ggtcgcggtt 360
cttgtttgtg gatcgctgtg atcgtcactt ggtgagttgc gggctgctgg gctggccggg 420
gctttcgtgg ccgccgggcc gctcggtggg acggaagcgt gtggagagac cgccaagggc 480
tgtagtctgg gtccgcgagc aaggttgccc tgaactgggg gttgggggga gcgcacaaaa 540
tggcggctgt tcccgagtct tgaatggaag acgcttgtaa ggcgggctgt gaggtcgttg 600
aaacaaggtg gggggcatgg tgggcggcaa gaacccaagg tcttgaggcc ttcgctaatg 660
cgggaaagct cttattcggg tgagatgggc tggggcacca tctggggacc ctgacgtgaa 720
gtttgtcact gactggagaa ctcgggtttg tcgtctggtt gcgggggcgg cagttatgcg 780
gtgccgttgg gcagtgcacc cgtacctttg ggagcgcgcg cctcgtcgtg tcgtgacgtc 840
acccgttctg ttggcttata atgcagggtg gggccacctg ccggtaggtg tgcggtaggc 900
ttttctccgt cgcaggacgc agggttcggg cctagggtag gctctcctga atcgacaggc 960
gccggacctc tggtgagggg agggataagt gaggcgtcag tttctttggt cggttttatg 1020
tacctatctt cttaagtagc tgaagctccg gttttgaact atgcgctcgg ggttggcgag 1080
tgtgttttgt gaagtttttt aggcaccttt tgaaatgtaa tcatttgggt caatatgtaa 1140
ttttcagtgt tagactagta aa 1162

<210> SEQ ID NO 34
<211> LENGTH: 120
<212> TYPE: DNA
<213> ORGANISM: Artificial Sequence
<220> FEATURE:
<223> OTHER INFORMATION: Poly A - SV40

<400> SEQUENCE: 34
gtttattgca gcttataatg gttacaaata aagcaatagc atcacaaatt tcacaaataa 60
agcatttttt tcactgcatt ctagttgtgg tttgtccaaa ctcatcaatg tatcttatca 120

<210> SEQ ID NO 35
<211> LENGTH: 227
<212> TYPE: DNA
<213> ORGANISM: Artificial Sequence
<220> FEATURE:
<223> OTHER INFORMATION: Poly A - bGH

<400> SEQUENCE: 35
gactgtgcct tctagttgcc agccatctgt tgtttgcccc tcccccgtgc cttccttgac 60
cctggaaggt gccactccca ctgtcctttc ctaataaaat gaggaaattg catcgcattg 120
tctgagtagg tgtcattcta ttctgggggg tggggtgggg caggacagca agggggagga 180
ttgggaagac aatagcaggc atgctgggga tgcggtgggc tctatgg 227

<210> SEQ ID NO 36
<211> LENGTH: 1695
<212> TYPE: DNA
<213> ORGANISM: Artificial Sequence
<220> FEATURE:
<223> OTHER INFORMATION: Envelope - RD114

<400> SEQUENCE: 36
atgaaactcc caacaggaat ggtcatttta tgtagcctaa taatagttcg ggcagggttt 60
gacgaccccc gcaaggctat cgcattagta caaaaacaac atggtaaacc atgcgaatgc 120
agcggagggc aggtatccga ggccccaccg aactccatcc aacaggtaac ttgcccaggc 180
aagacggcct acttaatgac caaccaaaaa tggaaatgca gagtcactcc aaaaaatctc 240
acccctagcg ggggagaact ccagaactgc ccctgtaaca ctttccagga ctcgatgcac 300
agttcttgtt atactgaata ccggcaatgc agggcgaata ataagacata ctacacggcc 360
accttgctta aaatacggtc tgggagcctc aacgaggtac agatattaca aaaccccaat 420
cagctcctac agtccccttg taggggctct ataaatcagc ccgtttgctg gagtgccaca 480
gcccccatcc atatctccga tggtggagga cccctcgata ctaagagagt gtggacagtc 540
caaaaaaggc tagaacaaat tcataaggct atgcatcctg aacttcaata ccaccccttta 600 gccctgccca aagtcagaga tgaccttagc cttgatgcac ggacttttga tatcctgaat 660
accactttta ggttactcca gatgtccaat tttagccttg cccaagattg ttggctctgt 720
ttaaaactag gtaccccctac ccctcttgcg atacccactc cctctttaac ctactcccta 780
gcagactccc tagcgaatgc ctcctgtcag attatacctc ccctcttggt tcaaccgatg 840
cagttctcca actcgtcctg tttatcttcc cctttcatta acgatacgga acaaatagac 900
ttaggtgcag tcacctttac taactgcacc tctgtagcca atgtcagtag tcctttatgt 960
gccctaaacg ggtcagtctt cctctgtgga aataacatgg catacaccta tttaccccaa 1020
aactggacag gactttgcgt ccaagcctcc ctcctccccg acattgacat catcccgggg 1080
gatgagccag tccccattcc tgccattgat cattatatac atagacctaa acgagctgta 1140
cagttcatcc ctttactagc tggactggga atcaccgcag cattcaccac cggagctaca 1200
ggcctaggtg tctccgtcac ccagtataca aaattatccc atcagttaat atctgatgtc 1260
caagtcttat ccggtaccat acaagattta caagaccagg tagactcgtt agctgaagta 1320
gttctccaaa ataggagggg actggaccta ctaacggcag aacaaggagg aatttgttta 1380
gccttacaag aaaaatgctg tttttatgct aacaagtcag gaattgtgag aaacaaaata 1440
agaaccctac aagaagaatt acaaaaacgc agggaaagcc tggcatccaa ccctctctgg 1500
accgggctgc agggctttct tccgtacctc ctacctctcc tgggacccct actcaccctc 1560
ctactcatac taaccattgg gccatgcgtt ttcaatcgat tggtccaatt tgttaaagac 1620
aggatctcag tggtccaggc tctggttttg actcagcaat atcaccagct aaaacccata 1680
gagtacgagc catga 1695

<210> SEQ ID NO 37
<211> LENGTH: 2013
<212> TYPE: DNA
<213> ORGANISM: Artificial Sequence
<220> FEATURE:
<223> OTHER INFORMATION: Envelope - GALV

<400> SEQUENCE: 37
atgcttctca cctcaagccc gcaccacctt cggcaccaga tgagtcctgg gagctggaaa 60
agactgatca tcctcttaag ctgcgtattc ggagacggca aaacgagtct gcagaataag 120
aacccccacc agcctgtgac cctcacctgg caggtactgt cccaaactgg ggacgttgtc 180
tgggacaaaa aggcagtcca gcccctttgg acttggtggc cctctcttac acctgatgta 240
tgtgccctgg cggccggtct tgagtcctgg gatatcccgg gatccgatgt atcgtcctct 300
aaaagagtta gacctcctga ttcagactat actgccgctt ataagcaaat cacctgggga 360
gccatagggt gcagctaccc tcgggctagg accaggatgg caaattcccc cttctacgtg 420
tgtccccgag ctggccgaac ccattcagaa gctaggaggt gtggggggct agaatcccta 480
tactgtaaag aatggagttg tgagaccacg ggtaccgttt attggcaacc caagtcctca 540
tgggacctca taactgtaaa atgggaccaa aatgtgaaat gggagcaaaa atttcaaaag 600
tgtgaacaaa ccggctggtg taacccccctc aagatagact tcacagaaaa aggaaaactc 660
tccagagatt ggataacgga aaaaacctgg gaattaaggt tctatgtata tggacaccca 720
ggcatacagt tgactatccg cttagaggtc actaacatgc cggttgtggc agtgggccca 780
gaccctgtcc ttgcggaaca gggacctcct agcaagcccc tcactctccc tctctcccca 840
cggaaagcgc cgcccacccc tctacccccg gcggctagtg agcaaacccc tgcggtgcat 900
ggagaaactg ttaccctaaa ctctccgcct cccaccagtg gcgaccgact ctttggcctt 960
gtgcaggggg ccttcctaac cttgaatgct accaacccag gggccactaa gtcttgctgg 1020
ctctgtttgg gcatgagccc cccttattat gaagggatag cctcttcagg agaggtcgct 1080
tatacctcca accatacccg atgccactgg ggggcccaag gaaagcttac cctcactgag 1140
gtctccggac tcgggtcatg catagggaag gtgcctctta cccatcaaca tctttgcaac 1200
cagaccttac ccatcaattc ctctaaaaac catcagtatc tgctcccctc aaaccatagc 1260
tggtgggcct gcagcactgg cctcaccccc tgcctctcca cctcagtttt taatcagtct 1320
aaagacttct gtgtccaggt ccagctgatc cccgcatct attaccattc tgaagaaacc 1380
ttgttacaag cctatgacaa atcacccccc aggtttaaaa gagagcctgc ctcacttacc 1440
ctagctgtct tcctggggtt agggattgcg gcaggtatag gtactggctc aaccgcccta 1500
attaaagggc ccatagacct ccagcaaggc ctaaccagcc tccaaatcgc cattgacgct 1560
gacctccggg cccttcagga ctcaatcagc aagctagagg actcactgac ttccctatct 1620
gaggtagtac tccaaaatag gagaggcctt gacttactat tccttaaaga aggaggcctc 1680
tgcgcggccc taaaagaaga gtgctgtttt tatgtagacc actcaggtgc agtacgagac 1740
tccatgaaaa aacttaaaga aagactagat aaaagacagt tagagcgcca gaaaaaccaa 1800
aactggtatg aagggtggtt caataactcc ccttggttta ctaccctact atcaaccatc 1860
gctgggcccc tattgctcct ccttttgtta ctcactcttg ggccctgcat catcaataaa 1920
ttaatccaat tcatcaatga taggataagt gcagtcaaaa ttttagtcct tagacagaaa 1980
tatcagaccc tagataacga ggaaaacctt taa 2013

<210> SEQ ID NO 38
<211> LENGTH: 1530
<212> TYPE: DNA
<213> ORGANISM: Artificial Sequence
<220> FEATURE:
<223> OTHER INFORMATION: Envelope - FUG

<400> SEQUENCE: 38
atggttccgc aggttctttt gtttgtactc cttctgggtt tttcgttgtg tttcgggaag 60
ttccccattt acacgatacc agacgaactt ggtccctgga gccctattga catacaccat 120
ctcagctgtc caaataacct ggttgtggag gatgaaggat gtaccaacct gtccgagttc 180
tcctacatgg aactcaaagt gggatacatc tcagccatca aagtgaacgg gttcacttgc 240
acaggtgttg tgacagaggc agagacctac accaactttg ttggttatgt cacaaccaca 300
ttcaagagaa agcatttccg ccccacccca gacgcatgta gagccgcgta taactggaag 360
atggccggtg accccagata tgaagagtcc ctacacaatc catacccga ctaccactgg 420 cttcgaactg taagaaccac caaagagtcc ctcattatca tatccccaag tgtgacagat 480
ttggacccat atgacaaatc ccttcactca agggtcttcc ctggcggaaa gtgctcagga 540
ataacggtgt cctctaccta ctgctcaact aaccatgatt acaccatttg gatgcccgag 600
aatccgagac caaggacacc ttgtgacatt tttaccaata gcagagggaa gagagcatcc 660
aacgggaaca agacttgcgg ctttgtggat gaaagaggcc tgtataagtc tctaaaagga 720
gcatgcaggc tcaagttatg tggagttctt ggacttagac ttatggatgg aacatgggtc 780
gcgatgcaaa catcagatga gaccaaatgg tgccctccag atcagttggt gaatttgcac 840

-continued

```
gactttcgct cagacgagat cgagcatctc gttgtggagg agttagttaa gaaaagagag    900

gaatgtctgg atgcattaga gtccatcatg accaccaagt cagtaagttt cagacgtctc    960

agtcacctga gaaaacttgt cccagggttt ggaaaagcat ataccatatt caacaaaacc   1020

ttgatggagg ctgatgctca ctacaagtca gtccggacct ggaatgagat catcccctca   1080

aaagggtgtt tgaaagttgg aggaaggtgc catcctcatg tgaacggggt gtttttcaat   1140

ggtataatat tagggcctga cgaccatgtc ctaatcccag agatgcaatc atccctcctc   1200

cagcaacata tggagttgtt ggaatcttca gttatccccc tgatgcaccc cctggcagac   1260

ccttctacag ttttcaaaga aggtgatgag gctgaggatt ttgttgaagt tcacctcccc   1320

gatgtgtaca aacagatctc aggggttgac ctgggtctcc cgaactgggg aaagtatgta   1380

ttgatgactg caggggccat gattggcctg gtgttgatat tttccctaat gacatggtgc   1440

agagttggta tccatctttg cattaaatta aagcacacca agaaaagaca gatttataca   1500

gacatagaga tgaaccgact tggaaagtaa                                    1530
```

```
<210> SEQ ID NO 39
<211> LENGTH: 1497
<212> TYPE: DNA
<213> ORGANISM: Artificial Sequence
<220> FEATURE:
<223> OTHER INFORMATION: Envelope - LCMV

<400> SEQUENCE: 39

atgggtcaga ttgtgacaat gtttgaggct ctgcctcaca tcatcgatga ggtgatcaac     60

attgtcatta ttgtgcttat cgtgatcacg ggtatcaagg ctgtctacaa ttttgccacc    120

tgtgggatat tcgcattgat cagtttccta cttctggctg gcaggtcctg tggcatgtac    180

ggtcttaagg gacccgacat ttacaaagga gtttaccaat ttaagtcagt ggagtttgat    240

atgtcacatc tgaacctgac catgcccaac gcatgttcag ccaacaactc ccaccattac    300

atcagtatgg ggacttctgg actagaattg accttcacca atgattccat catcagtcac    360

aacttttgca atctgacctc tgccttcaac aaaaagacct ttgaccacac actcatgagt    420

atagtttcga gcctacacct cagtatcaga gggaactcca actataaggc agtatcctgc    480

gacttcaaca atggcataac catccaatac aacttgacat tctcagatcg acaaagtgct    540

cagagccagt gtagaacctt cagaggtaga gtcctagata tgtttagaac tgccttcggg    600

gggaaataca tgaggagtgg ctggggctgg acaggctcag atggcaagac cacctggtgt    660

agccagacga gttaccaata cctgattata caaaatagaa cctgggaaaa ccactgcaca    720

tatgcaggtc cttttgggat gtccaggatt ctcctttccc aagagaagac taagttcttc    780

actaggagac tagcgggcac attcacctgg actttgtcag actcttcagg ggtggagaat    840

ccaggtggtt attgcctgac caaatggatg attcttgctg cagagcttaa gtgtttcggg    900

aacacagcag ttgcgaaatg caatgtaaat catgatgccg aattctgtga catgctgcga    960

ctaattgact acaacaaggc tgctttgagt aagttcaaag aggacgtaga atctgccttg   1020

cacttattca aaacaacagt gaattctttg atttcagatc aactactgat gaggaaccac   1080

ttgagagatc tgatgggggt gccatattgc aattactcaa agttttggta cctagaacat   1140

gcaaagaccg gcgaaactag tgtccccaag tgctggcttg tcaccaatgg ttcttactta   1200

aatgagaccc acttcagtga tcaaatcgaa caggaagccg ataacatgat tacagagatg   1260

ttgaggaagg attacataaa gaggcagggg agtacccccc tagcattgat ggaccttctg   1320

atgttttcca catctgcata tctagtcagc atcttcctgc accttgtcaa aataccaaca   1380
```

cacaggcaca taaaaggtgg ctcatgtcca aagccacacc gattaaccaa caaaggaatt 1440
tgtagttgtg gtgcatttaa ggtgcctggt gtaaaaaccg tctggaaaag acgctga 1497

<210> SEQ ID NO 40
<211> LENGTH: 1692
<212> TYPE: DNA
<213> ORGANISM: Artificial Sequence
<220> FEATURE:
<223> OTHER INFORMATION: Envelope - FPV

<400> SEQUENCE: 40
atgaacactc aaatcctggt tttcgccctt gtggcagtca tccccacaaa tgcagacaaa 60
atttgtcttg gacatcatgc tgtatcaaat ggcaccaaag taaacacact cactgagaga 120
ggagtagaag ttgtcaatgc aacggaaaca gtggagcgga caaacatccc caaaatttgc 180
tcaaaaggga aaagaaccac tgatcttggc caatgcggac tgttagggac cattaccgga 240
ccacctcaat gcgaccaatt tctagaattt tcagctgatc taataatcga gagacgagaa 300
ggaaatgatg tttgttaccc ggggaagttt gttaatgaag aggcattgcg acaaatcctc 360
agaggatcag gtgggattga caaagaaaca atgggattca catatagtgg aataaggacc 420
aacggaacaa ctagtgcatg tagaagatca gggtcttcat tctatgcaga aatggagtgg 480
ctcctgtcaa atacagacaa tgctgctttc ccacaaatga caaaatcata caaaaacaca 540
aggagagaat cagctctgat agtctgggga atccaccatt caggatcaac caccgaacag 600
accaaactat atgggagtgg aaataaactg ataacagtcg ggagttccaa atatcatcaa 660
tcttttgtgc cgagtccagg aacacgaccg cagataaatg gccagtccgg acggattgat 720
tttcattggt tgatcttgga tcccaatgat acagttactt ttagtttcaa tggggctttc 780
atagctccaa atcgtgccag cttcttgagg ggaaagtcca tggggatcca gagcgatgtg 840
caggttgatg ccaattgcga aggggaatgc taccacagtg gagggactat aacaagcaga 900
ttgccttttc aaaacatcaa tagcagagca gttggcaaat gcccaagata tgtaaaacag 960
gaaagtttat tattggcaac tgggatgaag aacgttcccg aaccttccaa aaaaaggaaa 1020
aaaagaggcc tgtttggcgc tatagcaggg tttattgaaa atggttggga aggtctggtc 1080
gacgggtggt acggtttcag gcatcagaat gcacaaggag aaggaactgc agcagactac 1140
aaaagcaccc aatcggcaat tgatcagata accggaaagt taaatagact cattgagaaa 1200
accaaccagc aatttgagct aatagataat gaattcactg aggtggaaaa gcagattggc 1260
aatttaatta actggaccaa agactccatc acagaagtat ggtcttacaa tgctgaactt 1320
cttgtggcaa tggaaaacca gcacactatt gatttggctg attcagagat gaacaagctg 1380
tatgagcgag tgaggaaaca attaagggaa aatgctgaag aggatggcac tggttgcttt 1440
gaaatttttc ataaatgtga cgatgattgt atggctagta taaggaacaa tacttatgat 1500
cacagcaaat acagagaaga agcgatgcaa aatagaatac aaattgaccc agtcaaattg 1560
agtagtggct acaaagatgt gatactttgg tttagcttcg ggcatcatg ctttttgctt 1620 cttgccattg caatgggcct tgttttcata tgtgtgaaga acggaaacat gcggtgcact 1680
atttgtatat aa 1692

<210> SEQ ID NO 41
<211> LENGTH: 1266
<212> TYPE: DNA
<213> ORGANISM: Artificial Sequence
<220> FEATURE:

<223> OTHER INFORMATION: Envelope - RRV

<400> SEQUENCE: 41

```
agtgtaacag agcactttaa tgtgtataag gctactagac catacctagc acattgcgcc     60
gattgcgggg acgggtactt ctgctatagc ccagttgcta tcgaggagat ccgagatgag    120
gcgtctgatg gcatgcttaa gatccaagtc tccgcccaaa taggtctgga caaggcaggc    180
acccacgccc acacgaagct ccgatatatg gctggtcatg atgttcagga atctaagaga    240
gattccttga gggtgtacac gtccgcagcg tgctccatac atgggacgat gggacacttc    300
atcgtcgcac actgtccacc aggcgactac ctcaaggttt cgttcgagga cgcagattcg    360
cacgtgaagg catgtaaggt ccaatacaag cacaatccat tgccggtggg tagagagaag    420
ttcgtggtta gaccacactt tggcgtagag ctgccatgca cctcatacca gctgacaacg    480
gctcccaccg acgaggagat tgacatgcat acaccgccag atataccgga tcgcaccctg    540
ctatcacaga cggcgggcaa cgtcaaaata acagcaggcg gcaggactat caggtacaac    600
tgtacctgcg gccgtgacaa cgtaggcact accagtactg acaagaccat caacacatgc    660
aagattgacc aatgccatgc tgccgtcacc agccatgaca aatggcaatt tacctctcca    720
tttgttccca gggctgatca gacagctagg aaaggcaagg tacacgttcc gttccctctg    780
actaacgtca cctgccgagt gccgttggct cgagcgccgg atgccaccta tggtaagaag    840
gaggtgaccc tgagattaca cccagatcat ccgacgctct tctcctatag gagtttagga    900
gccgaaccgc acccgtacga ggaatgggtt gacaagttct ctgagcgcat catcccagtg    960
acggaagaag ggattgagta ccagtggggc aacaacccgc cggtctgcct gtgggcgcaa   1020
ctgacgaccg agggcaaacc ccatggctgg ccacatgaaa tcattcagta ctattatgga   1080
ctataccccg ccgccactat tgccgcagta tccggggcga gtctgatggc cctcctaact   1140
ctggcggcca catgctgcat gctggccacc gcgaggagaa agtgcctaac accgtacgcc   1200
ctgacgccag gagcggtggt accgttgaca ctggggctgc tttgctgcgc accgagggcg   1260
aatgca                                                              1266
```

<210> SEQ ID NO 42
<211> LENGTH: 1938
<212> TYPE: DNA
<213> ORGANISM: Artificial Sequence
<220> FEATURE:
<223> OTHER INFORMATION: Envelope - MLV 10A1

<400> SEQUENCE: 42

```
atggaaggtc cagcgttctc aaaacccctt aaagataaga ttaacccgtg gaagtcctta     60
atggtcatgg gggtctattt aagagtaggg atggcagaga gcccccatca ggtctttaat    120
gtaacctgga gagtcaccaa cctgatgact gggcgtaccg ccaatgccac ctccctttta    180
ggaactgtac aagatgcctt cccaagatta tattttgatc tatgtgatct ggtcggagaa    240
gagtgggacc cttcagacca ggaaccatat gtcgggtatg gctgcaaata ccccggaggg    300
agaaagcgga cccggacttt tgacttttac gtgtgccctg ggcataccgt aaaatcgggg    360
tgtgggggc caagagaggg ctactgtggt gaatggggtt gtgaaaccac cggacaggct    420
tactggaagc ccacatcatc atgggaccta atctccctta agcgcggtaa cacccccctgg    480
gacacgggat gctccaaaat ggcttgtggc ccctgctacg acctctccaa agtatccaat    540
tccttccaag ggctactcg agggggcaga tgcaaccctc tagtcctaga attcactgat    600
gcaggaaaaa aggctaattg ggacgggccc aaatcgtggg gactgagact gtaccggaca    660
```

ggaacagatc ctattaccat gttctccctg acccgccagg tcctcaatat agggccccgc 720
atccccattg ggcctaatcc cgtgatcact ggtcaactac ccccctcccg acccgtgcag 780
atcaggctcc ccaggcctcc tcagcctcct cctacaggcg cagcctctat agtccctgag 840
actgccccac cttctcaaca acctgggacg ggagacaggc tgctaaacct ggtagaagga 900
gcctatcagg cgcttaacct caccaatccc gacaagaccc aagaatgttg gctgtgctta 960
gtgtcgggac ctccttatta cgaaggagta gcggtcgtgg gcacttatac caatcattct 1020
accgccccgg ccagctgtac ggccacttcc caacataagc ttaccctatc tgaagtgaca 1080
ggacagggcc tatgcatggg agcactacct aaaactcacc aggccttatg taacaccacc 1140
caaagtgccg gctcaggatc ctactacctt gcagcacccg ctggaacaat gtgggcttgt 1200
agcactggat tgactccctg cttgtccacc acgatgctca atctaaccac agactattgt 1260
gtattagttg agctctggcc cagaataatt taccactccc ccgattatat gtatggtcag 1320
cttgaacagc gtaccaaata taagagggag ccagtatcgt tgaccctggc ccttctgcta 1380
ggaggattaa ccatgggagg gattgcagct ggaataggga cggggaccac tgccctaatc 1440
aaaacccagc agtttgagca gcttcacgcc gctatccaga cagacctcaa cgaagtcgaa 1500
aaatcaatta ccaacctaga aaagtcactg acctcgttgt ctgaagtagt cctacagaac 1560
cgaagaggcc tagatttgct cttcctaaaa gagggaggtc tctgcgcagc cctaaaagaa 1620
gaatgttgtt tttatgcaga ccacacggga ctagtgagag acagcatggc caaactaagg 1680
gaaaggctta atcagagaca aaaactattt gagtcaggcc aaggttggtt cgaagggcag 1740
tttaatagat ccccctggtt taccacctta atctccacca tcatgggacc tctaatagta 1800
ctcttactga tcttactctt tggaccctgc attctcaatc gattggtcca atttgttaaa 1860
gacaggatct cagtggtcca ggctctggtt ttgactcaac aatatcacca gctaaaacct 1920
atagagtacg agccatga 1938

<210> SEQ ID NO 43
<211> LENGTH: 2030
<212> TYPE: DNA
<213> ORGANISM: Artificial Sequence
<220> FEATURE:
<223> OTHER INFORMATION: Envelope - Ebola

<400> SEQUENCE: 43
atgggtgtta caggaatatt gcagttacct cgtgatcgat tcaagaggac atcattcttt 60
ctttgggtaa ttatcctttt ccaaagaaca ttttccatcc cacttggagt catccacaat 120
agcacattac aggttagtga tgtcgacaaa ctggtttgcc gtgacaaact gtcatccaca 180
aatcaattga gatcagttgg actgaatctc gaagggaatg gagtggcaac tgacgtgcca 240
tctgcaacta aaagatgggg cttcaggtcc ggtgtcccac caaaggtggt caattatgaa 300
gctggtgaat gggctgaaaa ctgctacaat cttgaaatca aaaaacctga cgggagtgag 360
tgtctaccag cagcgccaga cgggattcgg ggcttccccc ggtgccggta tgtgcacaaa 420
gtatcaggaa cgggaccgtg tgccggagac tttgccttcc acaaagaggg tgctttcttc 480
ctgtatgacc gacttgcttc cacagttatc taccgaggaa cgactttcgc tgaaggtgtc 540
gttgcatttc tgatactgcc ccaagctaag aaggacttct tcagctcaca ccccttgaga 600
gagccggtca atgcaacgga ggacccgtct agtggctact attctaccac aattagatat 660
caagctaccg gttttggaac caatgagaca gagtatttgt tcgaggttga caatttgacc 720
tacgtccaac ttgaatcaag attcacacca cagtttctgc tccagctgaa tgagacaata 780
tatacaagtg ggaaaaggag caataccacg ggaaaactaa tttggaaggt caaccccgaa 840
attgatacaa caatcgggga gtgggccttc tgggaaacta aaaaaacctc actagaaaaa 900
ttcgcagtga agagttgtct ttcacagctg tatcaaacag agccaaaaac atcagtggtc 960
agagtccggc gcgaacttct tccgacccag ggaccaacac aacaactgaa gaccacaaaa 1020
tcatggcttc agaaaattcc tctgcaatgg ttcaagtgca cagtcaagga agggaagctg 1080
cagtgtcgca tctgacaacc cttgccacaa tctccacgag tcctcaaccc cccacaacca 1140
aaccaggtcc ggacaacagc acccacaata cacccgtgta taaacttgac atctctgagg 1200
caactcaagt tgaacaacat caccgcagaa cagacaacga cagcacagcc tccgacactc 1260
cccccgccac gaccgcagcc ggacccctaa aagcagagaa caccaacacg agcaagggta 1320
ccgacctcct ggaccccgcc accacaacaa gtccccaaaa ccacagcgag accgctggca 1380
acaacaacac tcatcaccaa gataccggag aagagagtgc cagcagcggg aagctaggct 1440
taattaccaa tactattgct ggagtcgcag gactgatcac aggcgggagg agagctcgaa 1500
gagaagcaat tgtcaatgct caacccaaat gcaaccctaa tttacattac tggactactc 1560
aggatgaagg tgctgcaatc ggactggcct ggataccata tttcgggcca gcagccgagg 1620
gaatttacat agaggggctg atgcacaatc aagatggttt aatctgtggg ttgagacagc 1680
tggccaacga gacgactcaa gctcttcaac tgttcctgag agccacaacc gagctacgca 1740
ccttttcaat cctcaaccgt aaggcaattg atttcttgct gcagcgatgg ggcggcacat 1800
gccacatttt gggaccggac tgctgtatcg aaccacatga ttggaccaag aacataacag 1860
acaaaattga tcagattatt catgattttg ttgataaaac ccttccggac caggggggaca 1920 atgacaattg gtggacagga tggagacaat ggataccggc aggtattgga gttacaggcg 1980
ttataattgc agttatcgct ttattctgta tatgcaaatt tgtcttttag 2030

<210> SEQ ID NO 44
<211> LENGTH: 31
<212> TYPE: DNA
<213> ORGANISM: Artificial Sequence
<220> FEATURE:
<223> OTHER INFORMATION: Forward Primer to amplify Gag, Pol, and Integrase

<400> SEQUENCE: 44
taagcagaat tcatgaattt gccaggaaga t 31

<210> SEQ ID NO 45
<211> LENGTH: 36
<212> TYPE: DNA
<213> ORGANISM: Artificial Sequence
<220> FEATURE:
<223> OTHER INFORMATION: Reverse Primer to amplify Gag, Pol, and Integrase

<400> SEQUENCE: 45
ccatacaatg aatggacact aggcggccgc acgaat 36

<210> SEQ ID NO 46
<211> LENGTH: 21
<212> TYPE: DNA
<213> ORGANISM: Artificial Sequence
<220> FEATURE:
<223> OTHER INFORMATION: KIF11 Forward Primer

<400> SEQUENCE: 46
ccgttctgga gctgttgata a 21

<210> SEQ ID NO 47
<211> LENGTH: 23
<212> TYPE: DNA
<213> ORGANISM: Artificial Sequence
<220> FEATURE:
<223> OTHER INFORMATION: KIF11 Reverse Primer

<400> SEQUENCE: 47
tgttctttct acaagggcag taa 23

<210> SEQ ID NO 48
<211> LENGTH: 24
<212> TYPE: DNA
<213> ORGANISM: Artificial Sequence
<220> FEATURE:
<223> OTHER INFORMATION: KIF11 TaqMan Probe (Fam/Iowa Black Zen quencher)

<400> SEQUENCE: 48
ccctgttgac tttgggaagg gtca 24

<210> SEQ ID NO 49
<211> LENGTH: 21
<212> TYPE: DNA
<213> ORGANISM: Artificial Sequence
<220> FEATURE:
<223> OTHER INFORMATION: Actin forward primer

<400> SEQUENCE: 49
ggacctgact gactacctca t 21

<210> SEQ ID NO 50
<211> LENGTH: 22
<212> TYPE: DNA
<213> ORGANISM: Artificial Sequence
<220> FEATURE:
<223> OTHER INFORMATION: Actin reverse primer #1

<400> SEQUENCE: 50
cgtagcacag cttctcctta at 22

<210> SEQ ID NO 51
<211> LENGTH: 22
<212> TYPE: DNA
<213> ORGANISM: Artificial Sequence
<220> FEATURE:
<223> OTHER INFORMATION: Actin reverse primer #2

<400> SEQUENCE: 51
attaaggaga agctgtgcta cg 22

<210> SEQ ID NO 52
<211> LENGTH: 20
<212> TYPE: DNA
<213> ORGANISM: Artificial Sequence
<220> FEATURE:
<223> OTHER INFORMATION: Actin probe (FAM or VIC/Iowa Black Zen)

<400> SEQUENCE: 52
agcgggaaat cgtgcgtgac 20

<210> SEQ ID NO 53
<211> LENGTH: 23

```
<212> TYPE: DNA
<213> ORGANISM: Artificial Sequence
<220> FEATURE:
<223> OTHER INFORMATION: Gag forward primer

<400> SEQUENCE: 53

ggagctagaa cgattcgcag tta                                        23

<210> SEQ ID NO 54
<211> LENGTH: 22
<212> TYPE: DNA
<213> ORGANISM: Artificial Sequence
<220> FEATURE:
<223> OTHER INFORMATION: Gag reverse primer

<400> SEQUENCE: 54

tgtagctgtc ccagtatttg tc                                         22

<210> SEQ ID NO 55
<211> LENGTH: 30
<212> TYPE: DNA
<213> ORGANISM: Artificial Sequence
<220> FEATURE:
<223> OTHER INFORMATION: Gag probe (FAM/Iowa Black Zen)

<400> SEQUENCE: 55

cctggcctgt tagaaacatc agaaggctgt                                 30

<210> SEQ ID NO 56
<211> LENGTH: 49
<212> TYPE: DNA
<213> ORGANISM: Artificial Sequence
<220> FEATURE:
<223> OTHER INFORMATION: Non-targeting shRNA sequence

<400> SEQUENCE: 56

gccgctttgt aggatagagc tcgagctcta tcctacaaag cggcttttt            49
```